(12) United States Patent
Gainer et al.

(10) Patent No.: US 11,278,621 B2
(45) Date of Patent: *Mar. 22, 2022

(54) TRANS CAROTENOIDS, THEIR SYNTHESIS, FORMULATION AND USES

(71) Applicant: Diffusion Pharmaceuticals LLC, Charlottesville, VA (US)

(72) Inventors: John L. Gainer, Charlottesville, VA (US); Marc Lanz, Reitnau (CH)

(73) Assignee: DIFFUSION PHARMACEUTICALS LLC, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,709

(22) Filed: Mar. 20, 2018

(65) Prior Publication Data
US 2018/0271979 A1    Sep. 27, 2018

Related U.S. Application Data

(60) Continuation of application No. 14/993,047, filed on Jan. 11, 2016, now Pat. No. 9,950,067, which is a division of application No. 13/137,324, filed on Aug. 5, 2011, now abandoned, which is a division of
(Continued)

(51) Int. Cl.
| | |
|---|---|
| A61K 41/00 | (2020.01) |
| A61K 45/06 | (2006.01) |
| A61K 9/19 | (2006.01) |
| A61K 31/202 | (2006.01) |
| A61K 31/11 | (2006.01) |
| A61N 5/10 | (2006.01) |
| C07C 57/03 | (2006.01) |

(Continued)

(52) U.S. Cl.
CPC ............ *A61K 41/0038* (2013.01); *A61K 9/19* (2013.01); *A61K 31/11* (2013.01); *A61K 31/202* (2013.01); *A61K 45/06* (2013.01); *A61N 5/10* (2013.01); *C07C 57/03* (2013.01); *C07C 57/13* (2013.01); *C07C 69/602* (2013.01)

(58) Field of Classification Search
CPC .... A61K 41/0038; A61K 9/19; A61K 31/202; A61K 45/06; A61N 5/10
USPC .......................................................... 514/560
See application file for complete search history.

(56) References Cited

U.S. PATENT DOCUMENTS

| | | |
|---|---|---|
| 2,175,843 A | 10/1939 | Kuhn et al. |
| 2,948,748 A | 8/1960 | Guex et al. |
| 3,489,806 A | 1/1970 | Gutmann et al. |

(Continued)

FOREIGN PATENT DOCUMENTS

| | | |
|---|---|---|
| AU | 2003215396 | 9/2003 |
| CA | 2477245 | 9/2003 |

(Continued)

OTHER PUBLICATIONS

U.S. Appl. No. 60/907,718, filed Apr. 13, 2007, Gainer, J.L.
(Continued)

*Primary Examiner* — Deborah D Carr
(74) *Attorney, Agent, or Firm* — Hoxie & Associates LLC

(57) ABSTRACT

The invention relates to trans carotenoid compounds and salts thereof as well as compositions thereof, methods for making them, and uses thereof. These compounds are useful in improving diffusivity of oxygen between red blood cells and body tissues in mammals including humans.

29 Claims, 3 Drawing Sheets

Related U.S. Application Data application No. 11/361,054, filed on Feb. 24, 2006, now Pat. No. 8,030,350.

(60) Provisional application No. 60/655,422, filed on Feb. 24, 2005.

(51) Int. Cl.
  *C07C 57/13* (2006.01)
  *C07C 69/602* (2006.01)

(56) References Cited

U.S. PATENT DOCUMENTS

| | | |
|---|---|---|
| 3,687,990 A | 8/1972 | Gutmann et al. |
| 3,788,468 A | 1/1974 | Gainer |
| 3,853,933 A | 12/1974 | Siciliano |
| 3,853,993 A | 12/1974 | Gainer |
| 3,965,261 A | 6/1976 | Gainer |
| 3,975,519 A | 8/1976 | Gainer |
| 4,009,270 A | 2/1977 | Gainer, Jr. |
| 4,038,144 A | 7/1977 | Gainer |
| 4,046,880 A | 9/1977 | Gainer |
| 4,070,460 A | 1/1978 | Gainer, Jr. |
| 4,099,270 A | 7/1978 | Jabour |
| 4,105,855 A | 8/1978 | Schulz et al. |
| 4,176,179 A | 11/1979 | Gainer |
| 4,216,211 A | 8/1980 | Francis |
| 4,699,664 A | 10/1987 | Hettiarachchy et al. |
| 4,727,064 A | 2/1988 | Pitha |
| 5,032,613 A | 7/1991 | Watson |
| 5,053,240 A | 10/1991 | Todd, Jr. |
| 5,107,030 A | 4/1992 | Babler |
| 5,424,407 A * | 6/1995 | Tanaka .............. C09B 61/00 127/32 |
| 5,472,946 A | 12/1995 | Peck et al. |
| 5,811,119 A | 9/1998 | Mehta et al. |
| 5,817,332 A | 10/1998 | Urtti et al. |
| 6,060,511 A | 5/2000 | Gainer |
| 6,150,561 A | 11/2000 | Kreienbuhl et al. |
| 6,235,311 B1 | 5/2001 | Ullah et al. |
| 6,555,526 B2 | 4/2003 | Matsuo et al. |
| 6,855,734 B2 | 2/2005 | Messadek |
| 7,145,025 B2 | 12/2006 | Lockwood et al. |
| 7,317,008 B2 | 1/2008 | Lockwood et al. |
| 7,351,844 B2 * | 4/2008 | Gainer .............. A61P 9/12 554/224 |
| 7,446,101 B1 | 11/2008 | Madhavi et al. |
| 7,521,584 B2 | 4/2009 | Lockwood et al. |
| 7,759,506 B2 | 7/2010 | Gainer et al. |
| 7,887,840 B2 | 2/2011 | Curatolo et al. |
| 7,919,527 B2 | 4/2011 | Gainer et al. |
| 8,017,653 B2 | 9/2011 | Gainer et al. |
| 8,030,350 B2 * | 10/2011 | Gainer .............. C07C 57/03 514/547 |
| 8,206,751 B2 | 6/2012 | Gainer |
| 8,269,027 B2 | 9/2012 | Gainer et al. |
| 8,293,804 B2 | 10/2012 | Gainer |
| 8,901,174 B2 | 12/2014 | Gainer |
| 8,974,822 B2 | 3/2015 | Gainer et al. |
| 9,604,899 B2 | 3/2017 | Gainer et al. |
| 9,950,067 B2 | 4/2018 | Gainer et al. |
| 10,016,384 B2 | 7/2018 | Gainer et al. |
| 10,130,689 B2 | 11/2018 | Gainer |
| 2002/0055486 A1 | 5/2002 | Matsuo et al. |
| 2002/0065320 A1 | 5/2002 | Messadek |
| 2003/0072801 A1 | 4/2003 | Curatolo et al. |
| 2003/0180281 A1 | 9/2003 | Bott et al. |
| 2003/0180282 A1 | 9/2003 | Serebruany et al. |
| 2003/0186931 A1 | 10/2003 | Matsuo et al. |
| 2004/0014725 A1 | 1/2004 | Gainer |
| 2004/0109920 A1 | 6/2004 | Reuscher et al. |
| 2004/0116729 A1 | 6/2004 | Gainer et al. |
| 2004/0162329 A1 | 8/2004 | Lockwood et al. |
| 2005/0113372 A1 | 5/2005 | Lockwood et al. |
| 2006/0194973 A1 | 8/2006 | Gainer et al. |
| 2006/0233877 A1 | 10/2006 | Messadek et al. |
| 2006/0276372 A1 | 12/2006 | Lockwood et al. |
| 2006/0281724 A1 | 12/2006 | Loria |
| 2007/0088248 A1 | 4/2007 | Glenn |
| 2007/0135521 A1 | 6/2007 | Okada et al. |
| 2007/0161610 A1 | 7/2007 | Gainer et al. |
| 2007/0166339 A1 | 7/2007 | Gupta |
| 2007/0203353 A1 | 8/2007 | Gainer et al. |
| 2008/0113031 A1 | 5/2008 | Moodley et al. |
| 2008/0255246 A1 | 10/2008 | Gainer |
| 2009/0110746 A1 | 4/2009 | Gainer |
| 2009/0118227 A1 | 5/2009 | Jouni et al. |
| 2009/0169586 A1 | 7/2009 | Tracton |
| 2009/0176287 A1 | 7/2009 | Schmidt-Dannert et al. |
| 2010/0137436 A1 | 6/2010 | Gainer et al. |
| 2010/0322918 A1 | 12/2010 | Gainer |
| 2011/0035256 A1 | 2/2011 | Shkedi et al. |
| 2011/0196038 A1 | 8/2011 | Gainer et al. |
| 2011/0294884 A1 | 12/2011 | Gainer et al. |
| 2011/0300213 A1 | 12/2011 | Gainer et al. |
| 2012/0095099 A1 | 4/2012 | Gainer et al. |
| 2013/0018014 A1 | 1/2013 | Gainer |
| 2014/0051759 A1 | 2/2014 | Gainer et al. |
| 2015/0352068 A1 | 12/2015 | Gainer et al. |
| 2016/0199490 A1 | 7/2016 | Gainer et al. |
| 2017/0202798 A1 | 7/2017 | Gainer et al. |
| 2019/0038586 A1 | 2/2019 | Gainer et al. |
| 2019/0083439 A1 | 3/2019 | Gainer |
| 2019/0083584 A1 | 3/2019 | Gainer |

FOREIGN PATENT DOCUMENTS

| | | |
|---|---|---|
| CA | 2524573 | 11/2004 |
| CH | 522 572 | 10/1969 |
| CN | 1215723 | 5/1999 |
| CN | 1671643 | 9/2005 |
| CN | 1708480 | 12/2005 |
| CN | 1243120 | 2/2006 |
| CN | 1842512 | 10/2006 |
| CN | 1997365 | 7/2007 |
| CN | 10-1180257 | 5/2008 |
| CN | 100033 | 11/2016 |
| EP | 0 612 815 | 8/1994 |
| EP | 0 908 449 | 9/1998 |
| EP | 1 192 947 | 4/2002 |
| EP | 1 621 199 A1 | 2/2006 |
| EP | 1 667 954 | 6/2006 |
| GB | 2 353 934 | 3/2001 |
| JP | 45-014114 | 5/1970 |
| JP | 63-059831 | 3/1983 |
| JP | 61-254161 | 11/1986 |
| JP | 63-222114 | 9/1988 |
| JP | 1-238536 | 9/1989 |
| JP | 02-121934 | 5/1990 |
| JP | A 03-056412 | 3/1991 |
| JP | A 04-264020 | 9/1992 |
| JP | 05-032531 | 2/1993 |
| JP | A 05-178765 | 7/1993 |
| JP | 06-248193 | 9/1994 |
| JP | 07-023736 | 1/1995 |
| JP | 07-223960 | 8/1995 |
| JP | A 07-291854 | 11/1995 |
| JP | 09-512552 | 12/1997 |
| JP | 10-502388 | 3/1998 |
| JP | 11-19261 | 1/1999 |
| JP | 11-029466 | 2/1999 |
| JP | A-11-180901 | 7/1999 |
| JP | 11-209642 | 8/1999 |
| JP | 2000-007570 | 1/2000 |
| JP | 2001-511135 | 8/2001 |
| JP | 2001-302517 | 10/2001 |
| JP | 2002-524535 | 8/2002 |
| JP | 2002-538113 | 11/2002 |
| JP | 2002-348275 A | 12/2002 |
| JP | 2003-026607 | 1/2003 |
| JP | 2003-507430 | 2/2003 |
| JP | 2003-201238 | 7/2003 |
| JP | 2005-053841 | 3/2005 |
| JP | 2005-518453 | 6/2005 |

(56) References Cited

FOREIGN PATENT DOCUMENTS

| | | |
|---|---|---|
| JP | 2006-525270 | 11/2006 |
| JP | 2006-342108 | 12/2006 |
| JP | 2007-522076 | 8/2007 |
| JP | 2010-106029 | 12/2009 |
| JP | 2010-090151 | 4/2010 |
| JP | 2010-229137 | 5/2010 |
| KR | 1999-0036861 | 5/1999 |
| KR | 10-2006-0020616 | 3/2006 |
| KR | 10-2010-0016396 | 2/2010 |
| RU | 2107496 | 3/1998 |
| RU | 2226096 | 3/2004 |
| RU | 2256446 | 7/2005 |
| RU | 2265434 | 12/2005 |
| WO | WO 1992/015544 | 9/1992 |
| WO | WO 1995/000130 | 1/1995 |
| WO | WO 1998/014183 | 4/1998 |
| WO | WO 1998/032421 | 7/1998 |
| WO | WO 1999/015150 | 4/1999 |
| WO | WO 2000/015262 | 3/2000 |
| WO | WO 2001/013933 A2 | 3/2001 |
| WO | WO 2001/013933 A3 | 9/2002 |
| WO | WO 2003/059270 A2 | 7/2003 |
| WO | WO 2003/072734 | 9/2003 |
| WO | WO 2004/005353 | 1/2004 |
| WO | WO 2004/011423 | 2/2004 |
| WO | WO 2004/041284 A1 | 5/2004 |
| WO | WO 2004/048323 | 6/2004 |
| WO | WO 2004/049095 | 6/2004 |
| WO | WO 2004/091630 A1 | 10/2004 |
| WO | WO 2004/049095 A3 | 12/2004 |
| WO | WO 2005/004854 | 1/2005 |
| WO | WO 2005/028411 | 3/2005 |
| WO | WO 2005/120495 | 12/2005 |
| WO | WO 2006/039685 | 4/2006 |
| WO | WO 2006/083780 A2 | 8/2006 |
| WO | WO 2006/093348 | 9/2006 |
| WO | WO 2006/104610 | 10/2006 |
| WO | WO 2007/072529 | 6/2007 |
| WO | WO 2008/014685 | 2/2008 |
| WO | WO 2008/027687 | 3/2008 |
| WO | WO 2008/102563 | 8/2008 |
| WO | WO 2008/135090 | 11/2008 |
| WO | WO 2008/136900 | 11/2008 |
| WO | WO 2009/058399 | 5/2009 |
| WO | WO 2009/111688 | 9/2009 |
| WO | WO 2010/151314 | 12/2010 |
| WO | WO 2011/152869 | 12/2011 |
| WO | WO 2017/165667 | 9/2017 |

OTHER PUBLICATIONS

U.S. Appl. No. 61/001,095, filed Oct. 31, 2007, Gainer, J.L., et al.
U.S. Appl. No. 61/350,804, filed Jun. 2, 2010, Gainer, J.L., et al.
Ahmad, A.S. et al., "Neuroprotection by cretin in a hemi-parkinsonian rat model," *Pharmacology Biochemistry and Behavior*, vol. 81, pp. 805-813, (2005).
Abusuev, A. A., "Clinical Course of Myocardial Infarction in Treatment with Perfluorane, in Perfluorocarbon Compounds in Experimental and Clinical Medicine," *Collected Works of the Russian Scientific Conference*, St. Petersburg, 2004, p. 12 (No English Translation Available.).
Bennett, M.H. et al., "Hyperbaric oxygen therapy for late radiation tissue injury (Review)," *The Cochrane Collaboration* Published by John Wiley & Sons, Ltd., Copyright 2009, Issue 2.
Boileau, T. W.-M., et al., "Bioavailability of all-trans and cis-Isomers of Lycopene," *Experimental Biology and Medicine*, vol. 227, pp. 914-919, (2002); http://ebm.sagepub.com/content/227/10/914.
Borisova, I.V. et al., "Renal and Neuroprotective Effects of Perfluorane in Induced Toxic Renal Injury in Rats," Medline.ru-Biomeditsinskii Zhurnal, vol. 5, Art. 16, pp. 136-139, (2004).
Britton, G. et al., "Isolation and Analysis," *Carotenoids*, vol. IA, pp. 103-107; p. 283, Birkhauser Verlag, Basel, (1995).

Broderick, J.P., et al., "Finding The Most Powerful Measures of the Effectiveness of Tissue Plasminogen Activator in the NINDS tPA Stroke Trial," *Stroke*, vol. 31, No. 10, pp. 2335-2341, (2000).
Brown, J. Martin, et al., "The Unique Physiology of Solid Tumors: Opportunities (and Problems) for Cancer Therapy," *Cancer Research*, vol. 58, pp. 1408-1416,(1998).
Buchta and Andree, "The Total Synthesis of trans-2,2-Bisdimethyl-crocetin-dimetyl ester and trans-Crocetin-dimethyl ester," *Naturwiss*, (1959).
Buchta, E. et al, "Eine Totalsynthese des „all"-trans-Crocetin-dimethylesters2, *Chemischte Berichte Jahrg.*, vol. 93, pp. 1349-1353, (1960).
Bui, Q-C et al., "The Efficacy of Hyperbaric Oxygen Therapy in the Treatment of Radiation-Induced Late Side Effects," *Int. J. Radiation Oncology Biol. Phys.*, vol. 60, No. 3, pp. 871-878, (2004).
Burukhina, A.N. et al., "Experience of Using Perfluorane in Treating Acute Massive Hemorrhage in Obstetric Practice, in Collected Works of the 12th Scientific and Practical Conference of Physicians Topical Issues in Modern Medicine," *Novosibirsk*, Chapter 2, pp. 39-40, (2002).
Calvo, W. et al., "Time—and dose-related changes in the white matter of the rat brain after single doses of X rays," *The British Journal of Radiology*, vol. 61, pp. 1043-1052, (1988).
Cianci, P. "Hyperbaric therapy for radiation injury," *Radiation Injury, Advances in Management and Prevention* edited by J.L. Meyer, et al., pp. 98-109, (1999).
Cheng, N.T. et al., "Intravenous thrombolysis for acute ischemic stroke within 3 hours versus between 3 and 4.5 hours of symptom onset," *The Neurohospitalist*, vol. 5, Issue 3, pp. 101-109; (2015).
Clark, W.M., et al., "The rtPA (Alteplase) 0- to 6-Hour Acute Stroke Trial, Part A (A0276g): Results of a Double-Blind, Placebo-Controlled, Multicenter Study," *Stroke*, vol. 31, No. 4, pp. 311-816, (2000).
CMC Co. Ltd., published Pharmaceutical Formulation Strategies and New Technology, Mar. 31, 2007, first printing, p. 88.
Coppola, G.M., "Amberlyst-15, A Superior Acid Catalyst for the Cleavage of Acetals," *Syn. Communications* 1021 (Dec. 1984).
Craw, M. and Lambert, C., "The Characterisation of the Triplet State of Crocetin, a Water Soluble Carotenoid, by Nanosecond Laser Flash Photolyses," *Photochemistry and Photobiology*, vol. 38, No. 2, pp. 241-243, (1983).
Chryssanthi, D.G., et al., "A New Validated SPE-HPLC Method for Monitoring Crocetin in Human Plasma—Application After Saffron Tea Consumption," Journal of Pharmaceutical and Biomedical Analysis, vol. 55, pp. 563-568, (2011); DOI: 10.1016/j.jpba.2011.02.018.
Cutright, D.E. et al., "Long-Term Effects of Radiation on the Vascularity of Rat Bone—Quantitative Measurements with a New Technique," Radiation Research, vol. 48, pp. 402-408 (1971).
Database Caplus, Chemical Abstracts Service, Columbus, Ohio, US, (1988), XP002317165 [JP 63 059831].
Database Caplus, Chemical Abstracts Service, Columbus, Ohio, US, (1993), XP002317166 [JP 05 032531].
Denninghoff, et al., "Retinal Imaging Techniques in Diabetes," *Diabetes Technology & Therapeutics*, vol. 2, No. 1, pp. 111-113 (2000).
Finney, J., et al., "Protection of the ischemic heart with DMSO alone or DMSO with hydrogen peroxide," *Annals of The New York Academy of Sciences*, vol. 141, No. I, pp. 231-241, Mar. 15, 1967.
Gainer, J.L., et al., "Oxygen diffusion and atherosclerosis," *Atherosclerosis*, vol. 19, pp. 135-138, (1974).
Gainer, J.L. et al., "Using Excess Volume of Mixing to Correlate Diffusivities in Liquids," *Chem. Eng. Commun.*, vol. 15, pp. 323-329, (1982).
Gainer, J.L., et al., "The Effect of Crocetin on Hemorrhagic Shock in Rats," *Circulatory Shock*, vol. 41, pp. 1-7, (1993).
Gainer, J.L., "Altering Diffusivities in Dilute Polymeric and Biological Solutions," *Ind. Engr. Chem. Research*, vol. 33, pp. 2341-2344, (1994).
Gainer, J.L. et al., "The effect of trans sodium crocetinate (TSC) in a rat oleic acid model of acute lung injury," *Pulmonary Pharmacology & Therapeutics*, Academic Press, GB, vol. 18, No. 3, pp. 213-216, (Jun. 1, 2005), XP004737366.

(56) References Cited

OTHER PUBLICATIONS

Gainer, J. L., "Trans-Sodium Crocetinate for Treating Hypoxia/Ischemia," *Expert Opinion on Investigational Drugs*, vol. 17, No. 6, pp. 917-924, (2008).
Galinski, Erwin A., et al., "The Kosmotropic (Structure-Forming) Effect of Compensatory Solutes," *Comp. Biochem. Physiol.*, vol. 117A, No. 3, pp. 357-365, (Dec. 31, 1997).
General Information on Perfluorane, Medline.ru-Biomeditsinskii Zhurnal, 2004, vol. 5, Art. 16, pp. 68-69, www.medline.ru/public/art/tom5/art8-perf2.phtm (with English translation).
Ghandehari, K. et al., "Thrombolysis in stroke patients; Problems and limitations," *Iran Journal of Med. Sci.*, vol. 35, Issue 2, pp. 145-148, (2010).
Giassi, L.J. et al., "Trans Sodium Crocetinate Restores Blood Pressure, Heart Rate, and Plasma Lactate after Hemorrhagic Shock," *Journal of Trauma*, vol. 51, pp. 932-938, (2001).
Giassi, L.J., et al., "Trans Sodium Crocetinate for Hemorrhagic Shock: Effect of Time Delay in Initiating Therapy," *Shock*, vol. 18, No. 6, pp. 585-588, (2002).
Gibson, T.W. et al., "Sulfinic Acid Catalyzed Isomerization of Olefins," *J. Org. Chem.*, vol. 41, No. 5, pp. 791-793 (1976), XP002325593.
Gill, A.L. et al., "Hyperbaric oxygen: its uses, mechanisms of action and outcomes," *Q. J. Med.*, vol. 97, pp. 385-395, (2004).
Goldstick, T.K., Ph.D, "Diffusion of Oxygen in Protein Solutions," Dissertation, University of California, Berkeley, CA, pp. 13-28, (1966).
Gree, R. et al., "Fumaraldehyde Monodimethyl Acetal: An Easily Accessible and Versatile Intermediate," *Tetrahedron Letters*, vol. 27, No. 41, pp. 4983-4986, (1986).
Greenwood, T.W. et al., "Hyperbaric Oxygen and Wound Healing in Post-Irradiation Head and Neck Surgery," Brit. J. Surg., vol. 60, No. 5, pp. 394-397, (May 1973).
Group, N.r.-P.S.S., "Tissue Plasminogen Activator For Acute Ischemic Stroke," *The New England Journal of Medicine*, vol. 333, No. 24, pp. 1581-1587, (1995).
Holland, R.A.B. et al., "Kinetics of O2 Uptake and Release by Red Cells in Stopped-Flow Apparatus: Effects of unstirred Layer," *Respiration Physiology*, vol. 59, pp. 71-91, (1985).
Holloway, G.M., et al., "The carotenoid crocetin enhances pulmonary oxygenation," *The American Physiological Society*, pp. 683-686, Department of Chemical Engineering, and Dept. of Anesthesiology, School of Medicine, Univ. of VA, Charlotteville, Va, (1988).
Huxley, V.H., et al., "The Effect of the Red Cell Membrane and a Diffusion Boundary Layer on the Rate of Oxygen Uptake by Human Erythrocytes," *J. Physiol.*, vol. 316, pp. 75-83, (1981).
International Preliminary Examination Report on Patentability (IPRP) (Chapter 1) for PCT/US2003/005521, prepared Aug. 23, 2004.
International Preliminary Report on Patentability dated May 25, 2007 in PCT/US2003/026424; prepared May 10, 2007.
International Preliminary Report on Patentability for International Application No. PCT/US2006/006422 dated Aug. 28, 2007.
International Preliminary Report on Patentability dated Oct. 13, 2009 in International Application No. PCT/US2008/004708.
International Preliminary Report on Patentability for International Application No. PCT/US2008/012440 dated May 4, 2010.
International Preliminary Report on Patentability dated Jan. 12, 2012 in PCT/US2010/001794.
International Preliminary Report on Patentability (IPRP) (Chapter I) for PCT/US2011/000997, dated Dec. 4, 2012.
International Search Report and for International Application No. PCT/US2003/005521 dated Dec. 24, 2003.
International Search Report for International Application No. PCT/US2003/026424 dated Nov. 5, 2004.
International Search Report and Written Opinion for International Application No. PCT/US2006/006422 dated Oct. 19, 2006.
International Search Report and Written Opinion dated Jul. 22, 2008 for International Application No. PCT/US2008/004708.
International Search Report and Written Opinion for International Application No. PCT/US2008/012440 dated Mar. 25, 2009.
International Search Report and Written Opinion for International Application No. PCT/US2010/001794 dated Sep. 1, 2010.
International Search Report and Written Opinion for International Application No. PCT/US2011/000997 dated Sep. 9, 2011.
Ingall, T., "Stroke-Incidence, Mortality, Morbidity And Risk," *Journal of Insurance Medicine*, vol. 36, pp. 143-152, (2004).
Isler, O. et al., "Anwendung der Wittig-Reaktion zur Synthese von Estern des Bixins und Crocetins," *Helv. Chim. Acta*, vol. 40, No. 139, pp. 1242-1249, (1957); XP008042920.
Jansen, F.J.H.M., et al., "Synthesis and Characterization of All-$E(12,12'$-$^{13}C_2)$-, $(13,13'$-$^{13}C_2)$-, $(14,14'$-$^{13}C_2)$-, $(15,15'$-$^{13}C_2)$- and $(20,20'$-$^{13}C_2)$astaxanthin," *Recl. Trav. Chim. Pays-Bas*, vol. 113, p. 552-562, (1994).
Jiho, Inc., Design and Evaluation of Oral Formulation, pp. 337-339, (1995); No English Translation Available.
Johnson, M.E., et al., "Synergistic Effects of Chemical Enhancers and Therapeutic Ultrasound on Transdermal Drug Delivery," *Journal of Pharmaceutical Sciences*, vol. 85, No. 7, pp. 670-679, (1996).
Kalani, M., et al., "Hyperbaric Oxygen (HBO) Therapy in Treatment of Diabetic Foot Ulcers Long-term Follow-up," *Journal of Diabetes & Its Complications*, pp. 153-158, (2002).
Kamiryo, T. et al., "Histological Changes in the Normal Rat Brain After Gamma Irradiation," *Acta Neurochir (Wien)*, vol. 138, pp. 451-459, (1996).
Kamiryo, T. et al., "Radiosurgery-induced Microvascular Alterations Precede Necrosis of the Brain Neuropil," *Neurosurgery*, vol. 49, No. 2, pp. 409-415, (2001).
Kichev, G.S. et al., "Experience of Using Perfluorane in Treating Critical Conditions of Various Geneses," *Medline.ru-Biomeditsinskii Zhurnal*, vol. 5, Art. 53, pp. 175-177, (2004); No English Translation Available.
Koynova, R., et al., "Modulation of Lipid Phase Behavior by Kosmotropic and Chaotropic Solutes—Experiment and Thermodynamic Theory," *Eur Biophys J*, vol. 25, pp. 261-274, (1997).
Laidig, K.E. et al., "Altering Diffusivity in Biological Solutions through Modification of Solution Structure and Dynamics," *Journal of the American Chemical Society*, vol. 120, No. 36, pp. 9394-9395, (1998); XP002970835.
Lancrajan, I., et al., "Carotenoid incorporation into natural membranes from artificial carriers: liposomes and beta-cyclodextrins," *Chemistry and Physics of Lipids*, vol. 112, pp. 1-10, (2001); XP55044152.
Lang, A.E., et al., "Parkinson's Disease," *New England Journal of Medicine*, vol. 339, No. 15, pp. 1044-1053, (1998).
Lapchak, P.A., et al., "Neuroprotective Effects of the Spin Trap Agent Disodium-[(tert-butylimino)methyl]benzene-1,3-disulfonate N-Oxide (Generic NXY-059) in a Rabbit Small Clot Embolic Stroke Model: Combination Studies With the Thrombolytic Tissue Plasminogen Activator," *Stroke*, vol. 33, No. 5, pp. 1411-1415, (2002); DOI: 10.1161/01.STR.0000015346.00054.8B.
Lapchak, P.A., et al., "Comparison of Tenecteplase With Alteplase On Clinical Rating Scores Following Small Clot Embolic Strokes in Rabbits," *Experimental Neurology*, vol. 185, pp. 154-159, (2004); DOI: 10.1016/j.expneurol.2003.09.009.
Lapchak, P.A. et al., "Transcranial Infrared Laser Therapy Improves Clinical Rating Scores After Embolic Strokes in Rabbits," *Stroke*, vol. 35, No. 8, pp. 1985-1988, (2004); DOI: 10.1161/01.STR. 0000131808.69640.b7.
Lapchak, P.A., "Memantime, an uncompetitive low affinity NMDA open-channel antagonist improves clinical rating scores in a multiple infarct embolic stroke model in rabbits," *Brain Research*, vol. 1088, No. 1, pp. 141-147, (2006); DOI: 10.1016/j.brainres.2006. 02.093.
Lapchak, P.A., et al., "Advances in Ischemic Stroke Treatment: Neuroprotective And Combination Therapies," *Expert Opin. Emerging Drugs*, vol. 12, No. 2, pp. 1-16, (2007); DOI: 10.1517/14728214. 12.2.
Lapchak, P.A., "The *Phenylpropanoid* Micronutrient Chlorogenic Acid Improves Clinical Rating Scores in Rabbits Following Multiple Infarct Ischemic Strokes: Synergism With Tissue Plasminogen

(56) References Cited

OTHER PUBLICATIONS

Activator," *Experimental Neurology*, vol. 205, No. 2, pp. 407-413, (2007); DOI: 10.1016/j.expneurol.2007.02.017.

Lapchak, P.A., et al., "Transcranial Near-Infrared Light Therapy Improves Motor Function Following Embolic Strokes In Rabbits: An Extended Therapeutic Window Study Using Continuous And Pulse Frequency Delivery Modes," *Neuroscience*, vol. 148, pp. 907-914, (2007); DOI: 10.1016/j.neuroscience.2007.07.002.

Lapchak, P.A., et al., "Therapeutic Window for Nonerythropoietic carbamylated-erythropoietin to Improve Motor Function Following Multiple Infarct Ischemic Strokes in New Zealand White Rabbits," *Brain Research*, vol. 1238, pp. 208-214, (2008); DOI: 10.1016/j.brainres.2008.08.017.

Lapchak, P.A., "Efficacy and Safety Profile of the Carotenoid Trans Sodium Crocetinate Administered to Rabbits Following Multiple Infarct Ischemic Strokes: A Combination Therapy Study with Tissue Plasminogen Activator," *Brain Research*, vol. 1309, pp. 136-145, (2010), XP-002686117; DOI: 10.1016/j.brainres.2009.10.067.

Letham, D.S., et al., "The Synthesis of Radioisotopically Labelled Zeatin," *Phytochemistry*, vol. 10, pp. 2077-2081, (1971).

Lever, M., et al., "Some Ways of Looking at Compensatory Kosmotropes and Different Water Environments," *Comparative Biochemistry and Physiology, Part A*, vol. 130, pp. 471-486, (2001).

Lide, D.R. Ph.D., "CRC Handbook of Chemistry and Physics," *CRC Press*, 79th Edition, Boca Raton, FL, pp. 6-181, (1998).

Lishner, M., et al., "Treatment of Diabetic Perforating Ulcers (Mal Perforant) with Local Dimethylsulfoxide," *J. Am Geriatr Soc.*, vol. 33, No. 1, pp. 41-43, (1985).

Lyubimova, N., et al., "Experimental Evidence to Support the Hypothesis that Damage to Vascular Endothelium Plays the Primary Role in the Development of Late Radiation-induced CNS Injury," *The British Journal of Radiology*, vol. 77, pp. 488-492, (2004).

Maehara, Y., *Fukuoka Medical Journal*, vol. 88, No. 11, 1997, pp. 337-344; No English Translation Available.

Magazu, S., et al., "α,α-Trehalose-Water Solutions. VIII. Study of the Diffusive Dynamics of Water by High-Resolution Quasi Elastic Neutron Scattering," *J. Phys. Chem. B*, vol. 110, No. 2, pp. 1020-1025, (2006).

Magesh, V., "Studies on the anti-tumor effect of crocetin against benzo(a)pyrene induced lung cancer in Swiss albino mice," *Biomedicine*, (Chennai india) (Dec. 31, 2003), vol. 23 (3rd & 4th Edition), pp. 96-99, Database HCAPLUS on STN, DN 141:388250, Abstract.

Marx, R.E., D.D.S., "Osteoradionecrosis: A New Concept of its Pathophysiology," *J. Oral Maxillofac Surg*, vol. 41, pp. 283-288, (1983).

Marx, R.E., et al., "Relationship of Oxygen Dose to Angiogenesis Induction in Irradiated Tissue," *The American Journal of Surgery*, vol. 160, pp. 519-524, (1990).

Mayer, R., et al., "Hyperbaric Oxygen and Radiotherapy," *Strahlenther. Onkol.*, vol. 181, No. 2, pp. 113-123, (2005); DOI: 10.1007/s00066-005-1277-y.

Miyagawa, H., et al., "Pathogenesis of Delayed Radiation Injury in the Rat Spinal Cord After X-ray Irradiation," *Neuropathology*, vol. 16, pp. 126-132, (1996).

Moelbert, S., et al., "Kosmotropes and Chaotropes: Modeling Preferential Exclusion, Binding and Aggregate Stability," *Biophysical Chemistry*, vol. 112, pp. 45-57, (2004); DOI: 10.1016/j.bpc.2004.06.012.

Notification Concerning Transmittal of International Preliminary Report on Patentability (Chapter 1 of the Patent Cooperation Treaty) for International Application No. PCT/US2008/012440 dated May 14, 2010.

Ohga, E., et al., "The relationship between adhesion molecules and hypoxia," *Nippon Rinsho*, vol. 58, No. 8, pp. 1587-1591, (2000); No English Translation Available.

Okeda, R., "Pathological Changes in the Cerebral Medullary Arteries of Five Autopsy Cases of Malignant Nephrosclerosis: Observation by Morphometry and Reconstruction of Serial Sections," *Neuropathology*, vol. 23, pp. 153-160, (2003).

Okonkwo, D.O., et al., "Trans-sodium Crocetinate Increases Oxygen Delivery to Brain Parenchyma in Rats on Oxygen Supplementation," *Neuroscience Letters*, vol. 352, pp. 97-100, (2003).

Pastores, S.M., et al., "Posttraumatic Multiple-organ Dysfunction Syndrome: Role of Mediators in Systemic Inflammation and Subsequent Organ Failure," *Academic Emergency Medicine*, vol. 3, No. 6, pp. 611-622, (1996).

Pauling, L., "Recent Work on the Configuration and Electronic Structure of Molecules; with some Applications to Natural Products," *Fortschr. Chem. Org. Naturst.*, vol. 3, No. 303, pp. 203-235, (1939).

Pfander, H., et al., "Carotenoid Synthesis: A Progress Report," *Pure &Appl. Chem.*, vol. 69, No. 10, pp. 2047-2060, (1997).

Pfitzner, I., et al., "Carotenoid: methyl-β-cyclodextrin formulations: an improved method for supplementation of cultured cells," *Biochimica et Biophysica Acta*, vol. 1474, No. 2, pp. 163-168, (2000), XP004276552.

Pharmacia, vol. 27, No. 7, pp. 703-705, (1991); No English Translation Available.

Polyakov, N.E., et al., "Inclusion Complexes of Carotenoids with Cyclodextrins: $^1$H NMR, EPR, and Optical Studies," *Free Radical Biology & Medicine*, vol. 36, No. 7, pp. 872-880, (2004); XP27231510.

Re, R., et al., "Isomerization of Lycopene in the Gastric Milieu," *Biochemical and Biophysical Research Communications*, vol. 281, No. 2, pp. 576-581, (2001); DOI: 10.1006/bbrc.2001.4366.

RN: 120523-11-7; CN: 2,4,6,8,10, 12,14,16,18-Eicosanonaenedioic acid, 4,8, 13,17-tetramethyl-potassium sodium salt, (1989).

RN: 147484-59-1; CN: 2,4,6,8-Decatetraenedioic acid, disodium salt, (1993).

RN: 33261-80-2; CN: 2,4,6,8,10,12,14,16,18-Eicosanonaenedioic acid, 4,8,13,17-tetramethyl-dipotassium salt, (1984).

RN: 33261-81-3; CN: 2,4,6,8,10,12,14,16,18-Eicosanonaenedioic acid, 4,8,13,17-tetramethyl-disodium salt, (1984).

Rowinsky, E. K., "Novel Radiation Sensitizers Targeting Tissue Hypoxia," *Oncology*, vol. 13, No. 10, Supplement No. 5, pp. 61-70, (1999), XP009044613.

Roy, J.W., et al, "A Novel Fluid Resuscitation Therapy for Hemorrhagic Shock," *Shock*, vol. 10, No. 3, pp. 213-217, (1998).

Schwieter, U., et al., "Synthesen in der Carotinoid-Reihe 20. Mitteilung[1]) Neue Synthesen von Apocarotinoiden," *Helvetica Chimica Acta*, vol. 49, pp. 369-390, (1966), XP-002575142.

Secor, R.M., "The Effect of Concentration on Diffusion Coefficient in Polymer Solutions," *A.I.Ch.E. Journal*, vol. 11, No. 3, pp. 452-456, (1965).

Seyde, W.C., et al., "Carotenoid Compound Crocetin Improves Cerebral Oxygenation in Hemorrhaged Rats," *Journal of Cerebral Blood Flow and Metabolism*, vol. 6, No. 6, pp. 703-707, (1986).

Shi, Nihon Butsuri Gakkai, "Structure and Function of Cartenoid in Photosynthetic System," *Journal of the Physical Society of Japan*, vol. 50, No. 7, pp. 555-561, (1995); No English Translation Available.

Singer, M., et al., "Intravenous Crocetinate Prolongs Survival in a Rat Model of Lethal Hypoxemia," *Crit Care Med*, vol. 28, No. 6, pp. 1968-1972, (2000).

Snyder, J.M., et al., "*cis*-trans Isomerization of Unsaturated Fatty Acids with *p*-Toluenesulfinic Acid," *J. Am. Oil Chem. Soc.*, vol. 59, No. 11, pp. 469-470, (1982).

Stennett, A.K., et al., "*trans*-Sodium Crocetinate and Diffusion Enhancement," *J. Phys. Chem. B.*, vol. 110, No. 37, pp. 18078-18080, (2006).

Streitwieser, A., et al., Introduction to Organic Chemistry, 2nd Ed., pp. 504-505, (1981).

The Lung perspectives, vol. 9, No. 2, pp. 161-165, (2001); No English Translation Available.

Tong, L., "Cyclodextrins Chemistry: Fundamentals and Application," *Science Press*, pp. 360-364, (2001); No English Translation Available.

Tyssandier, V., et al., "Processing of Vegetable-borne Carotenoids in the Human Stomach and Duodenum," *Am J Physiol Gastrointest Liver Physiol*, vol. 284: G913-G923, (2003).

Vickackaite, V., et al., "Photochemical and Thermal Degradation of a Naturally Occuring Dye Used in Artistic Painting. A Chromatographic, Spectrophotometric and Fluorimetric Study on Saffron," *International Journal of Photoenergy*, vol. 6, pp. 175-183, (2004).

(56) References Cited

OTHER PUBLICATIONS

Wang, Y., et al., "The Effect of Trans-Sodium Crocetinate in a Model of Intracranial Hemorrhage," Abstracts of the Annual Meeting of the Society for Neuroscience, Society for Neuroscience Abstract Viewer and Itinerary Planner, 2 pages, (Nov. 15, 2008) Washington, DC, XP009163975.
Wenkert, E., et al., "Polyene Synthesis. Ready Construction of Retinol-Carotene Fragments (±)-6-(E)-LTB, Leukotrienes, and Corticrocin," Journal of Organic Chemistry, vol. 55, No. 25, pp. 6203-6214, (1990), XP002317164.
White, D.C., "The Histopathologic Basis for Functional Decrements in Late Radiation Injury in Diverse Organs," Cancer, vol. 37, No. 2, pp. 1126-1143, February Supplement, (1976).
Widmer, E., et al., "Technical Procedures for the Syntheses of Carotenoids and Related Compounds from 6-Oxo-isophorone: Syntheses of (3R.3R)-Zeaxanthin," Helvetica Chemica Acta, vol. 73, pp. 861-867, (1990).
Wilkins, E.S., et al., "The Effect of Crocetin on the Irradiation of Walker-256: In Vitro and In Vivo Studies," Cancer Biochem. Biophys., vol. 3, pp. 71-74, (1979), XP008157982.
Williamson, R.A., "An Experimental Study of the Use of Hyperbaric Oxygen to Reduce the Side Effects of Radiation Treatment for Malignant Disease," Int. J. Oral Maxillofac. Surg., vol. 36, pp. 533-540, (2007).
Wirz, R., et al., "Celluloseaffinität von Polyendicarbonsauren vom Typ des Crocetins und von quarternären Ammoniumverbindungen," Helv. Chim. Acta, vol. 63, No. 6, pp. 1738-1745, (1960), XP008042762.
Wurtman, R.J., "Alzheimer's Disease," Scientific American, vol. 252, (1985).
Yamaguchi, K., et al., "Kinetics of $O_2$ Uptake and Release by Human Erythrocytes Studied by a Stopped-flow Technique," The American Physiological Society, vol. 58, pp. 1215-1224, (1985).
Zheng, S., et al., "Crocetin Attenuates Atherosclerosis in Hyperlipidemic Rabbits Through Inhibition of LDL Oxidation," J. Cardiovasc. Pharrnacol, vol. 47, No. 1, pp. 70-76, (2006); XP009135396, ISSN: 0160-2446.
Search Report dated Sep. 15, 2015, issued in Chinese Patent Application No. 201080027664.7 and English translation.
Search Report dated Dec. 14, 2015, issued in Chinese Application No. 201180033875.6, which corresponds to PCT/US2011/000997, and English translation.
Search Report dated Oct. 21, 2016, issued in Chinese Application No. 201510128602.X, which is a national phase of PCT/US2006/006422, and English translation.
Supplementary Partial European Search Report dated Feb. 25, 2005 based on Application No. EP 03 71 1221.
Supplementary Partial European Search Report dated Apr. 21, 2005 based on Application No. EP 03 71 1221.
Supplementary Partial European Search Report dated Nov. 7, 2006.
Supplementary European Search Report dated Apr. 29, 2010 issued by the European Patent Office in one of Applicants' corresponding foreign applications.
Supplementary European Search Report dated Dec. 8, 2010 (corresponding to applicant's European Regional Phase Patent Application No. EP 08844993.9 based on International Patent Application No. PCT/US2008/012440 filed on Oct. 31, 2008).
Supplementary European Search Report dated Oct. 29, 2012 issued by the European Patent Office and Preliminary Opinion.
Supplementary Extended European Search Report dated Nov. 21, 2012 issued by the European Patent Office and Preliminary Opinion.
Supplementary (Extended) European Search Report dated Oct. 21, 2013 in European Patent Application No. EP 11790107.4 issued from PCT/US2011/000997 filed on Jun. 2, 2011, together with the Written Opinion.
Supplementary Extended European Search Report dated Mar. 28, 2013 issued by the European Patent Office and Written Opinion.
Australian Office Action dated Jun. 25, 2008 from corresponding Australian Patent Office.
Australian Office Action dated Mar. 26, 2010 in Applicant's Australian Application No. 2003265617.
Australian Office Action dated Oct. 25, 2010 issued by the Australian Patent Office in one of Applicants' corresponding foreign applications.
Australian Office Action dated Dec. 23, 2011.
Australian Office Action dated Dec. 3, 2014 from the Australian Patent Office for applicant's Australian application corresponding to PCT Application No. PCT/US03/26424.
Australian Office Action dated Dec. 10, 2014 from applicant's Australian application corresponding to PCT Application No. PCT/US2008/012440.
Australian Office Action dated Feb. 25, 2015 from applicant's application corresponding to PCT Application No. PCT/US2011/000997.
Australian Examination Report No. 1 dated Dec. 1, 2016, issued in Australian Patent Application No. 2016201192, which is a National Phase of PCT/US2011/000997.
Canadian Office Action dated Mar. 26, 2013, for applicant's Canadian Patent Application No. 2,598,882 corresponding to PCT/US06/006422 filed Feb. 24, 2006.
Canadian Office Action dated May 30, 2013, for applicant's Canadian Patent Application No. 2,683,760 corresponding to PCT/US2008/004708 filed Apr. 11, 2008.
Canadian Office Action dated Oct. 20, 2009 from Canadian Application No. 2,477,245.
Canadian Office Action dated Jul. 7, 2010 in corresponding Canadian Application No. 2,477,245.
Canadian Office Action dated Oct. 26, 2010 in corresponding Canadian Application No. 2,537,210.
Canadian Office Action dated Jul. 5, 2011 in corresponding Canadian Application No. 2,537,210.
Canadian Office Action dated Nov. 4, 2014 in Canadian Patent Application No. 2,703,946 from national phase of PCT/US2008/012440.
Canadian Office Action dated Apr. 12, 2016, issued in Canadian Patent Application No. 2,765,697, which is the national phase of PCT/US2010/001794.
Canadian Office Action dated Aug. 3, 2016, issued in Canadian Patent Application No. 2,703,946, which corresponds to PCT/US2008/012440.
Canadian Office Action dated Aug. 31, 2016, issued in Canadian Patent Application No. 2,598,882, which is the national phase of PCT/US2006/06422.
Chinese Office Action dated Nov. 7, 2008 in a corresponding application owned by the applicants in Chinese Application No. 03826969.4.
Chinese Third Office Action in Chinese Patent Application No. 03804566.4 dated Jan. 23, 2009 (English Translation Only).
Chinese Office Action and its English Translation dated Feb. 12, 2010 in the Assignee's Chinese application relating to PCT/US2006/006422.
Chinese Office Action dated Mar. 29, 2010 from Chinese Patent Application No. 03826969.4 based on PCT/US2003/026424.
Chinese Office Action and its English Translation dated Feb. 21, 2011 in Assignee's Chinese Patent Application No. 200680013663.0 based on PCT/US2006/006422.
Chinese Office Action and its English Translation dated Apr. 6, 2011 from Chinese Patent Application No. 200680013663.0 based on PCT/US2006/006422.
Chinese Office Action and its English Translation dated Jun. 30, 2011 in Chinese Application No. 2008801143109 (English Translation Only).
Chinese Office Action and its English Translation dated Jan. 18, 2012 in Chinese Patent Application No. 200680013663.0 based on PCT/US2006/006422.
Chinese Office Action and its English translation dated May 3, 2012, from Chinese Patent Application No. 03804566.4 based on PCT/US2003/005521.
Chinese Office Action and its English translation dated Jun. 6, 2012, from Chinese Patent Application No. 200880015671.8 based on PCT/US2008/004708.
Chinese Office Action and its English Translation dated Jun. 14, 2012 from Chinese Patent Application No. 200880114310.9 that corresponds to PCT/US2008/012440.

(56) References Cited

OTHER PUBLICATIONS

Chinese Office Action and its English Translation dated Jan. 28, 2013, from Chinese Patent Application No. 200880015671.8 that corresponds to PCT/US2008/004708.
Chinese Patent Office Decision of Rejection dated May 2, 2013 and its English translation, corresponding to PCT/US2006/06422 filed on Feb. 24, 2006.
Chinese Office Action dated May 6, 2013, from Chinese Patent Application No. 201080027664.7 that corresponds to PCT/US2010/001794, and its English translation.
Chinese Office Action dated Jul. 9, 2013, from Chinese Patent Application No. 200880114310.9 that corresponds to PCT/US2008/012440, and its English translation.
Chinese Office Action and its English translation dated Nov. 1, 2013, from Chinese Patent Application No. 201180033875.6 that corresponds to PCT/US2011/000997.
Chinese Office Action and its English translation dated Mar. 19, 2014, from Chinese Patent Application No. 200880015671.8 that corresponds to PCT/US2008/004708.
Chinese Office Action and its English translation dated Mar. 31, 2014, from Chinese Patent Application No. 201210063676.6 that corresponds to PCT/US2003/026424, filed Aug. 25, 2003.
Chinese Office Action and English Translation dated Jul. 21, 2014 issued in Chinese Patent Application No. 200680013663.0, 9 pp.
Chinese Office Action and English Translation dated Jul. 24, 2014 issued in Chinese Patent Application No. 200880114310.9, 19 pp.
Chinese Office Action dated Aug. 15, 2014 issued in Chinese Patent Application No. 201080027664.7 and English Translation, 13 pp.
Chinese Office Action and English Translation dated Dec. 8, 2014 (Reexamination Decision) from the Chinese Patent Office in applicant's Chinese Application corresponding to PCT Application No. PCT/US06/06422.
Chinese Notice and Office Action and English Translations dated Dec. 22, 2014 from the China Patent Office for applicant's China application corresponding to PCT Application No. PCT/US2011/000997.
Chinese Office Action and its English translation dated May 5, 2015 for national phase of PCT/US2008/004708.
Chinese Office Action and its English translation dated Jun. 24, 2015 for National Phase of PCT/US03/26424 (with translation).
Chinese Fifth Notification of Office Action dated Aug. 17, 2015, issued in Chinese Patent Application No. 200880114310.9 and English translation.
Chinese Third Notification of Office Action dated Sep. 25, 2015, issued in Chinese Patent Application No. 201080027664.7 and English translation.
Chinese Third Notification of Office Action dated Dec. 14, 2015, issued in Chinese Application No. 201180033875.6, which corresponds to PCT/US2011/000997, and English translation.
Chinese Fifth Notification of Office Action dated Jun. 21, 2016, issued in Chinese Patent Application No. 200880015671.8, which is the national phase of PCT/US2008/04708, and English translation.
Chinese Sixth Notification of Office Action dated Aug. 16, 2016, issued in Chinese Patent Application No. 200880114310.9, which is the national phase of PCT/US2008/012440, and English translation.
Chinese First Notification of Office Action dated Oct. 31, 2016, issued in Chinese Application No. 201510128602.X, which is a National Phase of PCT/US2006/006422, and English translation.
Chinese Decision of Rejection dated Nov. 10, 2016, issued in Chinese Application No. 201080027664.7, which is a National Phase of PCT/US2010/001794, and English translation.
Chinese Decision for Rejection and its English Translation dated Nov. 28, 2016 issued in Chinese Patent Application No. 201180033875.6 which is a national phase of PCT/US2011/000997.
Chinese Search Report dated Mar. 18, 2013, and its English translation.
Chinese Search Report dated Jun. 27, 2013, and its English translation.
Chinese Search Report and its English translation dated Mar. 19, 2014, from Chinese Patent Application No. 201210063676.6 that corresponds to PCT/US2003/026424, filed Aug. 25, 2003.
Chinese Search Report dated Oct. 21, 2016, issued in Chinese Application No. 201510128602.X, which is a national phase of PCT/US06/06422, and English translation.
Eurasian Patent Office Action and its English translation dated Nov. 9, 2011.
Eurasian Patent Office Action and its English translation dated Nov. 17, 2011.
European Office Action dated Nov. 9, 2009 in Applicant's European application corresponding to PCT/US2003/005521.
European Office Action dated Nov. 9, 2009 in Applicant's European application corresponding to PCT/US2003/026424.
European Office Action dated Apr. 7, 2011, from European Patent Application No. EP 08742781.1.
European Office Action dated Oct. 17, 2011 from European Patent Application No. EP 08742781.1.
European Office Action dated Oct. 31, 2011, from European Patent Application No. EP 06758166.0.
European Office Action dated Apr. 25, 2012.
European Office Action dated Jun. 11, 2012, from European Patent Application No. EP 08742781.1.
European Office Action dated Mar. 12, 2014, from applicant's European Patent Application No. EP 12166293.6, corresponding to PCT/US2006/006422 filed Feb. 24, 2006.
European Office Action dated Nov. 21, 2014 from the EPO for applicant's EP Application No. 03818748.0 based on PCT/US2003/26424.
European Office Action dated Feb. 2, 2015 from the for applicant's application corresponding to PCT Application No. PCT/US2008/012440.
European Office Action dated Feb. 2, 2015 from the for applicant's application corresponding to PCT Application No. PCT/US03/05521.
European Office Action dated Oct. 27, 2015 that issued in the European application that corresponds to PCT//US03/05521.
European Communication pursuant to Article 94(3) EPC dated May 17, 2016, issued in European Patent Application No. 03 711 221.6, which is the national phase of PCT/US03/05521.
European Communication pursuant to Article 94(3) EPC dated May 19, 2016, issued in European Patent Application No. 03 818 748.0, which is the national phase of PCT/US03/26424.
European Communication pursuant to Article 94(3) EPC dated Jun. 3, 2016, issued in European Patent Application No. 11 790 107.4, which is the national phase of PCT/US2011/000997.
European Communication Pursuant to Article 94(3) EPC dated Jul. 6, 2016, issued in European Patent Application No. 12 166 293.6, which is the national phase of PCT/US2006/006422.
Hungarian Novelty Search Report dated Nov. 5, 2009 (w/translation).
India Office Action dated Oct. 23, 2008 in a corresponding application owned by the applicants (India Patent App No. 676/DELNP/2006).
India Examination Report dated Apr. 12, 2010 issued by the India Patent Office in one of Applicants' corresponding foreign applications.
India Office Action (Examination Report) dated Feb. 21, 2013, for applicant's India Patent Application No. 6688/DELNP/2007 corresponding to PCT/US2006/006422 filed Feb. 24, 2006.
India Office Action dated Dec. 31, 2014 from the India Patent Office for applicant's India application corresponding to PCT Application No. PCT/US2008/04708.
India Office Action dated Jul. 21, 2015 for National Phase of PCT/US2003/26424.
India Office Action dated Jul. 23, 2015 for National Phase of PCT/US2008/012440.
India Office Action dated Aug. 23, 2016, issued in Indian Patent Application No. 6834/DELNP/2009, which is the national phase of PCT/US2008/04708.
Israeli Office Action dated Apr. 10, 2013, from applicant's Israel Patent Application No. 185460 corresponding to PCT/US06/06422 filed Feb. 24, 2006, and its English translation.

(56) References Cited

OTHER PUBLICATIONS

Israeli Office Action dated Oct. 29, 2013, from Israel Patent Application No. 201438 that corresponds to PCT/US2008/004708, and its English translation.
Israeli Office Action and English Translation dated May 4, 2014 from applicant's Israel Patent Application No. 185460 corresponding to PCT/US06/06422 filed Feb. 24, 2006.
Israeli Office Action dated Feb. 1, 2015 for applicant's application corresponding to PCT Application No. PCT/US2003/026424.
Israeli Office Action dated Dec. 30, 2015, issued in Israeli Patent Application No. 216919, which corresponds to PCT/US2010/001794, and English translation.
Japanese Patent Office Action dated Jun. 2, 2009 and its English translation, cited in one of Assignee's Japanese Patent Application No. 2003-571422.
Japanese Patent Office Action dated Jun. 9, 2009 and its English translation, cited in one of Assignee's Japanese patent applications.
Japanese Decision of Rejection dated Jan. 12, 2010 and its English translation, corresponding to PCT/US2003/005521 corresponding to Diffusion's U.S. Pat. No. 7,351,844.
Japanese Office Action and its English Translation dated Jan. 12, 2010 in the Assignee's Japanese application relating to PCT/US2003/026424.
Japanese Office Action and its English Translation dated Apr. 6, 2010 in the Assignee's Japanese application relating to PCT/US2006/006422.
Japanese Notice of Reasons for Rejection and its English Translation dated May 24, 2011 issued in Japanese Patent Appln. No. 2007-557157 (corresponding to PCT/US2006/006422).
Japanese Office Action and its English Translation dated Oct. 4, 2011.
Japanese Office Action and its English Translation dated Jul. 10, 2012 for Applicant's Japanese Patent Application No. 2009-274988 corresponding to PCT/US2003/005521, filed Feb. 25, 2003.
Japanese Office Action and its English Translation dated Jul. 10, 2012 from Japanese Application No. 2009-279890 based on PCT/US2003/026424.
Japanese Office Action (Notice of Reasons For Rejection) dated Jan. 29, 2013, for applicant's Japanese Patent Application No. 2010-503069 corresponding to PCT/US08/004708 filed Apr. 11, 2008, and its English translation.
Japanese Patent Office Action dated Feb. 19, 2013, from applicant's Japanese Patent Application No. 2009-279890 corresponding to PCT/US03/26424 filed Aug. 25, 2003, and its English translation.
Japanese Decision of Rejection dated May 21, 2013, from applicant's Japanese Patent Application No. 2010-110185 corresponding to PCT/US2003/05521 filed Feb. 25, 2003, and its English translation.
Japanese Office Action (Notice of Reasons for Rejection) and its English translation dated Jun. 4, 2013, from applicant's Japanese Patent Application No. 2011-209754 corresponding to PCT/US06/06422 filed Feb. 24, 2006.
Japanese Office Action (Reasons For Rejection) dated Jun. 18, 2013, in Japanese App. No. 2010-531078 (No English translation).
Japanese Office Action (Final Rejection) and its English translation dated Sep. 10, 2013, from applicant's Japanese Application No. P2009-279890 corresponding to PCT/US03/26424 filed Aug. 25, 2003.
Japanese Office Action (Final Rejection) and its English translation dated Nov. 26, 2013, from applicant's Japanese Application No. P2010-503069 corresponding to PCT/US08/004708 filed Apr. 11, 2008.
Japanese Office Action (Final Rejection) and its English translation dated Feb. 4, 2014 from applicant's Japanese Application No. P2011-209754 corresponding to PCT/US06/06422 filed Feb. 24, 2006.
Japanese Office Action and its English translation dated Apr. 22, 2014 from applicant's Japanese Application No. P2010-531078 corresponding to PCT/US08/012440 filed Oct. 31, 2008.
Japanese Office Action dated Jun. 24, 2014 issued in Japanese Patent Application No. P2012-516071 and English Translation, 10 pp.
Japanese Office Action and its English translation dated Sep. 9, 2014 issued in Japanese Patent Application No. P2010-531078, 6 pp.
Japanese Office Action and English Translation dated Sep. 9, 2014 issued in Japanese Patent Application No. 2013-197629, 6 pp.
Japanese Office Action and English translation dated Sep. 24, 2014 issued in Japanese Patent Application No. P2011-209754, 5 pp.
Japanese Office Action dated Jan. 27, 2015 from the for applicant's application corresponding to PCT Application No. PCT/US03/26424.
Japanese Office Action and its English translation dated Apr. 14, 2015 for national phase of PCT/US2008/012440.
Japanese Office Action and its English translation dated Apr. 21, 2015 for national phase of PCT/US2008/04708.
Japanese Office Action and its English translation dated Apr. 21, 2015 for national phase of PCT/US2011/000997.
Japanese Official Action dated Sep. 8, 2015.
Japanese Final Rejection dated Nov. 24, 2015, issued in Japanese Patent Application No. P2013-513151, which corresponds to PCT/US2011/000997, and English translation.
Japanese Notice of Reasons for Rejection dated Nov. 24, 2015, issued in Japanese Patent Application No. P2015-011575, which corresponds to PCT/US2006/006422, and English translation.
Japanese Office Action dated Jan. 12, 2016, issued in Japanese Patent Application No. 2014-003614, which corresponds to PCT/US2003/026424.
Japanese Final Rejection dated Mar. 1, 2016, issued in Japanese Patent Application No. P2014-061897, which corresponds to PCT/US2008/004708, and English translation.
Japanese Notice of Reasons for Rejection dated Jun. 21, 2016, issued in Japanese Patent Application No. 2015-159872 and English translation.
Japanese Final Rejection dated Jun. 28, 2016, issued in Japanese Patent Application No. 2015-011575, which is the national phase of PCT/US2006/006422, and English translation.
Korean Office Action dated May 26, 2009, and English translation in a corresponding application owned by the applicants.
Korean Office Action dated Nov. 23, 2009 in applicant's corresponding Korean application No. 10-2006-7003827.
Korean Office Action and its English Translation dated Jun. 22, 2010 from Applicant's Korean Patent Appln. No. 10-2006-7003827, that corresponds to PCT/US2003/026424.
Korean Office Action and its English Translation dated Jul. 6, 2010 in the Assignee's Korean Application No. 10-2004-17013118, that is the Nationalized Appln. from PCT/US03/005521, claiming priority from U.S. Appl. No. 60/358,718.
Korean Patent Office Action dated Sep. 26, 2012, from Korean Patent Application No. 10-2007-7021197 based on PCT/US2006/006422, and its English translation.
Korean Office Action and English Translation dated Jul. 28, 2014 issued in Korean Patent Application No. 10-2009-7023432, 8 pp.
Korean Office Action dated Jan. 16, 2015 from the South Korea Patent Office for applicant's application corresponding to PCT Application No. PCT/US2008/012440.
Korean Office Action dated May 27, 2015 and its English translation for Application No. 10-2009-7023432 (national phase of PCT/US2008/04708).
Korean Notice of Preliminary Rejection dated Nov. 24, 2015, issued in Korean Application No. 10-2010-7010445, which corresponds to PCT/US2008/012440, and English translation.
Korean Notice of Preliminary Rejection dated Jul. 26, 2016, issued in South Korean Patent Application No. 10-2012-7001265, which is the national phase of PCT/US2010/001794, and English translation.
Mexican Office Action dated Feb. 23, 2009 in a corresponding application owned by the applicants in Mexican Patent Appln. No. PA/a/2004/008253.
Mexican Office Action dated May 2010, and its English translation of rejected parts of the Office Action, from Mexican Patent Application No. PA/a/2004/008253 corresponding to International Patent Application No. PCT/EP2003/005521.

(56) References Cited

OTHER PUBLICATIONS

Mexican Office Action and its English translation dated Oct. 20, 2011.
Mexican Office Action dated Aug. 27, 2012, corresponding to U.S. Appl. No. 12/081,236, filed Apr. 11, 2008 (No English Translation Available).
New Zealand Examination Report dated Jan. 8, 2008 from corresponding New Zealand Patent Office.
New Zealand Examination Report dated Oct. 6, 2008 issued by the New Zealand Patent Office in one of Applicants' corresponding foreign applications.
New Zealand Examination Report dated Jul. 2, 2009 issued by the New Zealand Patent Office in one of Applicants' corresponding foreign applications.
New Zealand Examination Report dated Apr. 7, 2010 issued by the New Zealand Patent Office in Applicants' corresponding foreign Application No. 584433.
New Zealand Examination Report dated Oct. 7, 2010 issued by the New Zealand Patent Office in one of Applicants' corresponding foreign applications.
New Zealand Examination Report dated Jan. 21, 2011.
New Zealand Examination Report dated Oct. 2011 issued by the New Zealand Patent Office in Applicants' corresponding foreign Application No. 595624.
Norwegian Office Action and its English Translation dated Jun. 22, 2010 in the Assignee's Norwegian application relating to PCT/US2003/005521.
Norwegian Office Action and its English Translation dated Feb. 16, 2011, from Norway Patent Application No. 20043661, based on International Patent Application No. PCT/US2008/012440.
Polish Office Action dated Feb. 23, 2010 from Polish Patent Application No. P-373780 based on PCT/US2003/005521.
Polish Office Action dated Sep. 2010 in corresponding Polish Application No. P-373780.
Ukraine Office Action dated Aug. 2010.
U.S. Final Office Action dated Dec. 4, 2008 from U.S. Appl. No. 11/361,054, 6 pages.
U.S. Non-Final Office Action dated Aug. 24, 2007, in U.S. Appl. No. 11/790,779, 6 pages.
U.S. Non-Final Office Action dated Sep. 28, 2007, in U.S. Appl. No. 11/723,383, 5 pages.
U.S. Non-Final Office Action dated Nov. 13, 2008, in U.S. Appl. No. 10/647,132, 7 pages.
U.S. Non-Final Office Action dated Oct. 28, 2009, in U.S. Appl. No. 11/361,054, 5 pages.
U.S. Non-Final Office Action dated Sep. 22, 2011, in U.S. Appl. No. 11/790,779, 8 pages.
U.S. Non-Final Office Action dated Dec. 19, 2011 in U.S. Appl. No. 12/801,726, 7 pages.
U.S. Non-Final Office Action dated Jan. 4, 2012 in U.S. Appl. No. 13/137,337, 5 pages.
U.S. Non-Final Office Action dated Jan. 24, 2012 in U.S. Appl. No. 13/137,322, 9 pages.
U.S. Non-Final Office Action dated Mar. 16, 2012 in U.S. Appl. No. 13/137,324, 5 pages.
U.S. Non-Final Office Action dated May 10, 2012 in U.S. Appl. No. 13/067,469, 17 pages.
U.S. Final Office Action dated Jul. 26, 2012 in U.S. Appl. No. 12/801,726, 6 pages.
U.S. Non-Final Office Action dated Sep. 6, 2012 in U.S. Appl. No. 13/137,322, 9 pages.
U.S. Final Office Action dated Sep. 18, 2012 in U.S. Appl. No. 13/137,337, 5 pages.
U.S. Final Office Action dated Dec. 24, 2012 in U.S. Appl. No. 13/137,324, 10 pages.
U.S. Final Office Action dated Jan. 15, 2013 from U.S. Appl. No. 13/067,469, 21 pages.
U.S. Final Office Action dated Apr. 5, 2013 from U.S. Appl. No. 13/137,322, 10 pages.
U.S. Final Office Action dated Jun. 12, 2013 from U.S. Appl. No. 12/801,726, 6 pages.
U.S. Advisory Office Action dated Jul. 16, 2013 in U.S. Appl. No. 13/137,324, 7 pages.
U.S. Non-Final Office Action dated Jul. 29, 2013 from U.S. Appl. No. 13/067,469, 21 pages.
U.S. Non-Final Office Action dated Aug. 22, 2013 from U.S. Appl. No. 13/507,365, 6 pages.
U.S. Final Office Action dated Nov. 20, 2013 in U.S. Appl. No. 13/137,337, 5 pages.
U.S. Non-Final Office Action dated Dec. 6, 2013 from U.S. Appl. No. 13/137,322, 8 pages.
U.S. Non-Final Office Action dated Jan. 30, 2014 from U.S. Appl. No. 12/801,726, 5 pages.
U.S. Final Office Action dated May 8, 2014 from U.S. Appl. No. 13/507,365, 5 pages.
U.S. Non-Final Office Action dated Jun. 5, 2014 from U.S. Appl. No. 13/067,469, 26 pages, Gainer.
U.S. Non-Final Office Action dated Jun. 9, 2014 from U.S. Appl. No. 13/137,324, 7 pages, Gainer et al.
U.S. Non-Final Office Action dated Jun. 26, 2014 in U.S. Appl. No. 13/137,337, 5 pages.
U.S. Final Office Action dated Sep. 8, 2014 issued in U.S. Appl. No. 12/801,726, 23 pages.
U.S. Non-Final Office Action dated Oct. 1, 2014 issued in U.S. Appl. No. 13/621,650, 51 pages.
U.S. Final Office Action dated Nov. 25, 2014 in U.S. Appl. No. 13/067,469, 13 pages.
U.S. Non-Final Office Action dated Dec. 8, 2014 in U.S. Appl. No. 13/137,324, 11 pages.
U.S. Non-Final Office Action dated Dec. 29, 2014 in U.S. Appl. No. 13/507,365, 5 pages.
U.S. Non-Final Office Action dated Apr. 29, 2015, in U.S. Appl. No. 12/801,726, 6 pages.
U.S. Final Office Action dated Jun. 4, 2015 for U.S. Appl. No. 13/621,650, 6 pages.
U.S. Final Office Action dated Jul. 9, 2015 for U.S. Appl. No. 13/137,324, 6 pages.
U.S. Final Office Action dated Aug. 13, 2015 for U.S. Appl. No. 13/507,365, 5 pages.
U.S. Non-Final Office Action dated Sep. 30, 2015 in U.S. Appl. No. 13/137,337, 4 pages.
U.S. Final Office Action dated Nov. 12, 2015 for U.S. Appl. No. 12/801,726, 6 pages.
U.S. Non-Final Office Action dated Mar. 16, 2016 for U.S. Appl. No. 13/507,365, 4 pages.
U.S. Non-Final Office Action dated May 5, 2016, issued in U.S. Appl. No. 12/801,726, which corresponds to PCT/US2010/001794, 6 pages.
U.S. Non-Final Office Action dated Oct. 12, 2016, issued in U.S. Appl. No. 14/642,703, which corresponds to PCT/US2011/000997, 15 pages.
U.S. Final Office Action dated Nov. 14, 2016, issued in U.S. Appl. No. 12/801,726, which corresponds to PCT/US2010/001794, 11 pages.
Bazan, N. et al., "Hypoxia Signaling to Genes," Molecular Neurobiology, vol. 26, Nos. 2-3, pp. 283-298, (2002).
Gainer, J.L. et al., "Trans Sodium Crocetinate with Temozolomide and Radiation Therapy for Glioblastoma Multiforme," J Neurosurg, vol. 126, pp. 460-466, (2017), Published online May 13, 2016; doi: 10.3171/2016.3.JNS152693.
Mohler III, E.R., et al., "Evaluation of Trans Sodium Crocetinate on Safety and Exercise Performance in Patients with Peripheral Artery Disease and Intermittent Claudication," NIH Public Access, Author Manuscript, available in PMC 2014, 14 pages, doi: 10.1177/1358863X11422742, face of article states: Published in final edited form as: *Vasc Med*. Oct. 2011; 16(5), 346-353.
Murray, R., "Pharmacokinetics of TSC and the Treatment of Hypoxic States," A Dissertation Presented to the Faculty of the School of Engineering and Applied Science, University of Virginia, 106 pages, retrieved on Sep. 5, 2019, from: https://media.proquest.com/media/pq/classic/doc/888859001/fmt/ai/rep/SPDF?_s=eOSFva3r5jHJaP4%2FUSCxt3i9uLU%3D.

(56) References Cited

OTHER PUBLICATIONS

Stennett, A., "Mechanism of Action of TSC," A Dissertation Presented to the Faculty of the School of Engineering and Applied Science, University of Virginia, 191 pages, retrieved on Sep. 5, 2019, from: https://media.proquest.com/media/pq/classic/doc/888858991/fmt/ai/rep/SPDF?_s=RXVfuP3SH6vxf1TE4SVMciZ8bfc%3D.

Stennett, A. et al., "*Trans*-Sodium Crocetinate and Hemorrhagic Shock," Shock, vol. 28, No. 3, pp. 339-344, (2007).

Clinical Trials.gov, "Trans Sodium Crocetinate (TSC) Study of Intra-tumoral Oxygen Concentration, Safety, and Pharmacokinetics in Patients With High Grade Glioma," ClinicalTrials.gov Identifier: NCT00826930, 7 pages, retrieved on Nov. 27, 2019, from: https://clinicaltrials.gov/ct2/show/NCT00826930.

Clinicaltrials.Gov, "Safety and Efficacy of Trans Sodium Crocetinate (TSC) With Radiation and Temozolomide in Newly Diagnosed Glioblastoma," ClinicalTrials.gov Identifier: NCT01465347, 9 pages, retrieved on Nov. 27, 2019, from: https://clinicaltrials.gov/ct2/show/NCT01465347.

English abstract for JP 2002-348275 A from the European Patent Office website, 1 page, retrieved on May 27, 2020, from: https://worldwide.espacenet.com/publicationDetails/biblio?DB=EPODOC&II=0&ND=3&adjacent=true&locale=en_EP&FT=D&date=20021204&CC=JP&NR=2002348275A&KC=A#.

Feng, G. et al., "Study on the Inclusion Complexation Interaction of Beta-cyclodextrin and Beta-carotene by UV-Vis Spectra," 1 page, Abstract only for Guang Pu Xue Yu Guang Pu Fen Xi, vol. 24, No. 9, pp. 1099-1102, (2004), https://pubmed.ncbi.nlm.nih.gov/15762533/.

Manabe, H. et al., "Metabolic Reflow as a Therapy for Ischemic Brain Injury," Acta Neurochirurgica Suppiementum, vol. 110/2, pp. 87-91, (2011).

Manabe, H. et al., "Protection Against Focal Ischemic Injury to the Brain by Trans-Sodium Crocetinate: Laboratory Investigation," NIH Public Access, Author Manuscript, available in PMC 2012, 18 pages, doi: 10.3171/2009.10.JNS09562, face of article states: Published in final edited form as: *J Neurosurg*. Oct. 2010; 113(4): 802-809.

Redenti, E., et al., "Cyclodextrin Complexes of Salts of Acidic Drugs. Thermodynamic Properties, Structural Features, and Pharmaceutical Applications," Journal of Pharmaceutical Sciences, vol. 90, No. 8, pp. 979-986, (2001).

Wang, L. et al., "UV-vis Spectroscopic Characterization of Inclusion Compounds of Beta-cyclodextrin with Lycopene," 1 page, Abstract only for Guang Pu Xue Yu Guang Pu Fen Xi, vol. 24, No. 2, pp. 183-186, (2004), https://pubmed.ncbi.nlm.nih.gov/15769012/.

Wang, Y. et al., "Perihematomal Cellular Injury Is Reduced by Trans-Sodium Crocetinate in a Model of Intracerebral Hemorrhage," Molecular Neurobiology, vol. 52, pp. 985-989, (2015).

Wang, Y. et al., "Trans-Sodium Crocetinate Improves Outcomes in Rodent Models of Occlusive and Hemorrhagic Stroke," NIH Public Access, Author Manuscript, available in PMC 2015, 18 pages, face of article states: *Brain Res*. Oct. 2, 2014; 1583: 245-254, doi: 10.1016/j.brainres.2014.08.013.

Beauchesne, P. et al., "Prolonged Survival for Patients with Newly Diagnosed, Inoperable Glioblastoma with 3-Times Daily Ultrafractionated Radiation Therapy," Neuro-Oncology, vol. 12, No. 6, pp. 595-602, (2010).

Hepple, R. et al., "No Effect of Trans Sodium Crocetinate on Maximal $O_2$ Conductance or $V_{O2,max}$ in Moderate Hypoxia," Respiratory Physiology & Neurobiology, vol. 134, pp. 239-246, (2003).

Kole, A. et al., "Concurrent Chemoradiotherapy Versus Radiotherapy Alone for 'Biopsy-Only' Glioblastoma Multiforme," Cancer, vol. 122, pp. 2364-2370, (2016).

Sheehan, J. et al., "Use of Trans Sodium Crocetinate for Sensitizing Glioblastoma Multiforme to Radiation," J Neurosurg., vol. 108, pp. 972-978, (2008).

Sheehan, J. et al., "Effect of Trans Sodium Crocetinate on Brain Tumor Oxygenation: Laboratory Investigation," J Neurosurg., vol. 111, pp. 226-229, (2009).

Sheehan, J. et al., "Trans-sodium Crocetinate Enhancing Survival and Glioma Response on Magnetic Resonance Imaging to Radiation and Temozolomide: Laboratory Investigation," J Neurosurg., vol. 113, pp. 234-239, (2010).

Sheehan, J. et al., "Trans Sodium Crocetinate: Functional Neuroimaging Studies in a Hypoxic Brain Tumor: Laboratory Investigation," J Neurosurg., vol. 115, pp. 749-753, (2011).

Stupp, R. et al., "Radiotherapy plus Concomitant and Adjuvant Temozolomide for Glioblastoma," N Engl J Med, vol. 352, pp. 987-996, (2005).

Stupp, R. et al., Supplmentary Appendix to: "Radiotherapy plus Concomitant and Adjuvant Temozolomide for Glioblastoma," N Engl J Med, vol. 352, pp. 987-996, (2005), 4 pages, retrieved on Aug. 6, 2020, from: https://www.nejm.org/doi/suppl/10.1056/NEJMoa043330/suppl_file/987sa1.pdf.

Stupp, R. et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," Lancet Oncol, vol. 10, pp. 459-466, (2009).

Wagner, P. et al., "Effects of Crocetin on Pulmonary Gas Exchange in Foxhounds During Hypoxic Exercise," J Appl Physiol, vol. 89, pp. 235-241, (2000).

\* cited by examiner

TRANS CAROTENOIDS, THEIR SYNTHESIS, FORMULATION AND USES

This application is a continuation application of U.S. patent application Ser. No. 14/993,047, filed on Jan. 11, 2016, which is a divisional application of U.S. patent application Ser. No. 13/137,324, filed on Aug. 5, 2011, which is a divisional application of U.S. patent application Ser. No. 11/361,054, filed Feb. 24, 2006, now U.S. Pat. No. 8,030,350, which claims the benefit of Provisional Application No. 60/655,422, filed Feb. 24, 2005, the entire contents of which are hereby incorporated by reference in this application.

This invention was made with Government support under Contract No. N00014-04-C-0146 awarded by the Office of Naval Research. The Government has certain rights in the invention.

Included in this invention are improved chemical synthesis methods for making trans carotenoids, bipolar trans carotenoids (BTC) including bipolar trans carotenoid salts (BTCS) such as trans sodium crocetinate (TSC), the compounds themselves, methods of formulating them, administering them and methods of using them.

BACKGROUND OF THE INVENTION

Carotenoids are a class of hydrocarbons consisting of isoprenoid units joined in such a manner that their arrangement is reversed at the center of the molecule. The backbone (skeleton) of the molecule consists of conjugated carbon-carbon double and single bonds, and can also have pendant groups. Although it was once thought that the skeleton of a carotenoid contained 40 carbons, it has been long recognized that carotenoids can also have carbon skeletons containing fewer than 40 carbon atoms. The 4 single bonds that surround a carbon-carbon double bond all lie in the same plane. If the pendant groups are on the same side of the carbon-carbon double bond, the groups are designated as cis; if they are on opposite sides of the carbon-carbon bond, they are designated as trans. Because of the large number of double bonds, there are extensive possibilities for geometrical (cis/trans) isomerism of carotenoids, and isomerization occurs readily in solution. A series of books which is an excellent reference to many of the properties, etc. of carotenoids ("Carotenoids", edited by G. Britton, S. Liaaen-Jensen and H. Pfander, Birkhauser Verlag, Basel, 1995 hereby incorporated by reference in its entirety).

Many carotenoids are nonpolar and, thus, are insoluble in water. These compounds are extremely hydrophobic which makes their formulation for biological uses difficult because, in order to solubilize them, one must use an organic solvent rather than an aqueous solvent. Other carotenoids are monopolar, and have characteristics of surfactants (a hydrophobic portion and a hydrophilic polar group). As such, these compounds are attracted to the surface of an aqueous solution rather than dissolving in the bulk liquid. A few natural bipolar carotenoid compounds exist, and these compounds contain a central hydrophobic portion as well as two polar groups, one on each end of the molecule. It has been reported ("Carotenoids", Vol. 1A, p. 283) that carotenoid sulphates have "significant solubility in water of up to 0.4 mg/ml". Other carotenoids that might be thought of as bipolar are also not very soluble in water. These include dialdehydes and diketones. A di-pyridine salt of crocetin has also been reported, but its solubility in water is less than 1 mg/ml at room temperature. Other examples of bipolar carotenoids are crocetin and crocin (both found in the spice saffron). However, crocetin is only sparingly soluble in water. In fact, of all of the natural bipolar carotenoids, only crocin displays significant solubility in water.

U.S. Pat. Nos. 4,176,179; 4,070,460; 4,046,880; 4,038,144; 4,009,270; 3,975,519; 3,965,261; 3,853,933; and 3,788,468 (each of which is hereby incorporated by reference in its entirety) relate to various uses of crocetin.

U.S. Pat. No. 6,060,511, relates to trans sodium crocetinate (TSC) and its uses. The TSC is made by reacting naturally occurring saffron with sodium hydroxide followed by extractions. The '511 patent covers an extraction method for making a bipolar trans carotenoid salt (Trans Sodium Crocetinate), a purified composition obtained from extraction, and various uses of the composition such as improving oxygen diffusivity and treatment of hemorrhagic shock.

PCT Application US03/05521 relates to the chemical synthesis method for making bipolar trans carotenoid salts, and methods of using them.

The information below shows the last few steps of a chemical synthesis process for TSC described in PCT Application US03/05521.

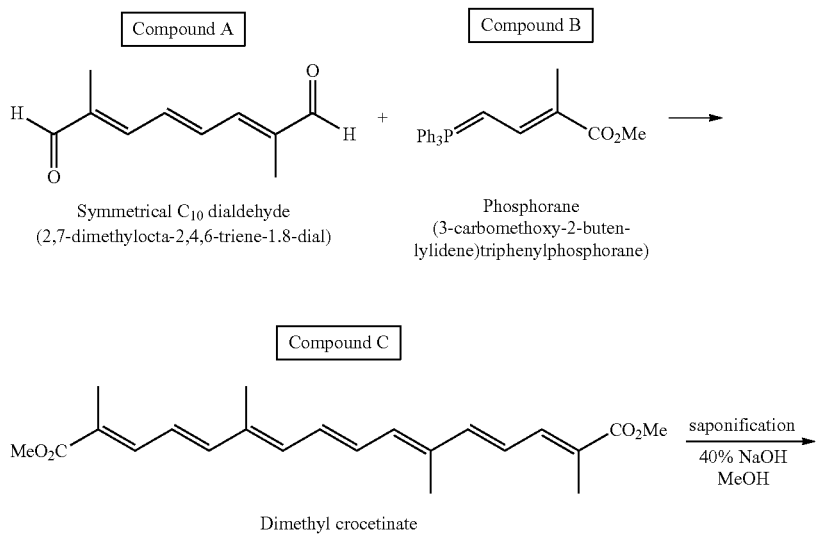

Final Product
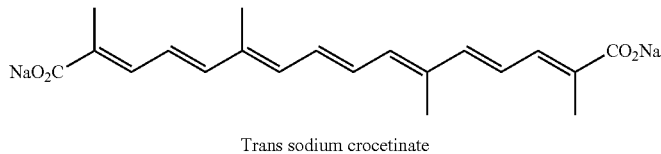
Trans sodium crocetinate
The complete synthesis procedure for TSC, as described in the PCT application, arrived at key intermediates, "Compound A" and "Compound B" via multi-step synthetic processes shown in the two sets of information below:
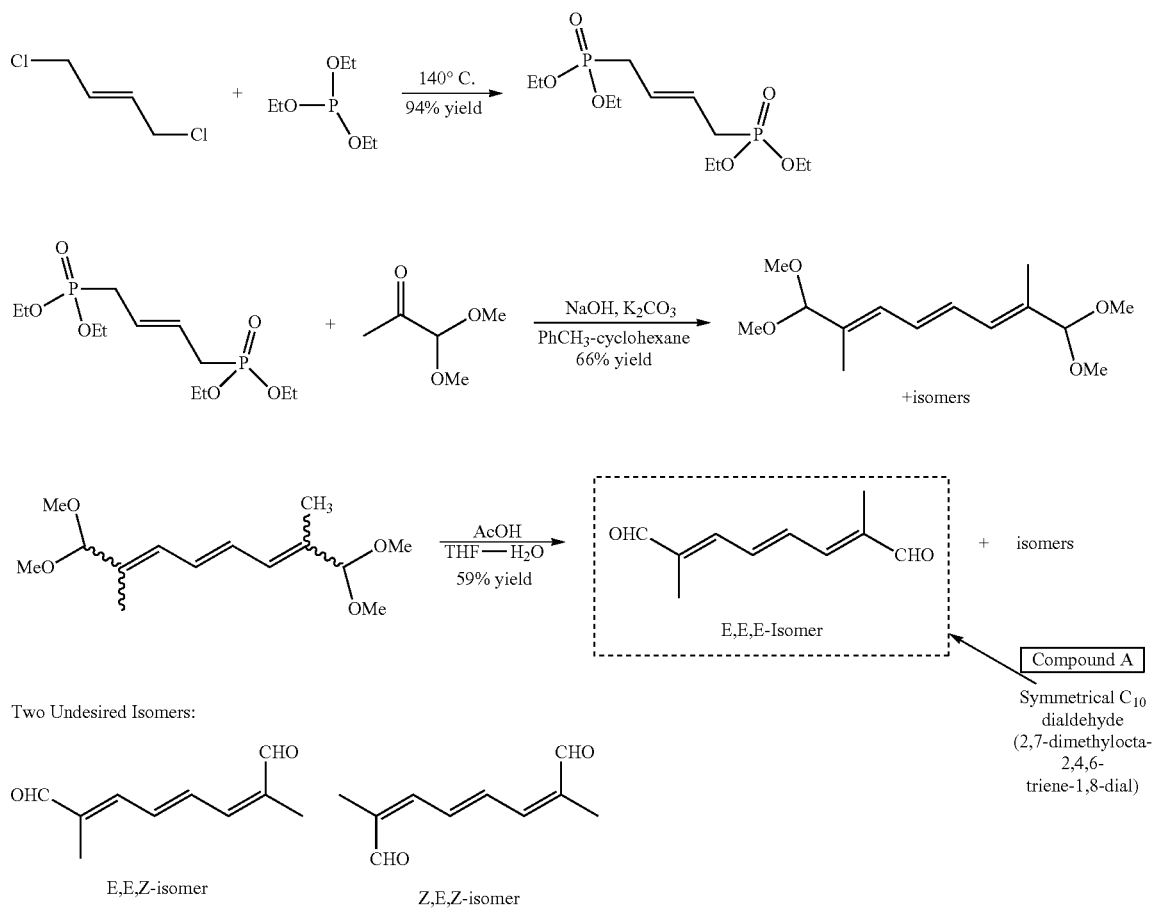
Two Undesired Isomers:
Isomerization of Undesired to Desired Dialdehyde:
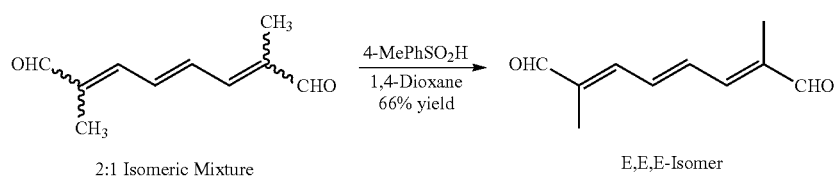
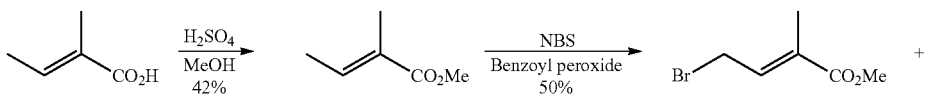

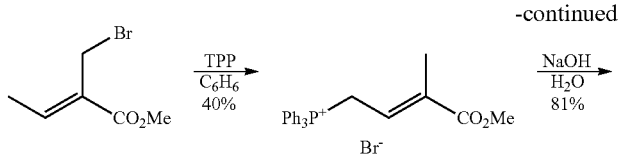
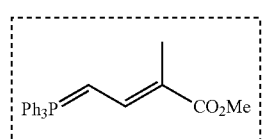

-continued

Phosphorane
(3-carbomethoxy-2-buten-1-ylidene)triphenylphosphorane

A common form of therapy for malignant tumors, or cancer, is irradiation. The radiation administered is in the form of electromagnetic waves or charged or neutral particles. Electromagnetic waves are represented by x-rays or gamma rays. Charged particles take the form of electrons, protons, or heavy ions, while neutrons are an example of neutral particles. During a course of therapy, the radiation may be administered by external beam, an interstitial implant, or a combination of the two. With irradiation, the rad and Gray are the usual units of measure. A dose of one rad for any type of radiation results in the absorption of 100 ergs of energy per gram of target tissue, and one Gray is equal to 100 rads. Therefore, one centiGray (cGy) is equivalent to one rad. For the majority of smaller tumors of the head and neck, a course of radiotherapy consisting of 6000 to 6500 cGy over 6 to 6.5 weeks is usually adequate. Doses of 6500 to 7000 cGy over 6.5 to 7.5 weeks may be necessary to control larger masses with even higher doses required for bulky disease. It has been shown that a dose of 5000 cGy over 5 weeks will control subclinical disease in 90 to 95% of patients.

A viable tumor cell is one in which the capacity for unlimited division is present. A tumor cell must lose this reproductive capability to be considered killed. Radiotherapeutic tumor control is achieved by the elimination of all viable cells within a tumor, and a given dose of radiation will result in the death of a certain proportion (not number) of viable cells with each administration. Therefore, the larger the volume of tumor, the larger the total dose of radiation required for tumor control. A tumor cell which has been sterilized or killed with radiotherapy may not necessarily have been morphologically altered and typically manifests cell death at the time of mitosis (cell division). It is important to note that this death may not occur with the first cell division following irradiation. Several apparently successful cell cycles may take place before cell death becomes overtly manifest, but the cell is still considered no longer viable in that its unlimited reproductive potential has already been lost.

The radiosensitivity of tumor cells is influenced by many factors. Not long ago, tumor histology and location were thought to play major roles in the potential control of tumors with radiotherapy. There is no doubt that certain tumors are more difficult to control with radiotherapy, but histology is no longer felt to be as important. The number of viable tumor cells and the proportion of hypoxic (lacking oxygen) cells within a tumor are major contributors to radiosensitivity, and both of these are a function of the size of a given tumor.

It has been apparent for many years that oxygen plays an important role in tumor sensitivity to radiation therapy. That hypoxic tumor cells are more radioresistant is well-established. While the mechanism for this phenomenon is incompletely understood, the presence of oxygen is thought to fix radiation injury within cells which is labile and would otherwise have been repaired. The maximum change in radiosensitivity occurs over the range of 0-20 mm of Hg, a value which is well below the venous oxygen tension. Significant hypoxia has been demonstrated in experimental solid tumors, and significant indirect evidence indicates hypoxic conditions within human tumors as well. Hypoxic conditions may develop because tumors often outgrow their existing blood supply.

Chemotherapy is another method used to treat cancer. Drugs are administered, such carmustine (BCNU), temozolamide (TMZ), cisplatin, methotrexate, etc., and these drugs will result in the eventual death or non-growth of the tumor cells. It has been noted that chemotherapy, like radiation therapy, is less successful with hypoxic cells—which frequently occur in tumors.

High blood pressure, or hypertension, affects about one in four Americans. This potentially life-threatening condition can exist virtually without symptoms. Blood pressure is characterized by two values: the systolic blood pressure and the diastolic blood pressure. Hypertension is generally defined at a systolic pressure above 140 mm Hg or a diastolic pressure greater than 90 mm Hg; however, these definitions change and some physicians feel that blood pressure should remain at 120/70 all one's life, either naturally or with the use of antihypertensive medicine.

In some people, the system that regulates blood pressure goes awry: arterioles throughout the body stay constricted, driving up the pressure in the larger blood vessels. Sustained high blood pressure—above 140/90 mm Hg, according to most experts—is called hypertension. About 90 percent of all people with high blood pressure have what is currently called "essential" hypertension—which is meant to denote that it has no identifiable cause. In the remaining 10 percent of cases, the elevated blood pressure is due to kidney disease, diabetes, or another underlying disorder.

SUMMARY OF THE INVENTION

The invention relates to a variety of novel trans carotenoid compounds, as well as many compositions containing a trans carotenoid compound including compositions comprising a trans carotenoid and a cyclodextrin.

The invention also includes a method of synthesizing carotenoid compounds having the formula:

where:
- Y=H or a cation other than H
- Z=a polar group which is associated with Y, and
- TCRO=symmetric or asymmetric trans carotenoid skeleton, comprising the steps of: coupling a dialdehyde containing conjugated carbon-carbon double bonds with a Wittig agent, and optionally saponifying the product of the coupling step.

In other embodiments, the invention relates to a method of treating a tumor in a mammal comprising administering to the mammal i) a trans carotenoid, and ii) radiation or chemotherapy, as well as methods for treating hypertension, ventricular fibrillations or tachycardia, or high lipids in a mammal, comprising administering to the mammal in need of treatment an effective amount of a trans carotenoid.

DETAILED DESCRIPTION OF THE INVENTION

Figure 1:
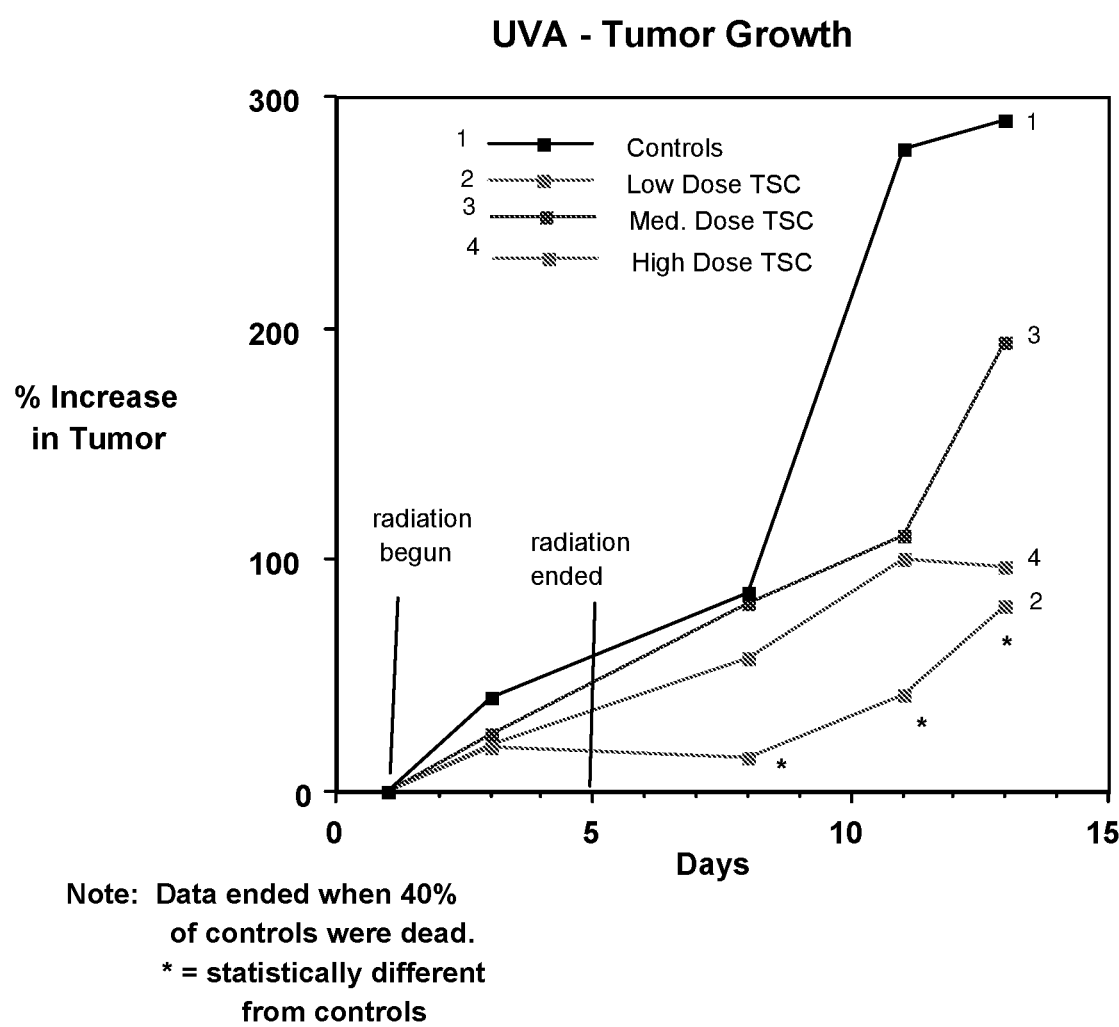
FIG. 1 is Study A Results of Tumor Growth.

The invention relates to an improved chemical synthesis method for making trans carotenoids, bipolar trans carotenoids (BTC), bipolar trans carotenoid salts (BTCS) including trans sodium crocetinate (TSC), the compounds themselves, methods of formulating them, and methods of using them. As used herein, the term "bipolar" means having two polar groups, one at each end of the molecule.

The new method of synthesis invention, described herewith, is an improvement of the synthetic process described above, i.e. in U.S. application Ser. No. 10/647,132, hereby incorporated by reference in its entirety. In the subject invention, Compound B is substituted with Compound D. The resulting synthesis proceeds to the Final Product (e.g. trans sodium crocetinate) via a new penultimate intermediate, Compound E (shown in the following information).

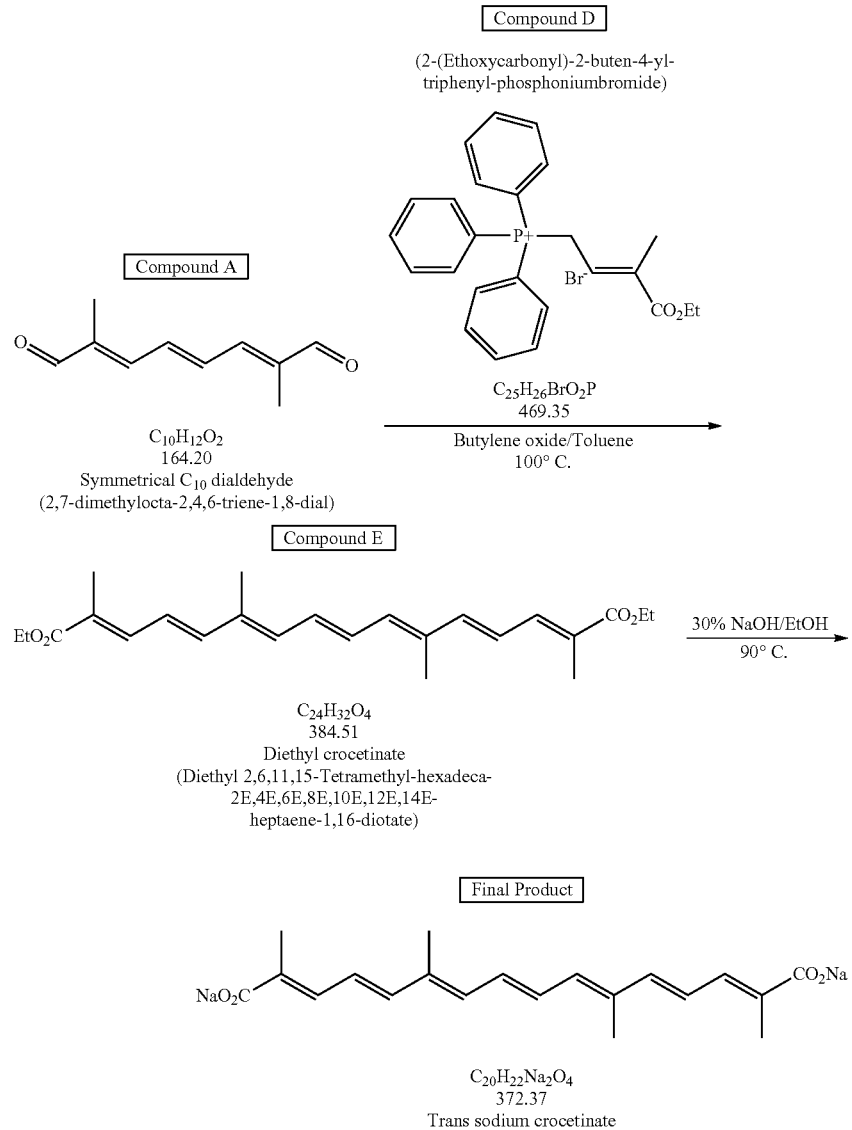

In the new, improved synthetic method, Compound A (2,7-dimethylocta-2,4,6-triene-1,8-dial) is combined with Compound D (2-(Ethoxycarbonyl)-2-buten-4-yl-triphenyl-phosphoniumbromide), a C5 Wittig ester halogenide. These two react to form diethyl crocetinate or Compound E (Diethyl 2,6,11,15-Tetramethyl-hexadeca-2E,4E,6E,8E,10E,12E,14E-heptaene-1,16-diotate). Compound E is then saponified (via the use of sodium hydroxide/ethanol) to form the final, desired product, trans sodium crocetinate.

Compounds of the Invention

The subject invention relates to trans carotenoids including trans carotenoid diesters, dialcohols, diketones and diacids, bipolar trans carotenoids (BTC), and bipolar trans carotenoid salts (BTCS) compounds and synthesis of such compounds having the structure:

YZ-TCRO-ZY where:
- Y (which can be the same or different at the two ends)=H or a cation other than H, preferably $Na^+$ or $K^+$ or $Li^+$. Y is advantageously a monovalent metal ion. Y can also be an organic cation, e.g., $R_4N^+$, $R_3S^+$, where R is H, or $C_nH_{2n+1}$ where n is 1-10, advantageously 1-6. For example, R can be methyl, ethyl, propyl or butyl.
- Z (which can be the same or different at the two ends)=polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $CnH_{2n+1}$.
- TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group ($CH_3$), an ethyl group ($C_2H_5$), a phenyl or single aromatic ring structure with or without pendant groups from the ring, a halogen-containing alkyl group (C1-C10) such as $CH_2Cl$, or a halogen such as Cl or Br or a methoxy ($OCH_3$) or ethoxy ($OCH_2CH_3$). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbence of the highest peak which occurs in the visible wave length range of 380 to 470 nm (the number depending on the solvent used and the chain length of the BTC or BTCS. The addition of pendant groups or differing chain lengths will change this peak absorbance but someone skilled in the art will recognize the existence of an absorbance peak in the visible range corresponding to the conjugated backbone structure of these molecules.) is divided by the absorbency of the peak which occurs in the UV wave length range of 220 to 300 nm can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis, using a cuvette designed for UV and visible wavelength ranges, on the trans sodium salt of crocetin of commonly owned U.S. Pat. No. 6,060,511 (TSC made by reacting naturally occurring saffron with sodium hydroxide followed by extractions which selected primarily for the trans isomer), the value obtained averages about 6.8. Performing that test on the synthetic TSC of the subject invention, that ratio is greater than 7.0 (e.g. 7.0 to 8.5), advantageously greater than 7.5 (e.g. 7.5-8.5), most advantageously greater than 8. The synthesized material is a "purer" or highly purified trans isomer.

Asymmetric Compounds

Some examples of asymmetric compounds include but are not limited to the following:

1) From Example 6—Synthesis of Compound P

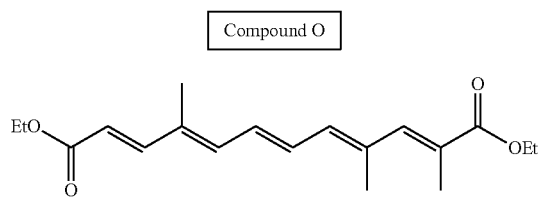

$C_{19}H_{26}O_4$
318.41

(Diethyl 2,4,9-Trimethyl-dodeca-2E,4E,6E,8E,10E-pentaene-1,12-diotate)

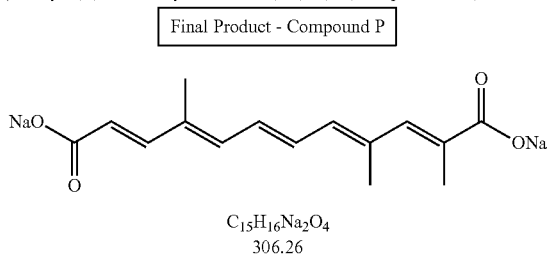

$C_{15}H_{16}Na_2O_4$
306.26

(Disodium 2,4,9-Trimethyldodeca-2E,4E,6E,8E,10Epentaene-1,12-diotate)

2) From Example 8—Synthesis of Compound U

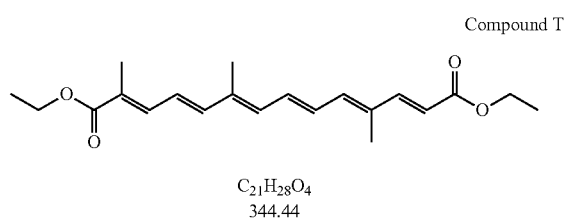

$C_{21}H_{28}O_4$
344.44

(Diethyl 2,6,11-Trimethyl-tetradeca-2E,4E,6E,8E,10E,12E-hexaene-1,14-diotate)

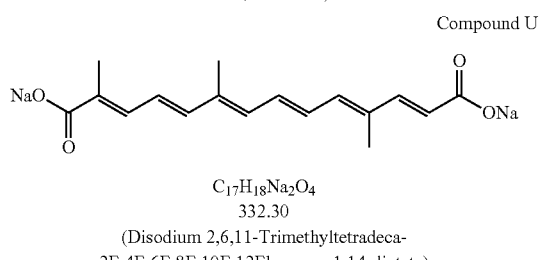

$C_{17}H_{18}Na_2O_4$
332.30

(Disodium 2,6,11-Trimethyltetradeca-2E,4E,6E,8E,10E,12Ehexaene-1,14-diotate)

3) From Example 9—Synthesis of Compound W

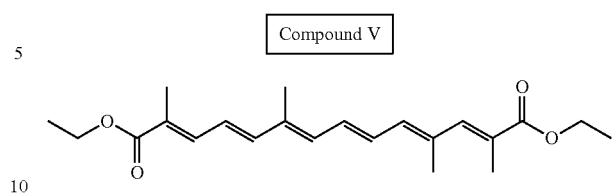

$C_{22}H_{30}O_4$
358.47

(Diethyl 2,4,9,13-Tetramethyl-tetradeca-2E,4E,6E,8E,10E,12E-hexane-1,14-diotate)

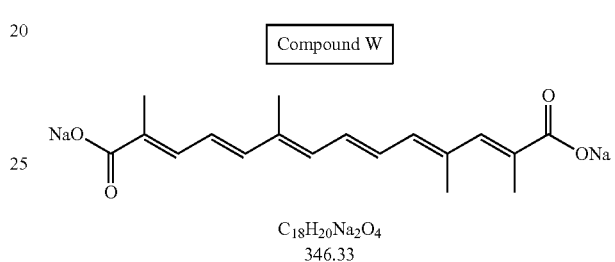

$C_{18}H_{20}Na_2O_4$
346.33

Disodium 2,4,9,13-Tetramethyltetradeca-2E,4E,6E,8E,10E,12Ehexaene-1,14-diotate)

Those skilled in the art will recognize that asymmetry can be achieved by spatial placement of pendant groups along the length of the TCRO chain, or by varying the type of pendant group on each side of the molecule or both. In addition, as in the case of symmetric trans carotenoid molecules, asymmetric trans carotenoid molecules can have varying cations, polar end groups and chain lengths.

Intermediate Compounds

In making carotenoid compounds and their salts, certain intermediate compounds are synthesized prior to obtaining the final product.

For example, in the synthesis for TSC, key intermediates after the coupling of Compounds A and D in the method of the subject invention are shown below. First is diethyl crocetinate. Dimethyl crocetinate can also be substituted for diethyl crocetinate, as can dipropyl etc. forms of the compound. The structures of some of these intermediates (for a number of the BTCS molecules presented in examples herein) are shown following:

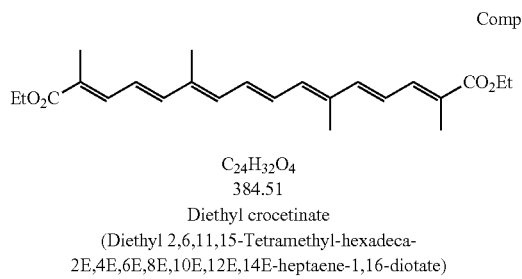

$C_{24}H_{32}O_4$
384.51
Diethyl crocetinate
(Diethyl 2,6,11,15-Tetramethyl-hexadeca-2E,4E,6E,8E,10E,12E,14E-heptaene-1,16-diotate)

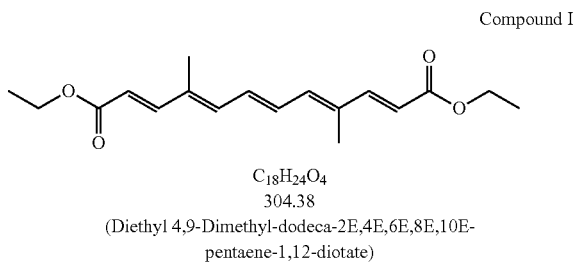

$C_{18}H_{24}O_4$
304.38
(Diethyl 4,9-Dimethyl-dodeca-2E,4E,6E,8E,10E-pentaene-1,12-diotate)

-continued

Compound O

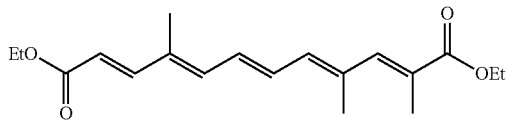

C$_{19}$H$_{26}$O$_4$
318.41
(Diethyl 2,4,9-Trimethyl-dodeca-2E,4E,6E,8E,10E-pentaene-1,12-diotate)

Compound Q

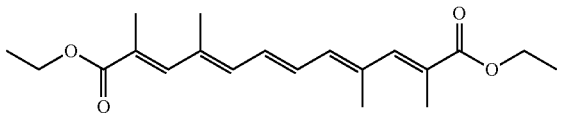

C$_{20}$H$_{28}$O$_4$
332.43
(Diethyl 2,4,9,11-Tetramethyl-dodedeca-2E,4E,6E,8E,10E-pentaene-1,12-diotate)

Compound T

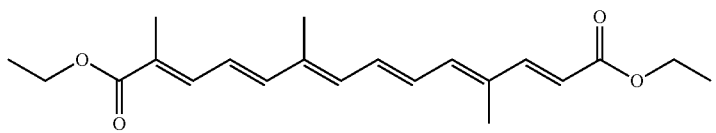

C$_{21}$H$_{28}$O$_4$
344.44
(Diethyl 2,6,11-Trimethyl-tetradeca-2E,4E,6E,8E,10E,12E-hexaene-1,14-diotate)

Compound V

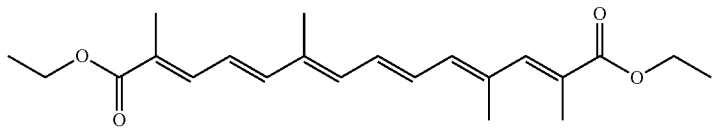

C$_{22}$H$_{30}$O$_4$
358.47
(Diethyl 2,4,9,13-Tetramethyl-tetradeca-2E,4E,6E,8E,10E,12E-hexaene-1,14-diotate)

Compound Z

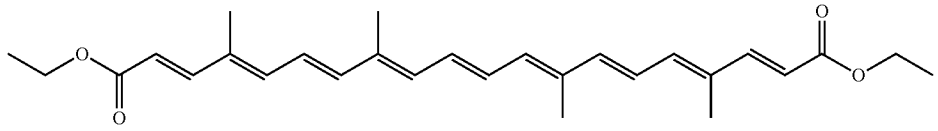

C$_{28}$H$_{36}$O$_4$
436.58
(Diethyl 4,8,13,17-Tetramethyl-eicosa-2E,4E,6E,8E,10E,12E,14E,16E,18E-nonaene-1,10-diotate)

Compound BB

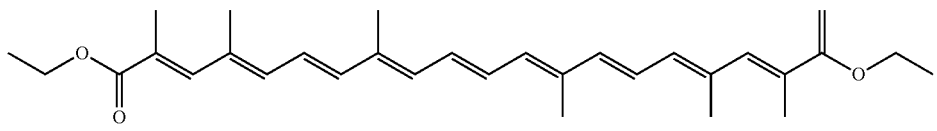

C$_{30}$H$_{40}$O$_4$
464.64
(Diethyl 2,4,8,13,17,19-Hexamethyl-eicosa-2E,4E,6E,8E,10E,12E,14E,16E,18E-nonaene-1,10-diotate)

Synthesis of the Compounds of the Invention

One embodiment of the subject invention relates to improvements made to the last few steps of the process described in commonly owned PCT Application US03/05521 and U.S. application Ser. No. 10/647,132. In the new invention, a C10 dial (shown previously as Compound A) or a C20 dial for the synthesis of long chain carotenoids, is reacted with a Wittig salt (C2, C3, C5, C10, C15 or other) through either a single or double step coupling reaction to form either a single intermediate or two intermediates (one from each coupling step). The final intermediate is then saponified to form the BTCS of desired chain length, symmetry and salt type.

Specifically, in the synthesis of TSC (described in detail in Examples 1 and 2 herein), the invention relates to the coupling reaction involving Compounds A and Compound D (rather than Compound B) resulting in the production of a penultimate intermediate, Compound E. Compound E is then converted to TSC via a saponification reaction with sodium hydroxide. In the invention, the TSC product that is formed is at a higher yield and purity (compositional and isomeric) than described in the previous commonly owned application.

Improvements to the Synthesis of Carotenoids Such as Trans Sodium Crocetinate (TSC) Resulting in Higher Yield and Purity:

1) Butylene Oxide Solvent for Reaction System

In the subject invention, the coupling reaction of Compounds A and D took place in a butylene oxide solvent system. Butylene oxide/toluene was used as the reaction vehicle for the coupling. The yield for this step was routinely between 55-60%. By comparison, a synthesis described in PCT Application US03/05521 used benzene as the vehicle for the analogous coupling reaction (between Compounds A and B) with a yield at this step of 33%.

Butylene oxide was used as the solvent in this coupling reaction because it is a pH-neutral solvent system for the Wittig reaction. A pH-neutral system is advantageous because 1) there is no salt generation in a pH-neutral environment, 2) alcohol species production is inhibited or eliminated, and 3) precipitation of the final compound is inhibited. Additionally, the use of butylene oxide and very high purity starting materials (Compounds A and D) eliminates the need for a second reaction step using NaOH for the phosphorus ylide conversion (described in the PCT application). The coupling step in this invention, was thus reduced to a single reaction step enhancing the overall product yield.

Other solvents useful in this step include methylene chloride/sodium hydroxide and sodium ethylate or sodium methylate.

2) Ethanol in Saponification Step

In the second step of the new synthesis method, saponification of the diester (Compound E) to TSC is conducted using ethanol as a solvent. The use of an ethanol/sodium hydroxide vehicle for the reaction mixture resulted in a yield at this step (uncorrected) of 92.0% and a corrected yield of 80%. The yields reported here are after isolation. Full conversion of the reactants was observed.

The diethyl ester (Compound E) is poorly soluble in water and in a solvent such as THF used in a synthesis method of PCT Application US03/05521. Hence, the use of ethanol in the subject invention, which is a more favorable solvent for the diethyl ester, reduced reaction times significantly and ultimately led to higher yields. Another suitable alternative in this step is isopropanol or methanol.

The results of the changes made to the synthetic process are summarized in the table below which shows the purity and yield differences between the method of the subject invention and a method of PCT Application US03/05521 and U.S. Ser. No. 10/647,132. It is important to note that the subject process is via diethyl crocetinate (Compound E) at the penultimate step while the PCT Application US03/05521 process is via dimethyl crocetinate (Compound C) at the same step.

Comparison of the Characteristics of Trans Sodium Crocetinate Synthesized by Two Methods

| Parameter | Previous Method Material | Subject Material |
|---|---|---|
| HPLC Purity (measures compositional purity) | 94.21% | 97.56% |
| Melting Point (by DSC) | 3 endothermic events (rather water loss than melting) 22.0-131.3° C. (35.9 J/g) 134.1-161.5° C. (0.6 J/g) 188.1-227.1° C. (1.1 J/g) | 27.3-136.7° C. (53.5 J/g) 141.8-170.9 (1.8 J/g) |
| UV/Vis Data Measure of isomeric purity (0.001M sodium carbonate solution in deionized/distilled water with final solution pH of 8.0) | 421 nm: 1.9425 254 nm: 0.2387 Ratio (Absorbance at 421 nm/Absorbance 254 nm): 8.14 | 421 nm: 2.2111 254 nm: 0.2626 Ratio Absorbance at 421 nm/Absorbance 254 nm): 8.42 |
| Karl-Fisher Water Content | 1.63 wt % | 1.89 wt % |
| Elemental Analysis | C: 62.4 H: 5.9 Na: 11.8 O: 19.4 | C: 61.5 H: 6.2 Na: 13.0 O: 19.8 |
| Intrinsic Particle Size Distribution | Biomodal | Single mode |

Improved Particle Size Distribution

Ethanol Wash

In experiments where an ethanol washing step was used, the final water content of the product was lower, (i.e. 0.5 wt %) vs. the use of a water washing step where the final product water content was 1.8 wt %. The use of an ethanol wash reduced the variability of particle size within the lot, making the distribution more homogeneous. The distribution for TSC produced via the method of PCT Application US03/05521 was bimodal whereas this invention demonstrates a simple normal distribution instead. This improvement is particularly important because particle size can influence solubility and the more homogeneous distribution allows for more uniform solubilities.

The invention thus, includes a method of synthesizing a trans carotenoid compound having the formula:

YZ-TCRO-ZY where:

Y (which can be the same or different at the two ends)=H or a cation, preferably Na$^+$ or K$^+$ or Li$^+$. Y is advantageously a monovalent metal ion. Y can also be an organic cation, e.g., R$_4$N$^+$, R$_3$S$^+$, where R is H, or C$_n$H$_{2n+1}$ where n is 1-10, advantageously 1-6. For example, R can be methyl, ethyl, propyl or butyl.

Z (which can be the same or different at the two ends)=polar group which is associated with the H or cation. Optionally including the terminal carbon on the carotenoid (or carotenoid related compound), this group can be a carboxyl (COO$^-$) group or a CO group (e.g. ester, aldehyde or ketone group), or a hydroxyl group. This group can also be a sulfate group (OSO$_3^-$) or a monophosphate group (OPO$_3^-$), (OP(OH)O$_2^-$), a diphosphate group, triphosphate or combinations thereof. This group can also be an ester group of COOR where the R is C$_n$H$_{2n+1}$. 

TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups are typically methyl groups but can be other groups as discussed below. In an advantageous embodiment, the units of the skeleton are joined in such a manner that their arrangement is reversed at the center of the molecule.

The 4 single bonds that surround a carbon-carbon double bond all lie in the same plane. If the pendant groups are on the same side of the carbon-carbon double bond, the groups are designated as cis; if they are on the opposite side of the carbon-carbon bond, they are designated as trans. The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The method comprises coupling a symmetrical dialdehyde containing conjugated carbon-carbon double bonds with a Wittig agent such as a triphenylphosphorane e.g. [3-carbomethoxy-2-buten-1-ylidene] triphenylphosphorane or a triphenyl phosphonium bromide e.g. a C5 Wittig ester halogenide such as D (2-(Ethoxycarbonyl)-2-buten-4-yl-triphenyl-phosphoniumbromide) or a C2, C3 or C5 phosphonoester such as triphenyl phosphono acetate. The Wittig agent can also be a triphenyl phosphonium chloride or a mixture of the bromide and chloride compounds. Either a single or double step coupling reaction is required depending on the length of the desired TCRO chain. Larger chain lengths require more than one coupling reaction with either the same or different Wittig agent at each step, as demonstrated in the examples herein.

Advantageously, the coupling reaction is made in a pH neutral solvent system such as a butylene oxide solvent system optionally including toluene, or methylene chloride/sodium hydroxide and sodium ethylate or sodium methylate.

After the coupling step is the step of isolating the desired product of the coupling reaction.

After the coupling step, either a second coupling step is performed and the product is isolated as described above or the isolated product from the step above is saponified to form a BTCS compound. If a second coupling reaction is involved, the product from this second step is isolated and then saponified. The product can be saponified using a solution of NaOH, LiOH, KOH and methanol, ethanol or isopropanol as the solvent.

After the saponifying step, the desired product can be washed with ethanol or water. In some cases, methanol or isopropanol is a suitable washing solvent.

Formulation and Administration of the Pharmaceutical Grade Compounds and Compositions of the Invention In formulating trans carotenoids including BTCSSs such as trans sodium crocetinate (TSC) with other ingredients (excipients), it is advantageous to: improve the solubility (increase the concentration of the active agent (e.g. TSC) in solution), stability, bioavailability and isotonic balance of the BTC, reduce the pH of an aqueous solution, and/or increase the osmolality of an aqueous solution. The excipient should act as an additive to prevent self aggregation of monomeric BTC units in solution, or to prevent pre-mature precipitation of BTC. The addition of the excipient should aid in at least one of these aspects. Bipolar trans carotenoid (BTC) molecules can be formulated in a variety of ways. A basic formulation is a mixture of the BTC in sterile water, administered by intravenous injection. This formulation can be modified through the inclusion of various pharmaceutical excipients, including the cyclodextrins. These formulations can also be administered by intravenous injection.

Any of the above described various liquid formulations can be freeze-dried (lyophilized) to form a dry powder with enhanced solubility and stability characteristics. Such powdered forms are then reconstituted for administration. One method is to reconstitute the powder in a liquid such as saline or sterile water for injection and then administer it by intravenous injection. This method can include the use of a multi-compartment syringe containing the powder in one compartment and liquid in the other compartment.

Similarly, the product can be bottled in a vial containing a barrier separating the powder from the liquid. Before administration, the barrier is broken and the components mixed before intravenous injection.

In addition to intravenous injection, routes of administration for specially formulated trans carotenoid molecules include intramuscular injection, delivery by inhalation, oral administration and transdermal administration.

Cyclodextrins

In order to administer some pharmaceuticals, it is necessary to add another compound which will aid in increasing the absorption/solubility/concentration of the active pharmaceutical ingredient (API). Such compounds are called excipients, and cyclodextrins are examples of excipients. Cyclodextrins are cyclic carbohydrate chains derived from starch. They differ from one another by the number of glucopyranose units in their structure. The parent cyclodextrins contain six, seven and eight glucopyranose units, and are referred to as alpha, beta and gamma cyclodextrins respectively. Cyclodextrins were first discovered in 1891, and have been used as part of pharmaceutical preparations for several years.

Cyclodextrins are cyclic (alpha-1,4)-linked oligosaccharides of alpha-D-gluco-pyranose containing a relatively hydrophobic central cavity and hydrophilic outer surface. In the pharmaceutical industry, cyclodextrins have mainly been used as complexing agents to increase the aqueous solubility of poorly water-soluble drugs, and to increase their bioavailability and stability. In addition, cyclodextrins are used to reduce or prevent gastrointestinal or ocular irritation, reduce or eliminate unpleasant smells or tastes, prevent drug-drug or drug-additive interactions, or even to convert oils and liquid drugs into microcrystalline or amorphous powders.

Although the BTC compounds are soluble in water, the use of the cyclodextrins can increase that solubility even more so that a smaller volume of drug solution can be administered for a given dosage.

There are a number of cyclodextrins that can be used with the Compounds of the Invention. See for example, U.S. Pat. No. 4,727,064, hereby incorporated by reference in its entirety. Advantageous cyclodextrins are γ-cyclodextrin, 2-hydroxylpropyl-γ-cyclodextrin and 2-hydroxylpropyl-β-cyclodextrin, or other cyclodextrins which enhance the solubility of the BTC.

The use of gamma-cyclodextrin with TSC increases the solubility of TSC in water by 3-7 times. Although this is not as large a factor as seen in some other cases for increasing the solubility of an active agent with a cyclodextrin, it is important in allowing for the parenteral administration of TSC in smaller volume dosages to humans (or animals). Dosages of TSC and gamma-cyclodextrin have resulted in aqueous solutions containing as much as 44 milligrams of TSC per ml of solution. The solutions need not be equal-molar. The incorporation of the gamma cyclodextrin also allows for TSC to be absorbed into the blood stream when injected intramuscularly. Absorption is quick, and efficacious blood levels of TSC are reached quickly (as shown in rats).

The cyclodextrin formulation can be used with other trans carotenoids and carotenoid salts. The subject invention also includes novel compositions of carotenoids which are not salts (e.g. acid forms such as crocetin, crocin or the intermediate compounds noted above) and a cyclodextrin. In other words, trans carotenoids which are not salts can be formulated with a cyclodextrin. Mannitol can be added for osmolality, or the cyclodextrin BTC mixture can be added to isotonic saline (see below).

The amount of the cyclodextran used is that amount which will contain the trans carotenoid but not so much that it will not release the trans carotenoid.

Cyclodextrin-Mannitol

A trans carotenoid such as TSC can be formulated with a cyclodextrin as noted above and a non-metabolized sugar such as mannitol (e.g. d-mannitol to adjust the osmotic pressure to be the same as that of blood). Solutions containing over 20 mg TSC/ml of solution can be made this way. This solution can be added to isotonic saline or to other isotonic solutions in order to dilute it and still maintain the proper osmolality. See Example 12.

Mannitol/Acetic Acid

A BTCS such as TSC can be formulated with mannitol such as d-mannitol, and a mild acid such as acetic acid or citric acid to adjust the pH. The pH of the solution should be around 8 to 8.5. It should be close to being an isotonic solution, and, as such, can be injected directly into the blood stream. See Example 13.

Water+Saline

A BTCS such as TSC can be dissolved in water (advantageously injectable water). This solution can then be diluted with water, normal saline, Ringer's lactate or phosphate buffer, and the resulting mixture either infused or injected.

Buffers

A buffer such as glycine or bicarbonate can be added to the formulation at a level of about 50 mM for stability of the BCT such as TSC.

TSC and Gamma-Cyclodextrin

The ratio of TSC to cyclodextrin is based on TSC:cyclodextrin solubility data. For example, 20 mg/ml TSC, 8% gamma cyclodextrin, 50 mM glycine, 2.33% mannitol with pH 8.2+/−0.5, or 10 mg/ml TSC and 4% cyclodextrin, or 5 mg/ml and 2% cyclodextrin. The ratios of these ingredients can be altered somewhat, as is obvious to one skilled in this art.

Mannitol can be used to adjust osmolality and its concentration varies depending on the concentration of other ingredients. The glycine is held constant. TSC is more stable at higher pHs. pH of around 8.2+/−0.5 is required for stability and physiological compatibility. The use of glycine is compatible with lyophilization. Alternatively, the TSC and cyclodextrin is formulated using a 50 mM bicarbonate buffer in place of the glycine.

Endotoxin Removal of Gamma-Cyclodextrin

Commercially available pharmaceutical grade cyclodextrin has endotoxin levels that are incompatible with intravenous injection. The endotoxin levels must be reduced in order to use the cyclodextrin in a BTC formulation intended for intravenous injection.

Lyophilization

Lyophilization as well as other crystallization methods can be used to dry the BTC drug.

The Compounds of the Invention can also be formulated according to the section on formulations set forth in U.S. application Ser. No. 10/647,132.

Pulmonary Administration

TSC has been shown to be absorbed into the blood stream following pulmonary administration. The incorporation of the γ-cyclodextrin enhances absorption of TSC into the systemic circulation—with the overall effect of increasing plasma clearance. Also, an increase in the injection volume results in greater TSC absorption and over a longer period of time. Thus, a larger volume injection of the same dose results in a greater bioavailability. It has been found that hemorrhagic shock in rats can be successfully treated by administering TSC via the pulmonary route.

Cyclodextrins are not required for pulmonary absorption. Pulmonary studies consisting of TSC in pH'd di-water showed successful absorption into the blood stream.

Intramuscular Administration

TSC is not absorbed via an intramuscular route when simply dissolved in de-ionized water; however, the addition of a cyclodextrin (as in the formulated drug product) results in absorption into the blood stream. Administration of γ-cyclodextrin with TSC resulted in successful absorption into the systemic circulation. It has been found that hemorrhagic shock in rats can be successfully treated by administering TSC via intramuscular injection. Formulation of TSC with propylene glycol, polyethylene glycol polymers (PEG) and other agents also aids in absorption into the blood stream when TSC is administrated via intramuscular injections. These agents can also be used with other BCTs for intramuscular administration.

Transdermal Administration

TSC has been shown, in rats, to be absorbed into the blood stream following transdermal administration when formulated with cyclodextrins. Formulation of TSC with propylene glycol, polyethylene glycol polymers (PEG), DMSO and other agents also aid in absorption into the blood stream when TSC is administrated transdermally. These agents can also be used with other BCTs for transdermal administration.

Oral Administration

TSC has been shown to be absorbed into the blood stream following oral administration. It was found that the incorporation of a cyclodextrin such as γ-cyclodextrin with a BCT such as TSC enhances absorption of TSC into the systemic circulation. Formulation of a BCT with propylene glycol, polyethylene glycol polymers (PEG) and other agents also enhances oral absorption into the blood stream.

Uses of the Compounds and Compositions of the Invention

The compounds and compositions of the subject invention can be used to treat a variety of disorders in mammals including humans. The above Compounds of the Invention including the intermediate compounds, can be used in the uses below, as well as in the uses set forth in U.S. application Ser. No. 10/647,132.

Trans Carotenoids and Irradiation of Malignant Tumors

In order to overcome hypoxia of tumor cells which gives rise to radioresistance, oxygen therapy is useful. In fact, a quantity has been defined, which is known as the oxygen enhancement ratio (OER). Its value indicates that the dose of radiation that results in a given level of cell survival is greater by a constant factor under hypoxic conditions than when cells are well-oxygenated. For most mammalian cells, the OER is 2.5 to 3. In other words, 2.5 to 3 times the dose of radiation required to kill well-oxygenated cells is necessary to kill hypoxic cells. Thus, increasing the oxygen transport to tumors allows for lower radiation dosages to "kill" the malignant cells. This is important in many types of tumors.

The use of a bipolar trans carotenoid compound such as trans sodium crocetinate has been shown to increase the amount of oxygen reaching hypoxic tissues; thus, it is a very useful radiosensitizer. It allows for reduced radiation dosages to be used, or it increases the effectiveness of irradiation and allows for tumor regression and cures. It is useful for any type of cancer for which radiation is currently used. Radiation therapy is given to about 60% of cancer patients, and a radiation dosage of about 6000-6500 cGy over several weeks is typically used. A BTC or BTCS such as TSC can be used in conjunction with the radiation to get a higher cure rate. In one embodiment, TSC is administered at 0.02 to 2 mg/kg, advantageously 0.05 to 1 mg/kg, before each radiation dosage.

Higher dosages would be used for another type of dosing (e.g. 3 times higher since TSC isn't all absorbed in other routes.).

In one embodiment, another method such as the use of hyperbaric oxygen, breathing of pure oxygen gas, or the administration of another compound such as misonidizole, is done in addition to administration of a BTC compound such as TSC, to enhance the effectiveness of the radiation. These additional methods can also be done with the other uses discussed below (e.g., chemo).

The Compounds of the Invention along with radiation treatment can be used for treating many types of tumors including: squamous cell carcinomas, melanomas, lymphomas, sarcomas, sarcoids, osteosarcomas, tumors associated with skin cancer, breast cancer, head and neck cancer, gynecological cancer, urological and male genital cancer, bladder cancer, prostate cancer, bone cancer, cancers of the endocrine glands, cancers of the alimentary canal (e.g. colon cancer), cancers of the major digestive glands/organs (e.g. stomach, liver, pancreas), CNS cancer (including brain cancers such as a gliomas), and lung cancer.

Trans Sodium Crocetinate (TSC) has been successfully employed as a radiation sensitizer for a human carcinoma that was grafted onto mice. Studies were conducted that concluded that a dosage of TSC ranging from 0.07 mg/kg to 0.18 mg/kg will enhance the effect of irradiation on these tumor types.

Trans Carotenoids and Chemotherapy

Trans carotenoid compounds such as trans sodium crocetinate have been shown to increase the amount of oxygen reaching hypoxic tissues; which can make it useful in combination with chemotherapy of cancer. It allows for an increase in the effectiveness of the chemotherapy. It is useful for any type of cancer for which chemotherapy is currently used. Chemotherapy is given to the majority of cancer patients, with many different types of agents being used. A BTC or BTCS such as TSC can be used in conjunction with the chemotherapy to get tumor regression and a higher cure rate. In one embodiment, TSC is administered at 0.02 to 2 mg/kg, advantageously 0.05 to 1 mg/kg, before, during or after each chemotherapeutic agent is dosed intravenously. If dosed via another route, the dosage will need to be increased by a factor of 2 to 3 to account for the decreased bioavailability.

The Compounds of the Invention along with chemotherapy can be used for treating many types of tumors including: squamous cell carcinomas, melanomas, lymphomas, sarcomas, sarcoids, osteosarcomas, tumors associated with skin cancer, breast cancer, head and neck cancer, gynecological cancer, urological and male genital cancer, bladder cancer, prostate cancer, bone cancer, cancers of the endocrine glands, cancers of the alimentary canal (e.g. colon cancer), cancers of the major digestive glands/organs (e.g. stomach, liver, pancreas), CNS cancer (including brain cancers such as a gliomas), and lung cancer.

Ventricular Fibrillation

The heart beats when electrical signals move through it. Ventricular fibrillation ("V fib") is a condition in which the heart's electrical activity becomes disordered. When this happens, the heart's lower (pumping) chambers contract in a rapid, unsynchronized way. (The ventricles "flutter" rather than beat.) The heart pumps little or no blood.

Ventricular fibrillation is a very serious condition. Collapse and sudden cardiac death will follow in minutes unless medical help is provided immediately. If treated in time, V fib and ventricular tachycardia (extremely rapid heartbeat) can be converted into normal rhythm. The present therapy for this condition requires shocking the heart with a device called a defibrillator. Another effective way to correct life-threatening rhythms is by using an electronic device called an implantable cardioverter-defibrillator. This device shocks the heart to normalize the heartbeat if the heart's own electrical signals become disordered.

Both ventricular fibrillation and tachycardia can also be "corrected" using a Compound of the Invention such as trans sodium crocetinate (TSC). TSC, when injected intravenously during a preclinical study of myocardial infarction, prevented ventricular fibrillation. In addition, TSC has been shown to reduce tachycardia in rats subjected to hemorrhagic shock.

An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

Hypertension

Oxygen consumption in humans declines as they age. In addition, the incidence of hypertension increases with age. While not wishing to be limited to a specific theory, it is believed that these two factors are related, i.e., after tissue oxygen consumption declines, blood pressure increases so as to provide the tissue with more oxygen. Thus, if more oxygen were provided by some other method, blood pressure should decrease. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

The Compounds of the Invention, such as TSC, lower the systolic blood pressure as well as lowering of the diastolic pressure. They can also cause a reduction of the heart rate, and thus cause a decrease in the pulse rate, which is frequently elevated in the hypertensive patient.

An advantageous dosage of TSC for treating hypertension is 0.02-2 mg/kg, and more advantageously 0.05 to 1 mg/kg.

High Lipids

The Compounds of the Invention, such as TSC, can lower plasma lipid levels including triglyceride and cholesterol levels. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

Use with Premature Babies

The Compounds of the Invention, such as TSC, can be used with premature babies to avoid dulling of mental skills. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

Use During Labor

The Compounds of the Invention, such as TSC, can be used by administration to the fetus or mother during labor to avoid oxygen deprivation of the fetus during labor. Oxygen deprivation of the fetus during labor can result in brain damage or autism. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

Use after Smoke Inhalation

The Compounds of the Invention, such as TSC, can be administered after significant smoke inhalation. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

Fibromyalgia

The Compounds of the Invention, such as TSC, can be used to treat fibromyalgia by increasing cellular oxygen levels. An advantageous dosage of TSC is 0.02-2 mg/kg and more advantageously 0.05 to 1 mg/kg if dosed intravenously. If dosed via another route, the dosage will need to be increased by a factor of 2 to 3 to account for the decreased bioavailability.

The following Examples are illustrative, but not limiting of the compounds, compositions and methods of the present invention. Other suitable modifications and adaptations of a variety of conditions and parameters normally encountered which are obvious to those skilled in the art are within the spirit and scope of this invention.

EXAMPLES

List of Abbreviations for Examples a/a [%] Relative purity in %
AP Aqueous layer
Approx. Approximately
COA Certificate of Analysis
corr. Corrected
d Days
DCM Dichloromethane
DSC Differential Scanning calorimetry
E-No. Reference number for each individual compound
Eq Equivalents
EtOAc Ethyl acetate
FW Formula weight
GMP Good manufacturing principles
h Hour
H-NMR Hydrogen nuclear magnetic resonance
HPLC High pressure liquid chromatography
HV Herstellungsvorschrift (Synthesis procedure)
IPC In-Process-Control
IT Inner temperature
JT Jacket temperature
LC-MS Liquid chromatography-mass spectrometry
MeOH Methanol
min Minutes
ML Mother liquor
MOR Master operation record
nc Not corrected
OP Organic layer
RT Room temperature (ca. 22° C.)
sat. Saturated
soln. Solution
sm Starting material
Temp. Temperature
TFA. Trifluoroacetic acid
Th. Theoretical
TPPO Triphenylphosphine oxide
TLC Thin layer chromatography
TSC Trans sodium crocetinate (C-013229)
UV Ultraviolet spectroscopy
y. Yield Example 1

Small-Scale Synthesis of 165 g TSC

Synthesis of Compound E (Diethyl 2,6,11,15-Tetramethyl-hexadeca-2E,4E,6E,8E,10E,12E,14E-heptaene-1,16-diotate)

Overview of Chemical Reaction

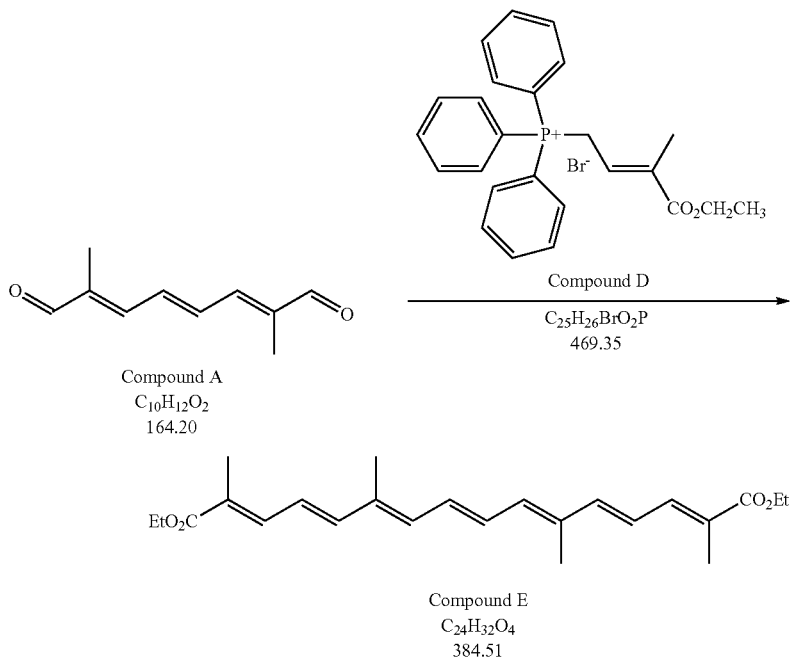

-continued

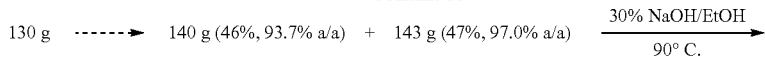

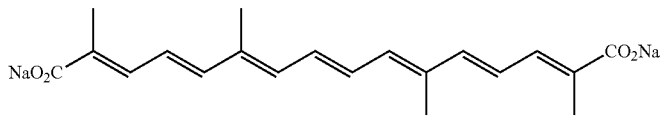

Final Product-TSC
$C_{20}H_{22}Na_2O_4$
372.37

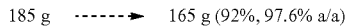

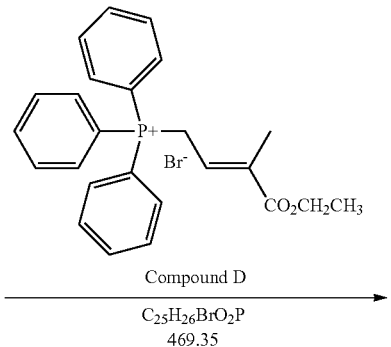

Compound A
$C_{10}H_{12}O_2$
164.20

Compound D
$C_{25}H_{26}BrO_2P$
469.35

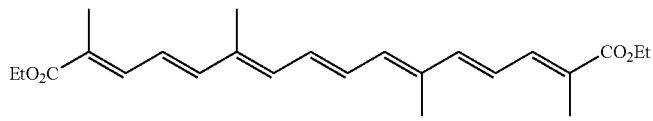

Compound E
$C_{24}H_{32}O_4$
384.51

| Size: | 130 g Compound A | 0.792 mol (nc) |
|---|---|---|
| Th. Quantity: | 304.4 g Compound E | |
| Pr. Quantity: | 139.6 g Compound D + 143.2 g Compound E | 0.736 mol (nc) |
| Yield (nc): | 92.9% | Purity: 93.68% + 96.99% a/a HPLC |

| Pos. | Reagent | Molecular Wt. | Eq. | Quantity | Unit |
|---|---|---|---|---|---|
| 1 | Compound A | 164.20 | 1.0 | 130 | g |
| 2 | Compound D | 444.01[1] | 3.0 | 1052 | g |
| 3 | Butylene oxide | | | 0.64 | L |
| 4 | Toluene | | | 1.27 | L |
| 5 | Ethanol | | | 0.15 | L |
| 6 | Methylcyclohexane | | | 0.79 | L |
| 7 | Butylene oxide | | | 0.20 | L |
| 8 | Toluene | | | 0.50 | L |
| 9 | Ethanol | | | 0.10 | L |
| 10 | Methylcyclohexane | | | 0.40 | L |
| 11 | Methanol | | | 1.00 | L |

[1]The used material was a salt mixture containing 48% bromide and 52% chloride according to the CoA of the supplier. Thus, the real mass was different from the theoretical one as depicted on the formula scheme.

Procedure

1. A flask was evacuated and purged with nitrogen.
2. The flask was charged with Compound A (1) and Compound D (2) at JT=20° C.
3. Butylene oxide (3) and toluene (4) were charged to the flask at JT=20° C. The flask was evacuated and purged with nitrogen twice. The reaction mixture was warmed to JT=100° C. A homogenous solution was obtained.
4. The solution was stirred at JT=100° C. for 6.5 h. (IT was about 93° C.).
5. A sample for an IPC was taken.
   IPC1 #2 No aldehyde signals were detected ($^1$H-NMR), see Note 1.
6. The mixture was slowly cooled to IT=20° C. (15 h.).
7. A red suspension was formed. The suspension was cooled to IT=1° C. within 2 h.
8. The suspension was filtered on a filter dryer within for a few minutes.
9. Cold ethanol (5), at 2° C., was used to rinse the flask. The rinse solution was transferred to the filter dryer.
10. The filter cake was washed with methylcyclohexane (6) at 22° C.
11. The filter cake was dried on a rotary evaporator for 5 h. at 55° C.
12. 139.6 g Compound E was obtained as a red solid. The identity was confirmed by $^1$H-NMR. The purity was 93.68% a/a as determined by HPLC. In addition, 2.90+ 3.00% cis isomers were also observed. The yield (nc) was 45.9%.

13. The mother liquor (about 3 L) was concentrated to 40% of its volume (still a red solution) and stirred at JT=100° C. for 15 h. (IT was about 100° C.).
14. A red suspension was formed. A sample for an IPC was taken.
   IPC2 #1 Little or no cis isomer was detectable ($^1$H-NMR).
15. The mixture was diluted with butylene oxide (7) and toluene (8, still a suspension) and cooled to IT=2.9° C. within 3.5 h.
16. The suspension was filtered on a filter dryer within 10 min.
17. Cold ethanol (9), about 2° C., was used to rinse the flask. The rinse solution was transferred to the filter dryer.
18. The filter cake was washed with methylcyclohexane (10) at 18° C.
19. The filter cake was dried on a rotary evaporator for 15 h. at 50° C.
20. 384.5 g crude product was obtained as a red solid. An $^1$H-NMR revealed the presence of TPPO in addition to the desired product.
21. The crude product was treated with methanol (11) and stirred for 30 min. at JT=60° C.
22. The suspension was cooled to JT=0° C. within 60 min.
23. The suspension was filtered on a filter dryer within a few minutes.
24. Methanol (11) was used to rinse the flask. The rinse solution was transferred to the filter dryer.
25. The filter cake was dried on a rotary evaporator for 2 h. at 55° C.
26. 143.2 g crude product was obtained as a red solid. The identity was confirmed by $^1$H-NMR. The purity was 96.99% a/a by HPLC. In addition, 1.02+1.26% cis isomers were observed. The yield (nc) was 47.0%. The $^1$H-NMR showed about 11.5% TPPO.

Notes
1) A first IPC was taken after 2.5 h. This showed a complete consumption of the aldehyde and additional cis isomer. The ratio of isomers improved with the time for the reaction.

Sample Preparation

| In-Process-Control (IPC): | Conversion: About 0.5 ml of the reaction mixture were taken, evaporated and analysed by $^1$H-NMR or HPLC. |
|---|---|
| Purity: | 6-7 mg of the product were analysed by HPLC; method HPLC-TSC-M1.1. |
| $^1$H-NMR's | 5-10 mg of the product were dissolved in 0.9 ml CDCl$_3$ (internal standard: TMS) for NMR spectroscopy. |

Synthesis of TSC from Compound E

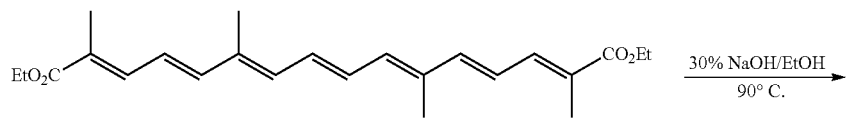

C$_{24}$H$_{32}$O$_4$
384.51
Diethyl crocetinate
(Diethyl 2,6,11,15-Tetramethyl-hexadeca-
2E,4E,6E,8E,10E,12E,14E-
heptaene-1,16-diotate)

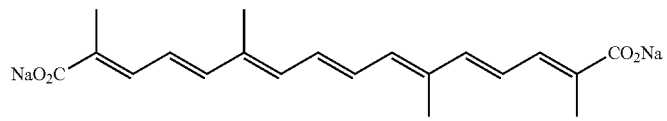

C$_{20}$H$_{22}$Na$_2$O$_4$
372.37
Trans sodium crocetinate

| Size: | 185 g Compound A | | 0.481 mol (nc) |
|---|---|---|---|
| Th. Quantity: | 179.2 g TSC | | |
| Pr. Quantity: | 164.9 g TSC | | 0.443 mol (nc) |
| Yield (nc): | 92.0% | Purity: | 97.56% a/a HPLC |

| Pos. | Reagent | Molecular Wt. | Eq. | Quantity | Unit |
|---|---|---|---|---|---|
| 1 | Compound E | 384.51 | 1.0 | 139 +46[2] | g g |
| 2 | Ethanol | | | 0.72 | L |
| 3 | 30% NaOH | | | 0.72 | L |
| 4 | Water | | | 2.21 | L |
| 5 | Water | | | 1.92 | L |
| 6 | Water | | | 1.92 | L |
| 7 | Water | | | 1.92 | L |

[2]The exact quantity of starting material was slightly lower than depicted, because the second portion (46 g) contained about 11.5% TPPO in it according to the $^1$H-NMR.

Procedure
1. A flask was evacuated and purged with nitrogen.
2. The flask was charged with Compound E (1) at JT=20° C.
3. Ethanol (2) and 30% NaOH (3) were charged to the flask at JT=20° C. The flask was evacuated and purged with nitrogen twice. The reaction mixture was warmed to JT=90° C. A thick, orange suspension was obtained.
4. The suspension was stirred at JT=90° C. for 47 h. (IT about 77° C.).
5. The mixture was cooled to IT=21° C. within 16 h. A sample for an IPC was taken.
   IPC1 #1 98.2% conversion monoester to TSC (HPLC); no diester (Compound E) was detected.
6. The mixture was diluted with water (4).
7. The suspension was filtered on a filter dryer within 50 min.
8. Cold water (5), at 3° C., was used to rinse the flask and to wash the filter cake.
9. The filter cake was washed further with cold water (6+7), at 5° C. and 2° C.
10. The filter cake was dried on a rotary evaporator for 20 h. at 55° C.
11. 164.9 g TSC was obtained as an orange solid. The identity was confirmed by $^1$H-NMR. The purity was 97.56% a/a as measured by HPLC. The yield (nc) was 92.0%. The water content was determined to be 1.89% w/w, the UV ratio 421 nm to 254 nm was 8.42. Anal Calculated for $C_{20}H_{22}O_4Na_2$-0.5$H_2O$-0.2NaOH: C, 61.41; H, 6.03; Na, 12.93; 0, 19.63. Found: C, 61.5; H, 6.2; Na, 13.0; 0, 19.8.

Sample Preparation

| In-Process-Control (IPC): | Conversion: About 0.5 ml of the reaction mixture were taken and analysed by HPLC. |
| Purity: | 6-7 mg of the product were analysed by HPLC; method HPLC-TSC-M1.1. |
| $^1$H-NMR's | 5-10 mg of the product were dissolved in 0.9 ml $D_2O$ for NMR spectroscopy. |

Example 2

Production of Larger-Scale (2 kg) TSC Under cGMP Conditions

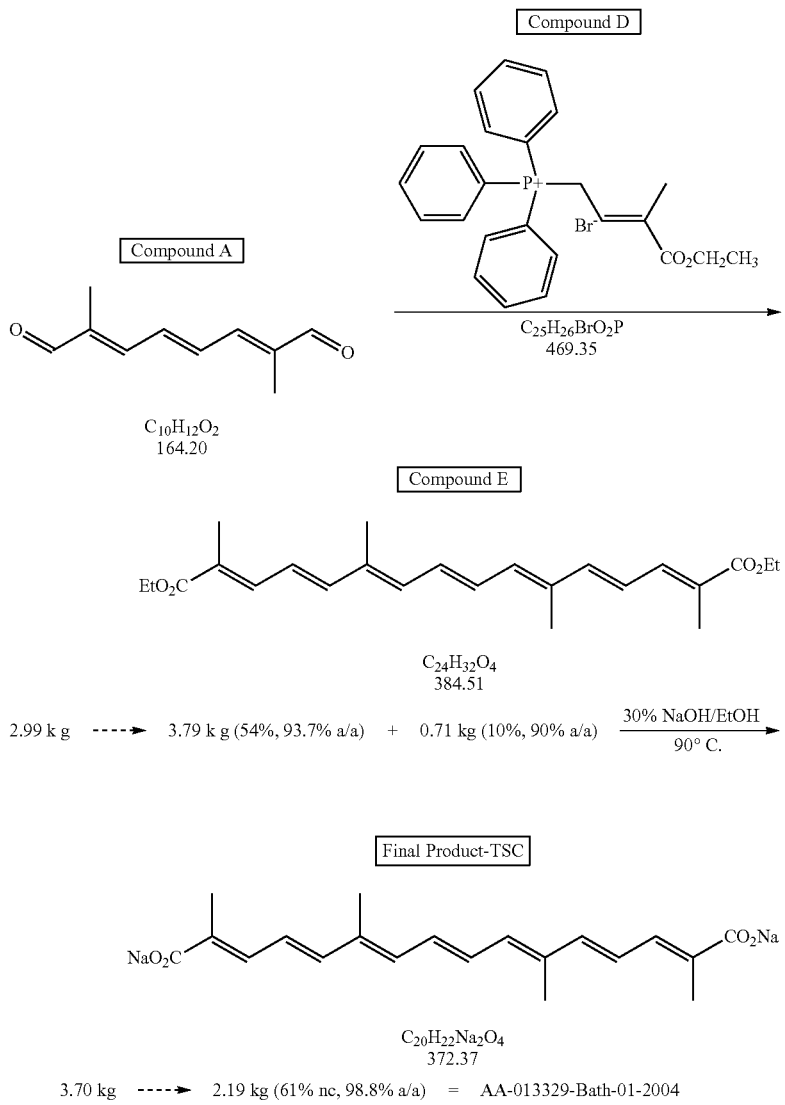

Raw Materials

The quality of the starting materials (Compounds A and D) were verified and testing results are shown below:

| Lot-No. | HPLC-Purity (% a/a) | Appearance | Identity by IR |
|---|---|---|---|
| E-027211-002 (UQ40112015; C10 dial,; Compound A) | 95.22 | Yellow Powder | Complies |
| E-027684-001 (UQ40112015; C10 dial,; Compound A) | 94.70 | Yellow Powder | Complies |
| E-027684-002 (UQ40112015; C10 dial,; Compound A) | 94.60 | Yellow Powder | Complies |
| E-027758-001- E-027758-003, E-027685-001- E-027685-021 (UE00401004; C5 Wittig ester,; Compound D) | 97.88 | White Powder | Complies |

All materials fulfilled the given specifications (Compound D: ≥97.0%; Compound A: ≥94.0%). Furthermore, all materials were prepared synthetically without the use of any animal components or any components derived from animal products.

The C-10 dial (Compound A) was a yellow crystalline powder. The phosphorane, Compound D, was a white to yellow powder. The identities were checked by $^1$H-NMR.

| Size: | 2.99 kg Compound A | 18.21 mol (nc) |
|---|---|---|
| Th. Quantity: | 7.00 kg Compound E | |
| Pr. Quantity: | 3.79 kg Compound E+ 705 g Compound E | 11.69 mol (nc) |

| Yield (nc): | 64.2% | Purity: | 93.70% + 90.01% a/a HPLC |
|---|---|---|---|

| Pos. | Reagent | Molecular Wt. | Eq. | Quantity | Unit |
|---|---|---|---|---|---|
| 1 | Compound A | 164.20 | 1.0 | 2.99 | kg |
| 2 | Compound D | 444.01[3] | 3.0 | 24.04 | kg |
| 3 | Butylene oxide | | | 15 | L |
| 4 | Toluene | | | 30 | L |
| 5 | Butylene oxide | | | 9 | L |
| 6 | Ethanol | | | 4 | L |
| 7 | Methylcyclohexane | | | 18 | L |
| 8 | Methanol | | | 17.5 | L |
| 9 | Butylene oxide | | | 3 | L |
| 10 | Toluene | | | 11 | L |
| 11 | Butylene oxide | | | 7 | L |
| 12 | Toluene | | | 10 | L |
| 13 | Methylcyclohexane | | | 7 | L |
| 14 | Methanol | | | 13 | L |
| 15 | Methanol | | | 14 | L |

[3]The used material was a salt mixture containing 48% bromide and 52% chloride according to the CoA of the supplier. Thus, the real mass was different from the theoretical one as depicted on the formula scheme.

Procedure

1. A 100 L reactor was evacuated and purged with nitrogen twice.
2. The 100 L reactor was charged with Compound A (1) and Compound D (2) at JT=20° C.

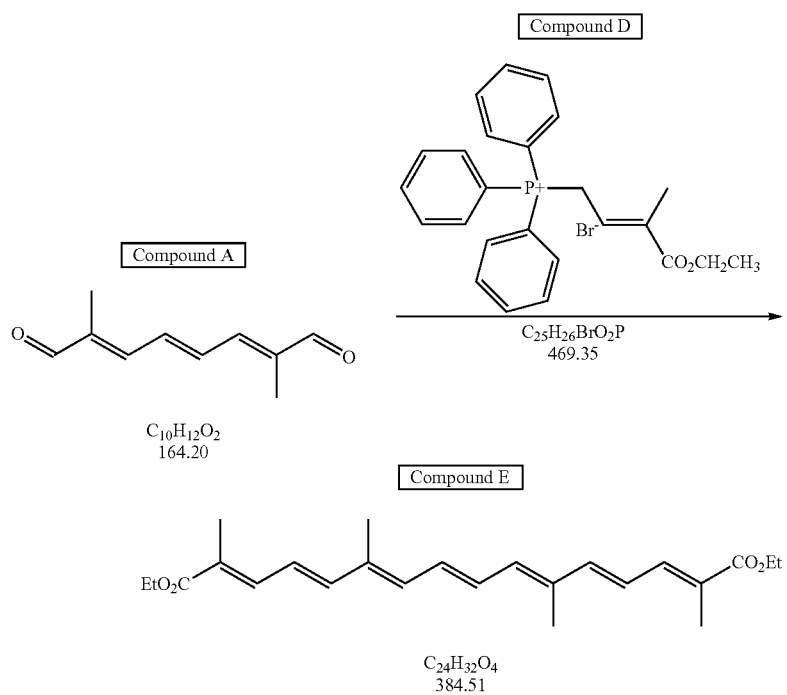

Synthesis of Compound E

3. Butylene oxide (3) and toluene (4) were charged to the reactor at JT=20° C. The 100 L reactor was evacuated and purged with nitrogen twice. The reaction mixture was warmed to JT=100° C. A homogenous solution was obtained.

4. The solution was stirred at JT=100° C. for 4 h. (IT was about 98° C.).
5. The solution was concentrated under a slight vacuum at JT=110° C. 9.0 L solvent was removed. The mixture was stirred at JT=110° C. for 13 h. (IT was about 105° C.).
6. The mixture was diluted with butylene oxide (5) and cooled to IT=20° C. (2.75 h.). A red suspension was formed.
7. A sample for an IPC was taken.
   IPC1 #1 No aldehyde signals were detected ($^1$H-NMR), see Note 1.
8. The mixture was cooled to IT=0° C. (80 min).
9. The suspension was filtered on a filter dryer within 100 min.
10. Cold ethanol (6) was used to rinse the 100 L reactor. The rinse solution was transferred to the filter dryer.
11. The filter cake was washed with methylcyclohexane (7).
12. The filter cake was dried on a rotary evaporator for 4.5 h. at 55° C.
13. 5.246 kg crude product was obtained as a red solid. An $^1$H-NMR spectrum revealed the presence of a substantial quantity of TPPO (about 25%-30%) in addition to the desired product.
14. The crude product was transferred on a filter dryer and washed with methanol (8).
15. The filter cake was dried on a rotary evaporator for 19 h. at 55° C.
16. 3.787 kg Compound E was obtained as a red solid (crude3 #1). The identity was confirmed by $^1$H-NMR. The purity was 93.70% a/a as measured by HPL. In addition, 3.17+2.54% cis isomers were also observed. The yield (nc) was 54.1%.
17. The mother liquor (about 81 L) was concentrated under a slight vacuum at JT=100° C. 30 L solvent was removed. The mixture was stirred at JT=110° C. for 12.5 h. (IT was about 105° C.).
18. The mixture was diluted with butylene oxide (9) and toluene (10) and cooled to IT=20° C. (2.75 h.). A red suspension was formed.
19. A sample for an IPC was taken, cooled to 0° C. and filtered.
    IPC3 #1 Still too much TPPO in product ($^1$H-NMR).
20. The mixture was diluted with butylene oxide (11) and toluene (12), warmed to JT=60° C. and cooled again to IT=20° C.
21. A filtered sample was taken and washed with methanol.
    IPC3 #2 Content of TPPO in product was reduced significantly ($^1$H-NMR).
22. The suspension was cooled to 1° C. within 60 min and filtered on a filter dryer within 60 min.
23. The filter cake was washed with methylcyclohexane (13).
24. The filter cake was washed twice with methanol (14+15).
25. The filter cake was dried on a rotary evaporator for 4.5 h. at 55° C.
26. 705 g crude product was obtained as a red solid (crude2 #1). The identity was confirmed by $^1$H-NMR. The purity was 90.01% a/a as measured by HPLC. Additionally, 3.83%+5.34% cis isomers were noted on the HPLC. The yield (nc) was 10.1%. The total corrected yield was 63.0%.

Notes
1) The ratio of isomers was about 60:40 trans/cis according to the HPLC.

Sample Preparation

| In-Process-Control (IPC): | Conversion: About 0.5 ml of the reaction mixture were taken, evaporated and analysed by $^1$H-NMR or HPLC. |
| --- | --- |
| Purity: | 6-7 mg of the product were analysed by HPLC; method HPLC-TSC-M1.1. |
| $^1$H-NMR's | 5-10 mg of the product were dissolved in 0.9 ml CDCl$_3$ (internal standard: TMS) for NMR spectroscopy. |

Synthesis of TSC from Compound E

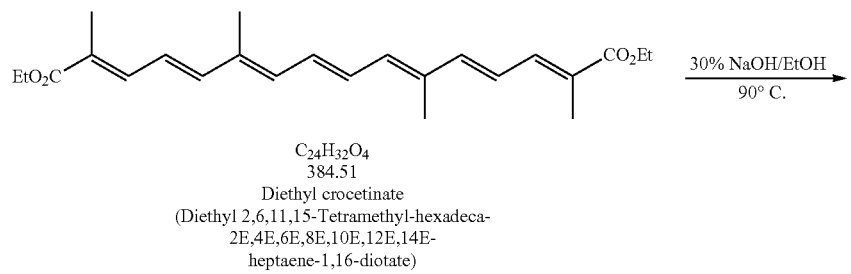

C$_{24}$H$_{32}$O$_4$
384.51
Diethyl crocetinate
(Diethyl 2,6,11,15-Tetramethyl-hexadeca-2E,4E,6E,8E,10E,12E,14E-heptaene-1,16-diotate)

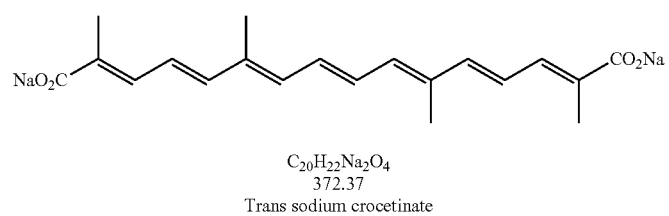

C$_{20}$H$_{22}$Na$_2$O$_4$
372.37
Trans sodium crocetinate

| Size: | 3.70 kg Compound A | | 9.62 mol (nc) |
|---|---|---|---|
| Th. Quantity: | 3.58 kg TSC | | |
| Pr. Quantity: | 2.19 kg TSC | | 5.88 mol (nc) |
| Yield (nc): | 61.2% | Purity: | 98.76% a/a HPLC |

| Pos. | Reagent | Molecular Wt. | Eq. | Quantity | Unit |
|---|---|---|---|---|---|
| 1 | Compound E | 384.51 | 1.0 | 3.70 | kg |
| 2 | Ethanol | | | 15.7 | L |
| 3 | 30% NaOH | | | 15.0 | L |
| 4 | Water | | | 45 | L |
| 5 | Ethanol | | | 3.5 | L |
| 6 | Water | | | 39 | L |
| 7 | Water | | | 39 | L |
| 8 | Water | | | 38 | L |
| 9 | Ethanol | | | 39 | L |

Procedure

1. A 100 L reactor was evacuated and purged twice with nitrogen.
2. The 100 L reactor was charged with Compound E (1) at JT=20° C.
3. Ethanol (2) and 30% NaOH (3) were charged to the 100 L reactor at JT=20° C. The 100 L reactor was evacuated and purged with nitrogen twice. The reaction mixture was warmed to JT=90° C. A thick, orange suspension was obtained.
4. The suspension was stirred at JT=90° C. for 63 h (IT at 81° C.).
5. The mixture was cooled to IT=21° C. within 2 h. A sample for an IPC was taken.
   IPC1 #1 98.7% conversion monoester to TSC (HPLC); no diester (Compound E) was detected.
6. The mixture was diluted with water (4).
7. The suspension was filtered on a filter dryer within 15 h.
8. Ethanol (5) was used to rinse the 100 L reactor.
9. The filter cake was washed three times with cold water (6, 7+8), between 0° C.-5° C.
10. The filter cake was washed with ethanol (9).
11. The filter cake was dried on a rotary evaporator for 5 h. at 50° C.
12. 2.186 kg TSC was obtained as an orange solid. The identity was confirmed by $^1$H-NMR. The purity was 97.96% a/a as measured by HPLC. The yield (nc) was 61.2%; see Note 1. The water content was determined to be 1.58% w/w and the UV ratio 421 nm to 254 nm to be 8.9. Anal Calc for $C_{20}H_{22}O_4Na_2 \cdot 0.34H_2O$: C, 63.47; H, 6.04; Na, 12.15; 0, 18.35. Found: C, 63.81; H, 5.64; Na, 12.21; 0, 18.34.
13. 2.184 kg crude1 #1 was shaken in a blender for 4 days at RT. The remaining lumps were easily ground down with a pestle. 2.183 kg crude2 #1 (corresponded to AA-013329-Batch-01-2004) orange solid was obtained. The purity was 98.76% a/a HPLC. A DSC measurement revealed no difference.

Notes

1) The product is soluble in water. Thus, the long filtration time as well as the additional water washing might have caused the low yield observed in this specific situation. The third water washing was performed to fit the desired sodium content in product.

Sample Preparation

| In-Process-Control (IPC): | Conversion: About 0.5 ml of the reaction mixture were taken and analysed by HPLC. |
|---|---|
| Purity: | 6-7 mg of the product were analysed by HPLC; method HPLC-TSC-M1.2. |
| $^1$H-NMR's | 5-10 mg of the product were dissolved in 0.9 ml $D_2O$ for NMR spectroscopy. |

Analytics
HPLC Methods
Method: HPLC-TSC-M.1.2
Replaces Method: HPLC-TSC-M.1.1
Method valid for: C-009594, Compound A, TSC, Compound D, Compound E
Chemicals: Acetonitrile, HPLC grade (J.T. Baker or equivalent)
   Water, HPLC grade (Milli-Q system purified or equivalent)
   Trifluoroacetic acid (Merck or equivalent)
   THF, HPLC grade, without stabilizer (Scharlau or equivalent)
   MeOH, HPLC grade (Scharlau or equivalent)
Equipment: HP-1100-System or equivalent
   Column: YMC Pack Pro C18, 100×4.6 mm, 3 μm
Mobile Phase Preparation:
Solution A: 0.1% TFA in $H_2O$/ACN 90:10% v/v
Solution B CAN
Sample Preparation:
Mixing Solvents THF, MeOH, $H_2O$, ACN
C-009594, C-013327: 6-7 mg (accurately weighed) of the crude material is dissolved in MeOH
C-014679: 6-7 mg (accurately weighed) of the crude material is dissolved in 30 mL ACN and filed up with water to the 100 mL line.
C-014681: 6-7 mg (accurately weighed) of the crude material is dissolved in 100 mL THF.
C-013329: 6-7 mg (accurately weighed) of the crude material is dissolved in 10 mL $H_2O$ and filled up to 100 mL with THF.
HPLC Parameters:

| Column: | YMC Pack Pro C18, 100 × 4.6 mm, 3 μm | |
|---|---|---|
| Mobile phase: | A: 0.1% TFA in $H_2O$/ACN 90:10% v/v<br>B: ACN | |
| Gradient: | 0.00 min | 30% B |
| | 12.00 min | 95% B |
| | 16.00 min | 95% B |
| | 16.10 min | 30% B |
| | 20.00 min | 30% B |
| Flow rate: | 1 mL/min | |
| Temperature: | 20° C. | |
| Detection: | 421 nm (if detector is able to: 220, 230, 254 and 350 nm in addition) | |
| Injection volume: | 10 μL | |

Integration Parameters:
   NA
Identification Table for the Following HPLC Traces:

| Retention times* [min] | molecular weight [g/mol] | Proposed structures/ C- numbers | relative retention times |
|---|---|---|---|
| 3.54 | 469 | Compound D | 0.51 |
| 4.47 | 164 | Compound A | 0.65 |

-continued

| Retention times* [min] | molecular weight [g/mol] | Proposed structures/ C- numbers | relative retention times |
|---|---|---|---|
| 4.99 | 278 | C-009594 | 0.72 |
| 6.90 | 372 | TSC | 1.00 |
| 14.30 | 384 | Compound E | 2.07 |

*typical retention times for G-1172 with column LC-0402.

UV Methods

Modified method for this synthesis:
Method: UV-TSC-M.2.1
Replaces Method: -
Method valid for: TSC
Chemicals: Water, HPLC grade (Milli-Q system purified or equivalent)
Equipment: Perkin Elmer Lambda 25-System or equivalent
Cuvette: 1 cm Quartz glass
UV parameters: Wavelength: 421 nm; 350 nm; 254 nm
Sample preparation: 10 mg (accurately weighted) was dissolved in 50 mL water. The sample was ultrasonicated for 30 min. at 45°-50° C. 1 mL of this solution was diluted with an additional 49 mL of water (making a total solution volume of 50 ml).

Document and method history: Sample preparation of customer method modified in order to measure within the linear range.

Example 3

Synthesis of Trans Potassium Crocetinate (di-potassium 2,6,11,15-tetramethylhexadeca-2E,4E,6E,8E, 10E,12E,14E,-heptane-1,16-diotate)

Trans potassium crocetinate is also referred to below as TPC or Compound F. The chemical synthesis is shown below.

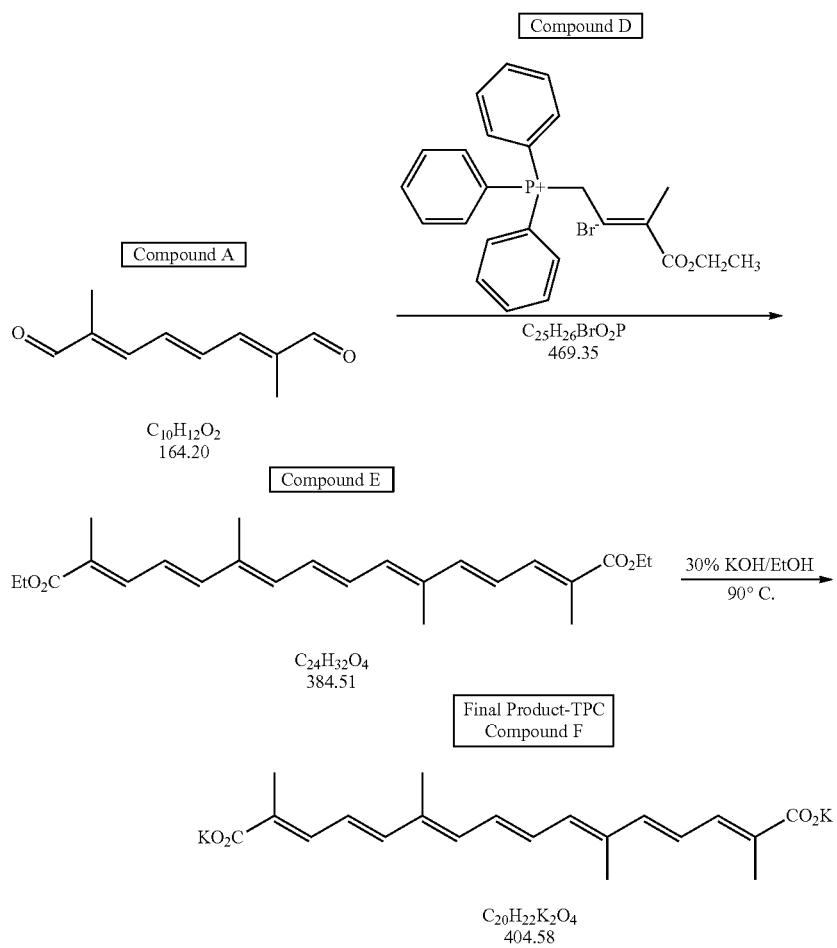

The saponification reaction (last step in the synthesis) was performed in a similar fashion to the process used in Examples 1 and 2 above. The diethyl ester, Compound E, was prepared as described above in Examples 1 and 2.

For this example, Compound E was treated with 30% potassium hydroxide (KOH) (1.5 ml/mmol) in ethanol (EtOH) (1.5 ml/mmol) at 90° C. for 4 days. The mixture was diluted with ethanol due to some solvent loss during the process. The orange product was isolated by filtration at room temperature (22° C.) and by washing with 50% ethanol in water (3×). The product was dried on a rotary evaporator for 5 h at JT=60° C. This produced a reaction yield of 86% (12 g experiment). An $_1$H-NMR spectrum and an LC-MS spectrum confirmed the desired product was trans potassium crocetinate. The HPLC quality was 98.3% using the HPLC method described above in Example 2 with a detection wavelength of 421 nm.

Example 4

Synthesis of Trans Lithium Crocetinate (di-lithium 2,6,11,15-tetramethylhexadeca-2E,4E,6E,8E,10E,12E,14E,-heptane-1,16-diotate)

Trans lithium crocetinate is also referred to below as TLC or Compound G. The chemical synthesis is shown below.

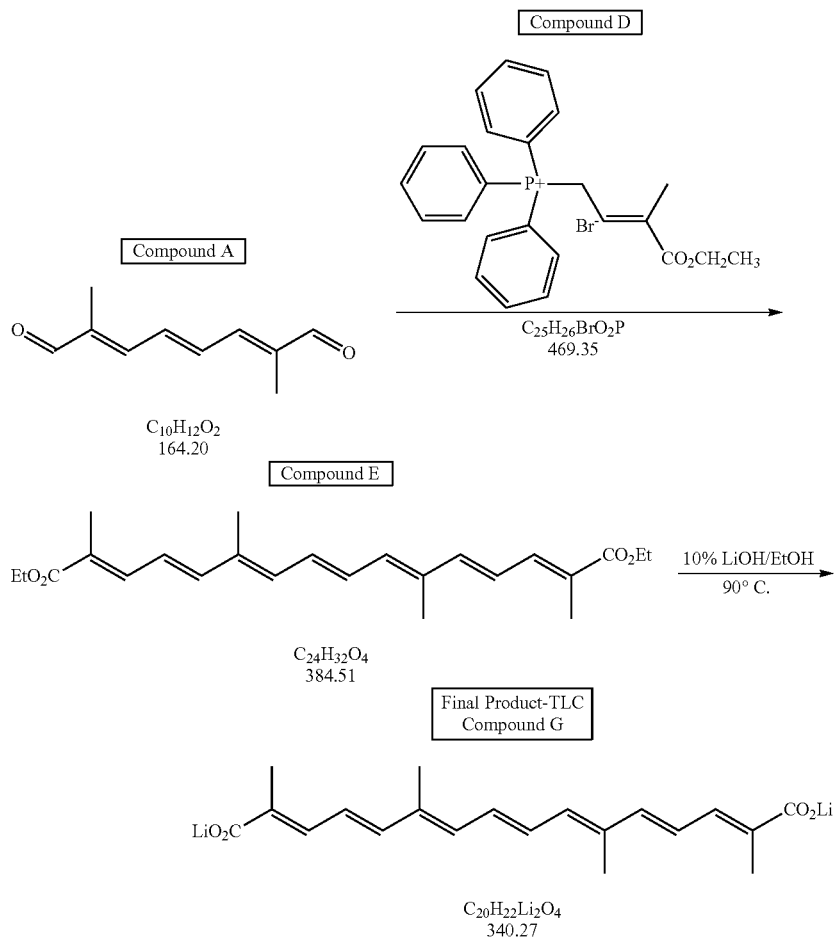

The saponification reaction was performed by a process similar to that outlined in Examples 1-3. In this case, however, lithium hydroxide was used as the saponification agent. In this example, Compound E was again synthesized as described in Examples 1 and 2. Compound E was treated with 10% lithium hydroxide (LiOH) (2.8 ml/mmol) in ethanol (EtOH) (1.5 ml/mmol) at 90° C. for 4 days. The dark-orange suspension was filtered at room temperature (22° C.) and was washed with 50% ethanol in water (3×) and pure ethanol. The dark orange solid was dried on a rotary evaporator for 5 h at jacket temperature (JT)=60° C. This produced 9.5 g dark-orange solid.

HPLC analysis of this compound indicated 38% a/a starting material remained in addition to the desired product. The substantial amount of remaining starting material is likely a result of using a less concentrated basic solution (LiOH) in this saponification reaction. In this case, given the limited solubility of LiOH in water, only a 10% solution of LiOH in water was used. In the other examples (1-3 described herein), a 30% basic solution in water was used.

In order to improve the reaction yield, the isolated product from the previous step was treated with solid LiOH (13 eq.) in 50% EtOH in water (2.9 ml/mmol) at 95° C. for further 2 days. The orange product resulting from this second treatment with lithium hydroxide was isolated by filtration at room temperature and by washing with 50% EtOH in water (3×) and pure EtOH. The resulting solid was dried on a rotary evaporator for 3 h at jacket temperature=60° C. This gave a yield of 14 g product. Because this was more than the theoretical yield, an additionally slurry in water (1.6 ml/mmol) was performed to remove the excess of LiOH. The orange product was isolated by filtration at room temperature and washing with 50% EtOH in water (3×) and pure EtOH. The product was dried on a rotary evaporator for 2 h at jacket temperature=60° C. This gave a yield of 8.5 g, which corresponds to an overall reaction yield of 67% (12 g experiment).

Both $_1$H-NMR and LC-MS spectra confirmed the desired product, trans lithium crocetinate, was obtained. The HPLC quality was 99.7% using the analysis procedure described above in Example 1 with a detection wavelength set at 421 nm.

Example 5

Synthesis of the C-14 Derivative of TSC (disodium 4,9-dimethyldodeca-2E,4E,6E,8E,10E-pentane-1,12 diotate)

The synthesis of symmetric compounds with a shorter chain length than TSC required the use of a different Wittig agent other than the Compound B shown in Examples 1-4. Shorter chain length BPTC compounds are synthesized using Compound A, the C-10 dialdehyde used previously. Compound A was then converted via either a Homer-Emmons reaction or a Wittig coupling reaction with either a commercially-available C2 or C3-phosphonate or a phosphonium bromide (Compound H) to form the corresponding C14- and C16-esters, respectively. Hydrolysis with NaOH/EtOH completed the reaction, resulting in the formation of the desired C14 or C16-derivatives of TSC.

The synthesis of the C-14 derivative of TSC, Compound J, was completed via the reaction of Compound A and Compound H (ethoxycarbonyl-methyl-triphenyl-phosphonium bromide). Compounds A and H reacted to form the final intermediate, Compound I, prior to a saponification step which produced Compound J as shown below.

H). This coupling reaction was performed in butylene oxide/toluene 2:1 (0.7 ml+1.4 ml/mmol) as used in Examples 1-4 above. The result was good product formation with 3 eq. Wittig reagent at jacket temperature=100° C. A yellow product was isolated by filtration at 0° C. and subsequent washing (twice) with methylcyclohexane. The yield for this step was 56-61% (10 g scale).

The purity was determined to be 83.4% a/a trans isomer at a detection wavelength of 369 nm (11.5 min) using HPLC. In addition to Compound I, an additional three compounds were observed to be present in the HPLC trace and are speculated of be cis isomers of Compound I (1.0% a/a, 10.5 min; 13.4% a/a, 11.2 min; 2.0% a/a, 11.9 min).

Saponification Reaction to Form the Final Product (Compound J)

The saponification reaction to convert compound I to Compound J was performed in a manner similar to that described in Examples 1-4. The diethyl ester, Compound I, was treated with 30% NaOH (2 ml/mmol) in EtOH (4 ml/mmol) at 90° C. for 3 days. The yellow product was isolated by filtration at room temperature and by washing with 50% EtOH in water (5×) and pure EtOH (3×). The saponification reaction gave a crude yield of about 100%. In order to improve the purity, the mixture was slurried in 30%

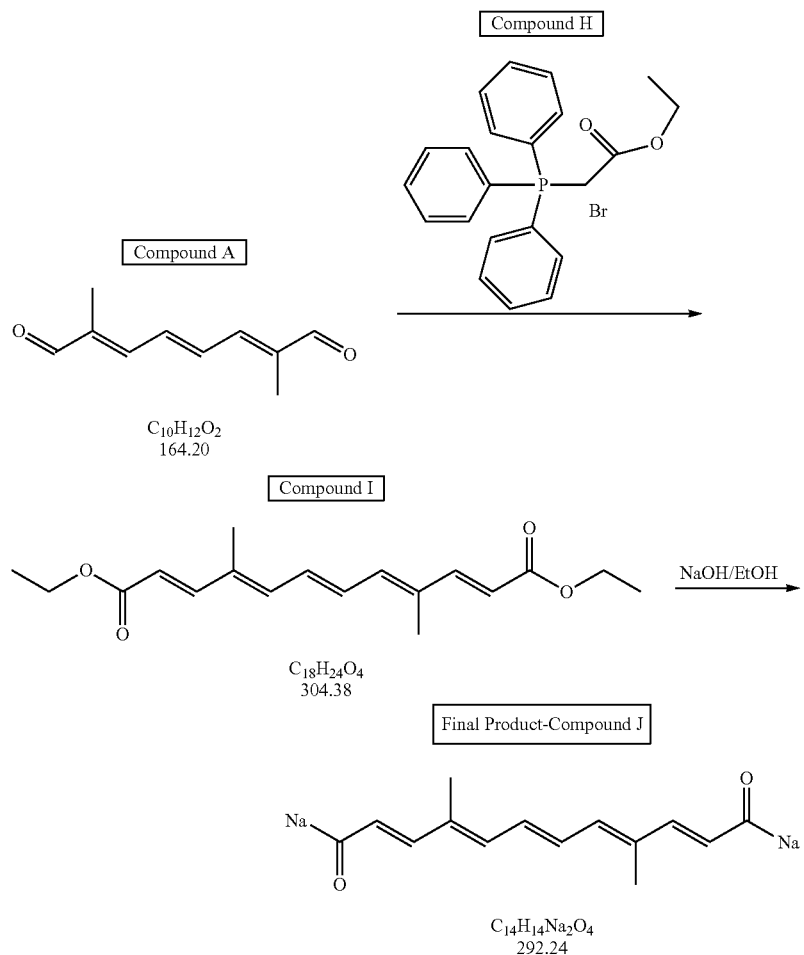

Coupling Reaction to Form Compound I

The best method for the formation of Compound I consisted of using the C2 phosphonium bromide (Compound NaOH (0.5 ml/mmol) in EtOH (1 ml/mmol) at 90° C. for 4 h. The suspension was filtered at 0° C. and washed with EtOH (3×) giving a yellow product, which corresponded to an uncorrected yield of 79% (10 g scale). $_1$H-NMR confirmed that the desired product, Compound J, was synthesized with an HPLC quality of 97.8% with a detection wavelength set at 383 nm.

Example 6

Synthesis of the C-15 Derivative of TSC (disodium 2,4,9-Trimethyldodeca-2E,4E,6E,8E,10Epentaene-1,12-diotate)

Compound A was reacted with Compound K (1-(Ethoxycarbonyl)-ethyltriphenylphosphoniumbromide), a C3 phosphonium salt/C3 Wittig ester bromide to produce the first intermediate in this reaction sequence, Compound M. Alternatively, in this first step, the same result can be achieved if Compound A is reacted with Compound L (Triethyl-2-phosphonopropionate), a C3 phosphono ester, to produce intermediate Compound M.

In the second coupling reaction, Compound M was reacted with Compound H (ethoxycarbonyl-methyltriphenylphosphoniumbromide), a C2 phosphonium salt/C2 Wittig ester bromide, to form the penultimate intermediate, Compound O. Alternatively, Compound O can be formed via a reaction between Compound M and Compound N (triethyl-phosphono-acetate), a C2 phosphono ester.

In the final reaction step, Compound O underwent a saponification reaction to form the C-15, asymmetrical derivative of TSC, Compound P. The reaction scheme is shown in the information below.

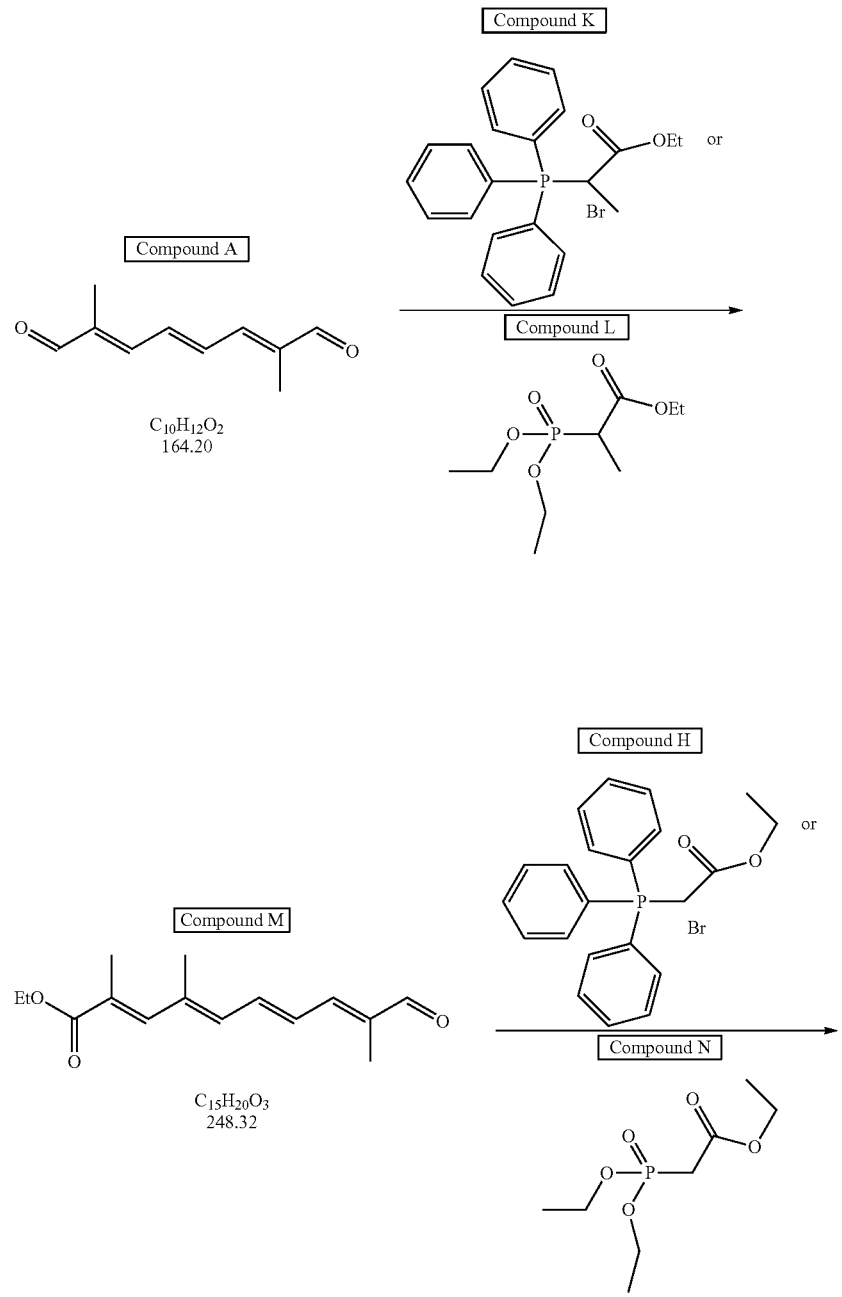

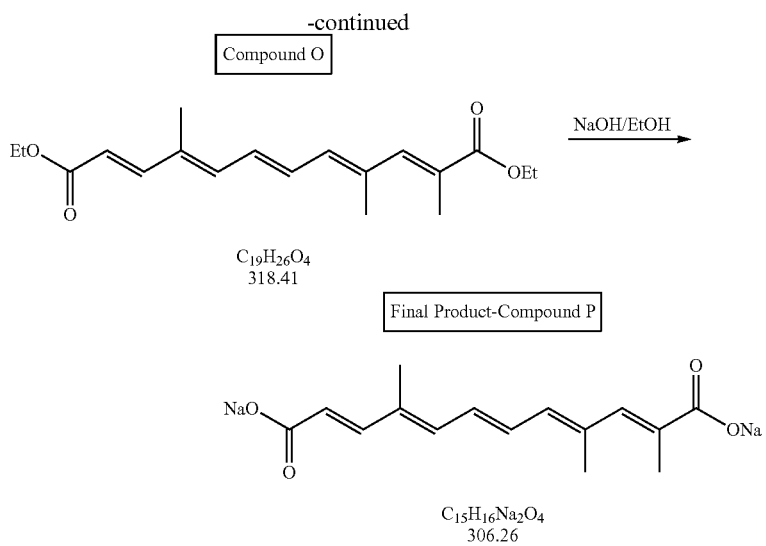

The C15 derivative required the use of two different mono coupling reactions in sequence; the first one with the C3 phosphono ester or phosphonium bromide, and the second with the C2 phosphonium bromide. Due to the formation of some C16 diethyl ester, the crude product from the first monocoupling reaction was purified by a chromatography over silica gel.

First Coupling Reaction to Form Compound M

Compound A was treated with 1 eq. C-3 phosphonium bromide (Compound K) at 100° C. for 1 day. This coupling reaction was performed in butylene oxide/toluene 2:1 (0.7 ml+1.4 ml/mmol) and showed good product formation. While cooling to room temperature and later to 0° C., no precipitation was observed. The orange mixture was then filtered over silica gel (0.33 g/mmol). The filter cake was washed with toluene (1.7 ml/mmol).

The filtrates were combined and evaporated to dryness at JT=45° C. to give a crude product that appeared as an orange oil.

Next, the reaction mixture was evaporated to dryness. The residue was slurried in MeOH to obtain the crude product in solid form and then washed with MeOH (3×). The quality of the crude product obtained was poor due to the presence of C16 diethylester in addition to the desired C13 mono coupling product, Compound M. Thus, a purification step over silica gel with 10:1 methylcyclohexane/EtOAc was performed. The crude product was dissolved in dichloromethane (0.3 ml/g crude product). The C-16 diethyl ester (about 7%) was the first compound to elute. Once this step was performed, the yield was 45% (20 g experiment). On a smaller-scale, yields were as high as 70%. The best quality product was determined to have 98.1% a/a trans isomer at a detection wavelength of 383 nm (9.22 min). An additional compound was present (1.7% a/a, 9.47 min) which was suspected to be a cis isomer of Compound M.

Second Coupling Reaction to Form Compound O

Compound M was treated with 1.5 eq C-2 phosphonium bromide (Compound H) at 100° C. This coupling reaction was performed in butylene oxide/toluene 2:1 (0.5 ml+1.0 ml/mmol) and showed a good product formation. A yellow product was isolated by filtration at 0° C. and by washing twice with methylcyclohexane. The yield at this step was 36%.

In an effort to improve the yield, the mother liquor was concentrated to about half of the original volume and cooled to 0° C. to obtain a second crop with a yield of 27%. The total yield of both crops combined was 63% (13 g scale).

The best quality product (Compound O) was determined to have 87.0% a/a trans isomer at a detection wavelength of 383 nm (12.4 min). In addition, a second compound was noted on the HPLC trace (11.3% a/a, 11.8 min) and might be a cis isomer of Compound O.

Saponification Reaction to Form the Final Product (Compound P)

The diethyl ester, Compound O, was treated with 30% NaOH (2 ml/mmol) in EtOH (4 ml/mmol) at 90° C. for 3 days. A greenish, yellow product was isolated by filtration at RT and washing with 50% EtOH in water (5×) and EtOH (3×). The saponification reaction produced a yield of 83% (6 g scale).

An $_1$H-NMR experiment confirmed the desired product, Compound P. The HPLC quality was 97.0% Compound P at a detection wavelength of 383 nm. In addition, other possible cis isomers corresponding to 1.4% a/a+1.2% a/a were noted. LCMS-data confirmed the given structure.

Example 7

Synthesis of the C-16 Derivative of TSC (disodium 2,4,9,11-Tetramethyldodedeca-2E,4E,6E,8E,10E-pentaene-1,12-diotate)

Compound A was reacted with Compound L (Triethyl-2-phosphonopropionate), a C3 phosphono ester, to form the critical intermediate in this synthesis, Compound Q. Alternatively, Compound Q can be produced by a reaction between Compound A and Compound K (1-(Ethoxycarbonyl)-ethyltriphenylphosphoniumbromide), a C3 phosphonium salt/C3 Wittig ester bromide. Although the initial reactants (Compounds A, K and L) are the same as found in Example 6, the reaction conditions used here yielded a different, symmetric intermediate, Compound Q.

In the final step of the reaction, Compound Q was reacted with sodium hydroxide and ethanol in a saponification reaction that produced the final product, Compound R. Compound R (disodium 2,4,9,11-tetramethyldodedeca-2E, 4E,6E,8E,10E-pentaene-1,12-diotate) is the C-16, symmetric derivative of TSC. The reaction scheme is shown in the information below.

a saturated NaHCO$_3$ solution and a 50% saturated. NaCl solution. The result was the production of 36.4 g of Compound Q after evaporation.

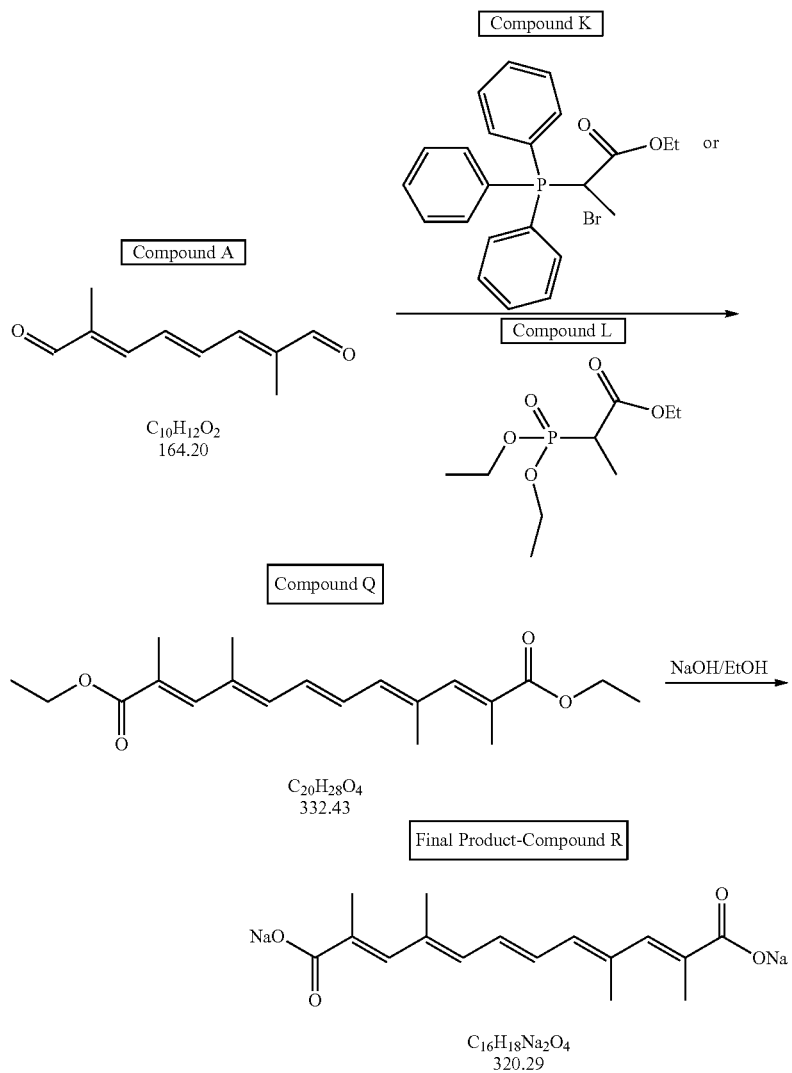

Coupling Reaction to Form Compound Q (Using Compound L as a Reactant)

The synthesis of the C16-derivative (Compound R) was commenced in a fashion similar to that shown in Example 6—a coupling reaction between Compound A and Compound L. Compound A was treated with Compound L at 100° C. in toluene/butylene oxide 2:1. No chemical reaction was observed without the addition of a base and in this case, the mixture was cooled to 0° C. and NaOMe (3 eq.) was added.

A second quantity of reagent, prepared from C-3 phosphono ester (2×1.5 eq.) and NaOMe in DCM twice, was added to the reaction mixture. The mixture was stirred at JT=65° C. and a higher percentage of desired products were observed. HPLC traces indicated that only a small percentage of unreacted Compound A was remaining (2.3% a/a). The reaction mixture was quenched with water and the organic phase was washed in a solution consisting of: water, Purification of Compound Q was undertaken using silica gel 10:1 methylcyclohexane/EtOAc. The result was 0.26 g light yellow product (Compound Q) and 4.0 g of a yellow solid (Compound M). The transesterification product, Compound Q, (dimethylester instead of the diethylester) was isolated with a yield of 32% using MeOH as a solvent. An alcohol solvent would have been suitable for the coupling reaction as well. Overall, the quality of product from this step was excellent at 85.7% purity. HPLC experiments showed the majority of the impurities were cis isomers of Compound Q.

Coupling Reaction to Form Compound Q (Using Compound K as a Reactant)

In a second experiment to synthesize Compound Q, Compound K was substituted for compound L in the coupling reaction. This substitution showed a better overall reaction conversion. The coupling reaction between Compound A and Compound K was performed in a mixture of butylene oxide/toluene 2:1 (0.9 ml+1.8 ml/mmol) and showed good product formation with 3 eq. Wittig reagent at JT=100° C. (22 h). The yellow product was isolated by filtration at 0° C. and by washing twice with methylcyclohexane. The yield was 61-62% (10 g scale). HPLC analysis showed a purity of Compound Q at 85.2% a/a trans isomer at 369 nm (13.3 min) with the major impurity being a cis isomer.

Saponification Reaction to Form the Final Product (Compound R)

The saponification reaction to produce Compound R was conducted in a manner similar to that described in Example 5. The diethyl ester (Compound Q) was treated with 30% NaOH (2 ml/mmol) in EtOH (4 ml/mmol) at 90° C. for 3 days. The saponification gave a yield of 85% (12.5 g scale) after filtration at RT and washing with 50% EtOH in water (3×) and EtOH (3×). The $_1$H-NMR confirmed the desired product was Compound R. The HPLC quality was 95.7% with a detection wavelength of 383 nm. Additionally, 3.8% cis isomer was observed. LCMS-data confirmed the given structure.

Example 8

Synthesis of the C-17 Derivative of TSC (disodium 2,6,11-Trimethyltetradeca-2E,4E,6E,8E,10E, 12Ehexaene-1,14-diotate)

The preparation of a longer-chain, asymmetric derivative of TSC was performed using Compounds A and D as starting materials as in Examples 1-2. However, in this case, the reaction conditions were changed to favor the formation of the first coupling intermediate, Compound S. Compound S was then reacted in a second coupling reaction with Compound H to form Compound T. In the final step of this reaction sequence, Compound T underwent a saponification reaction with sodium hydroxide and ethanol to form the final, desired product, Compound U. Compound U is the C-17 derivative of TSC and asymmetric in the placement of the pendant methyl groups around the diene backbone. Details of the synthetic sequence are shown in the information below.

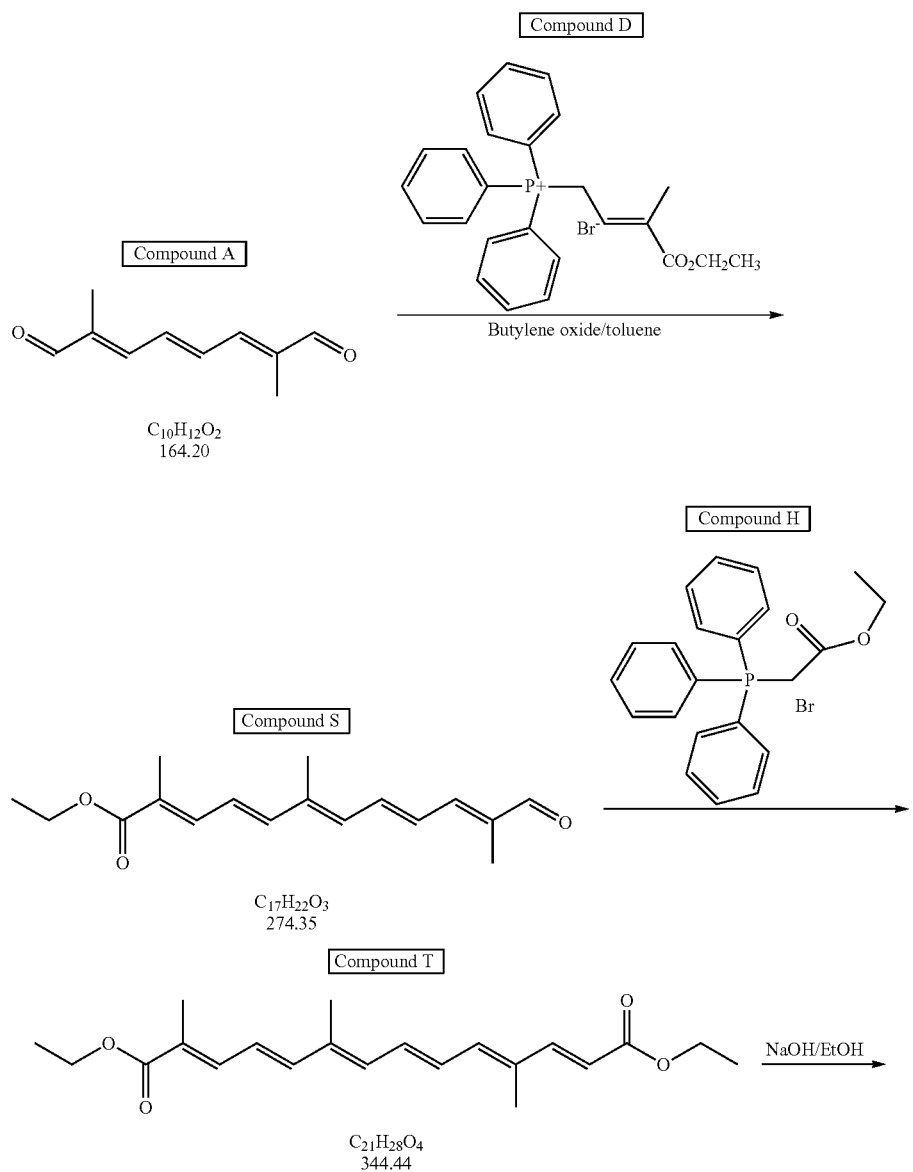

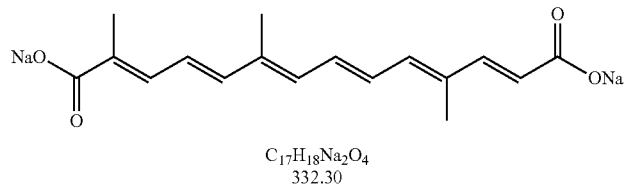

Compound U $C_{17}H_{18}Na_2O_4$
332.30

First Coupling Reaction to Form Compound S

Compound A was treated with 1 eq. Compound D at 100° C. for 1 day. This coupling reaction was performed in butylene oxide/toluene 2:1 (0.44 ml+0.88 ml/mmol) as used in Example 1 and showed a good product formation. During a subsequent cooling step at 0° C., a suspension was formed from the original dark red solution. Ultimately, a red-orange solid was isolated by filtration at 0° C. and by washing with methylcyclohexane (3×). This red-orange solid was identified as Compound E, previously described in Examples 1-4. The yield of Compound E in this situation was approximately 4%.

The mother liquor, from the previously described step, was evaporated to dryness at JT=45° C. to give the crude Compound S product as a red oil. The quality of the obtained crude product was poor due to the presence of some Compound E in addition to the desired product, Compound S. In order to isolate Compound S, a purification step over silica gel with 8:1 methylcyclohexane/EtOAc was performed. For that, the crude product was solvated first in dichlormethane (0.3 ml/g crude product). The first eluted product from this mixture was the C-20 diethyl ester (Compound E). The remaining fraction contained a mixture of compounds including the desired Compound S. The yield after this step was 46% (30 g experiment) of an orange solid. The quality was determined (by HPLC) to be 71.2% a/a trans isomer at a detection wavelength of 369 nm (10.4 min). In addition, two further compounds were identified 0% a/a+4.9% a/a) which are likely to be cis isomers of Compound S.

Second Coupling Reaction to Form Compound T

Compound S was reacted with 1.5 eq Compound H at 100° C. This coupling reaction was performed in butylene oxide/toluene 2:1 (0.6 ml+1.2 ml/mmol) and showed a good product formation. The red product, Compound T, was isolated by filtration at 0° C. and washing twice with methylcyclohexane. The yield was 58% (10 g scale). The quality was determined to be 97.2% a/a trans isomer at a detection wavelength of 421 nm (14.2 min). In addition, two other compounds were detected and are speculated to be cis isomers of Compound T.

Saponification Reaction to Form Compound U

The saponification reaction was performed in a similar fashion to Examples 1-4. Compound T was treated with 30% NaOH (2 ml/mmol) in EtOH 2 ml/mmol) at 90° C. for 4 days. After 2 days, the mixture was diluted with water (1 ml/mmol). The yellow product, Compound U, was isolated by filtration at RT and washing with 50% EtOH in water (2×) and EtOH (3×). The saponification reaction showed a yield of 93% (7 g scale). The $_1$H-NMR confirmed the desired product was Compound U. The HPLC quality was 98.4% at a detection wavelength of 399 nm with one major impurity found at 0.7%.

Example 9

Synthesis of the C-18 Derivative of TSC (Disodium 2,4,9,13-Tetramethyltetradeca-2E,4E,6E,8E, 10E,12Ehexaene-1,14-diotate)

The C18 derivative of TSC, Compound W, was prepared via two sequential mono coupling reactions as seen in Examples 6 and 8 within this application. The first coupling reaction was commenced as in Example 8 leading to the formation of Compound S. In the second coupling reaction, Compound S was reacted with Compound K to form the penultimate intermediate, Compound V. The final, desired product—Compound W, was produced via the saponification reaction of Compound V. The information below illustrates the details of the synthetic sequence.

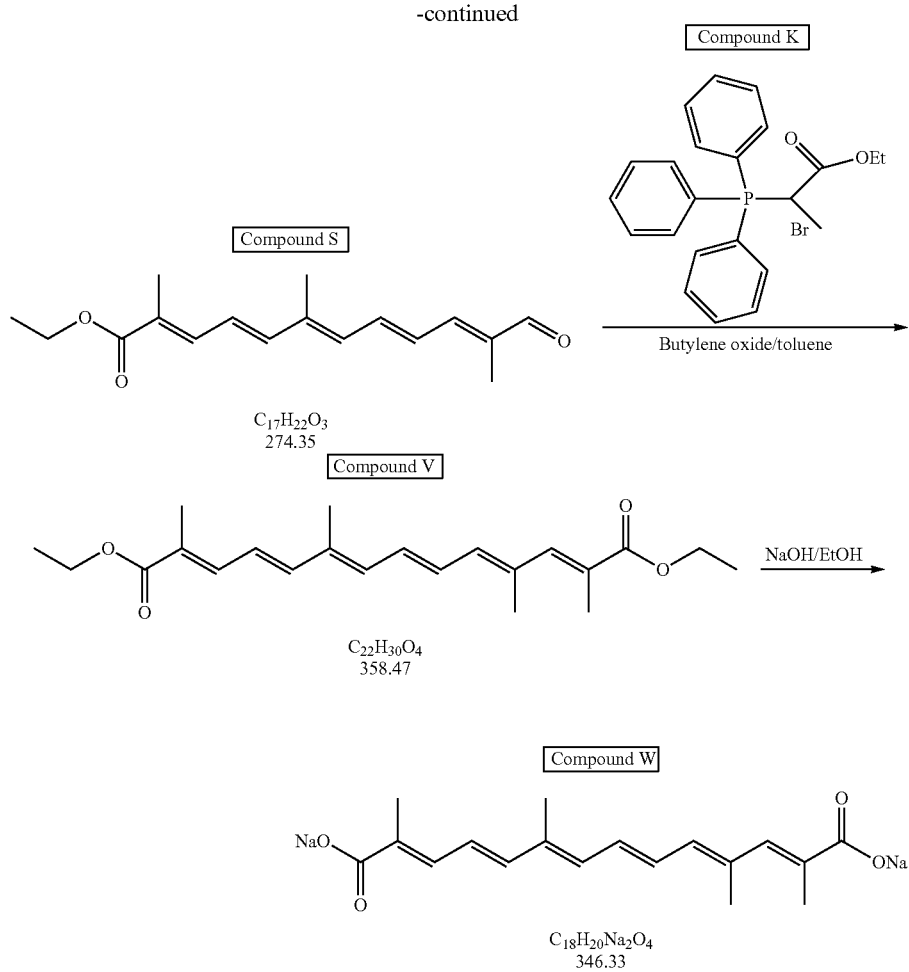

First Coupling Reaction to Form Compound S

The first coupling reaction shown above, leading to the formation of Compound S, is described previously in this application in Example 8. The method used in this example is identical.

Second Coupling Reaction to Form Compound V

The second coupling reaction was performed by reacting Compound S (also known as the C15 monoester) with 1.5 eq. Compound K (a C-3 phosphonium bromide) at 100° C. This coupling reaction was performed in butylene oxide/toluene 2:1 (0.6 ml+1.2 ml/mmol) and showed a good product formation. An orange product was isolated by filtration at 0° C. and by two washing steps in methylcyclohexane. The yield for this step was 56% (9 g scale). The quality of Compound V was measured using HPLC and found to be 96.7% a/a trans isomer at a detection wavelength of 369 nm (14.2 min). In addition, the major impurity observed (1.7% a/a, 13.6 min) is speculated to be a cis-isomer of Compound V.

Saponification Reaction to Form Compound W

The saponification reaction was performed in a similar fashion to the previous examples. Compound V was treated with 30% NaOH (2.2 ml/mmol) in EtOH (3.4 ml/mmol) at 90° C. for 4 days. After 2 days, the mixture was diluted with water (1.1 ml/mmol). A yellow product was isolated by filtration at RT and washing with 50% EtOH in water (2×) and EtOH (3×). The saponification reaction gave a yield of 98% (6 g scale). The $^1$H-NMR confirmed that the product obtained was the desired product, Compound W. HPLC analysis showed the purity of Compound W was 99.2% at a detection wavelength of 405 nm. In addition, an impurity of 0.3% a/a/was observed and is believed to be a cis isomer of Compound W.

Example 10

Synthesis of the C-24 Derivative of TSC (Disodium 4,8,13,17-Tetramethyleicosa-2E,4E,6E,8E, 10E,12E,14E,16E,18 Enonaene-1,10-diotate)

The longer chain derivatives of TSC required the use of multi-step synthetic processes involving reduction and oxidation steps. This example illustrates the synthesis of the C24 derivative of TSC (Disodium 4,8,13,17-Tetramethyleicosa-2E,4E,6E,8E,10E,12E,14E,16E,18 Enonaene-1,10-diotate). The synthesis commenced with Compound E, the starting point for several examples already described in this application. Compound E (a diethyl ester) was converted to a Compound X, a dialcohol, via a reduction step. The third step in the reaction sequence was an oxidation of Compound X with MnO$_2$ to form Compound Y. The next step consisted of a coupling reaction with Compound H to form Compound Z and a final saponification step to form the desired product, Compound AA (the C-24 derivative of TSC). The reaction sequence is shown below.

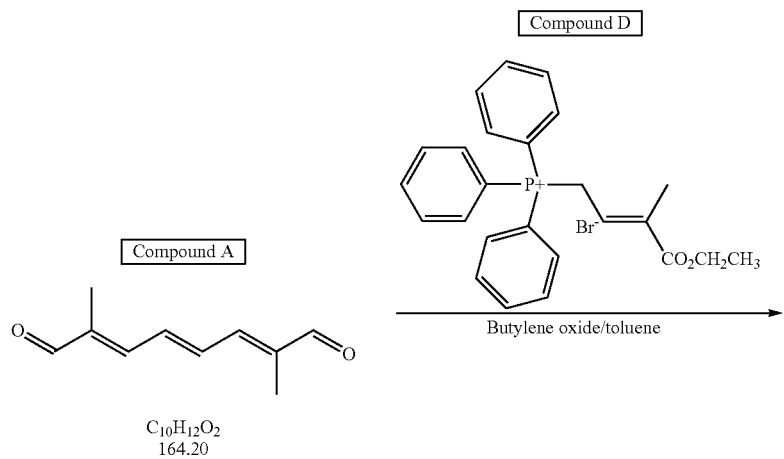
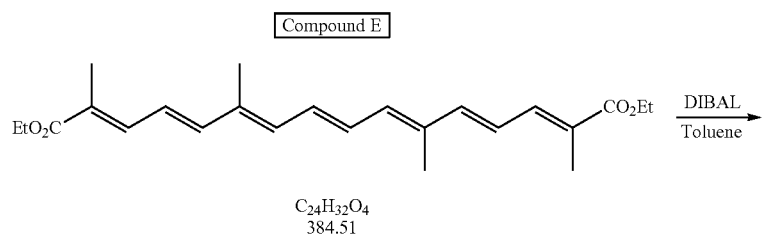
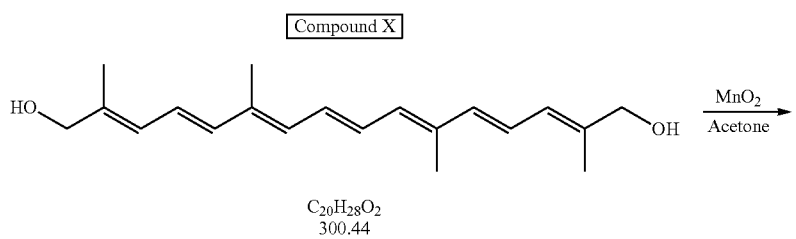
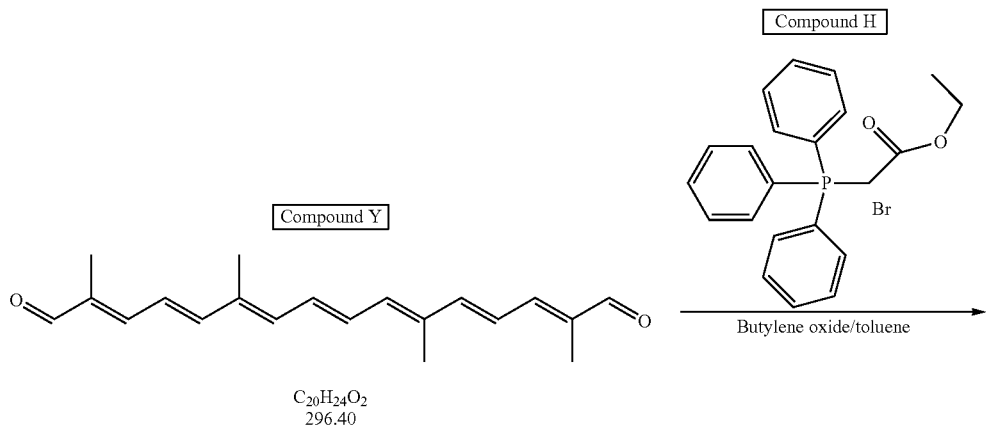
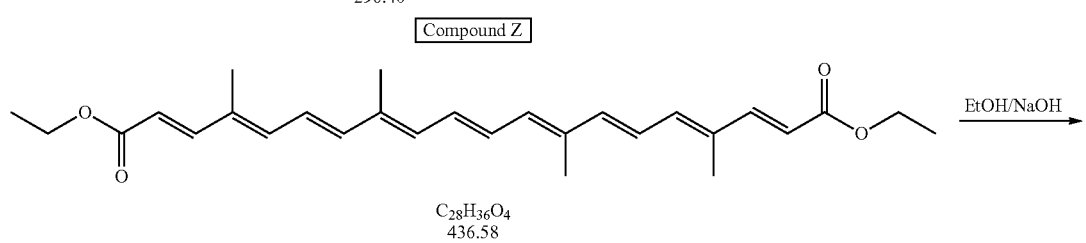

-continued

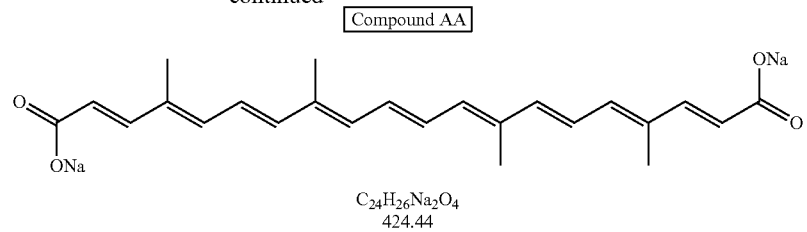

$C_{24}H_{26}Na_2O_4$
424.44

Reaction to Form Compound E

The coupling reaction between Compounds A and D to form Compound E has been described earlier in Examples 1-4.

Reduction Reaction to Form Compound X 40 g diethyl ester (Compound E) was suspended in toluene and treated with DiBAl (6 eq.) at JT=−70° C. The mixture was stirred for 4.5 h. at JT=−70° C. An IPC revealed complete conversion. The mixture was quenched with 2 M HCl at −77° C.

The mixture was divided in three portions. Each portion was diluted with water and THF. The organic layer was washed 3× with brine. The combined organic layers were evaporated at JT=45° C. to give 30.63 g of an orange solid, which corresponded to a yield of 98%. Re-extraction of the aqueous layers gave further 1.48 g orange solid.

From the process described above, an orange product was obtained with a quality of 89.0% a/a as measured by HPLC. In addition, an impurity, believed to be an aldehyde side reaction product, was observed at a concentration of 4.8% a/a isomer.

Furthermore, a separate study was undertaken to determine whether the reduction reaction could have been performed with LAH or $NaBH_4$. The LAH reduction (2 eq.) in THF at 0° C. while slowly warming to RT within 4 h gave a yield of about 80% in a 1 g experiment, but the quality was not as high as with the DiBAl-H method. But this reagent can be an option for further evaluations on this step. In contrast, the reduction with $NaBH_4$ (2 eq.) in THF was found not to be appropriate for this step. Additionally, the addition of MeOH as a co-solvent did not improve the reaction.

Oxidation Reaction to Form Compound Y

Two experiments were conducted in an effort to optimize the oxidation reaction to form Compound Y. In the first experiment, the oxidation reaction was performed using a low concentration of Compound X (1.7%) in acetone and an excess of $MnO_2$ (30 eq.). The reaction was started at 0° C. while warming to RT over the course of 1 day. The reagent was removed by filtration over celite or silica gel and evaporation to give a purple solid product at a yield of 42-57%. The quality of product was measured by 87.7% a/a HPLC at a detection wavelength of 421 nm. This approach led to a high-purity product as measured by HPLC.

As a second approach to conducting the oxidation reaction, a small-scale experiment was conducted with focus on the crystallization procedure. The use of an acetone/water mixture at a ratio of 2:3 (0.013 g/ml) as the solvent yielded the best results at this step. Other solvents such as dioxane/MCH (1:2), THF and EtOAc did not produce better crystallization results. The one parameter that did improve crystallization was changing the jacket temperature. Raising the jacket temperature to 75° C. significantly improved the conversion to product and reduced the amount of $MnO_2$ required for the overall reaction to 10 eq. from 30 eq. A more detailed description of the steps taken in this modified approach is described in the following paragraph.

5 g Compound X was suspended in acetone and treated with 5 eq. $MnO_2$ at JT=75° C. The mixture was stirred for 2 days at 75° C. An IPC revealed the presence of dialdehyde and monoaldehyde species in addition to the starting material. As a result, an additional 5 eq. $MnO_2$ was added to drive the reaction further towards completion. After 8 hours reaction time, most starting material and intermediate was consumed. The mixture was cooled and filtered first over silica gel and then subsequently over celite. The double filtration step was necessary to remove $MnO_2$. A third filtration step over a membrane was conducted. In total, washing the filter cakes with THF resulted in 0.7 g red product besides 1.95 g+2.51 g dark brown product with traces of manganese. The total mass yield for the reaction was 5.16 g (99.6%). HPLC of an IPC: 61.0%+5.4%+19.3% (including isomers) at 463 nm.

In this second approach to the oxidation reaction, while the product yield was higher than the first synthetic sequence, the HPLC quality was not as high with residual amounts of manganese oxide remaining in the Compound Y product.

It should be noted that in either approach, the intermediate (monoaldehyde) must be consumed to achieve good yields and qualities. Manganese residues can be removed via a solvent exchange with hot THF or EtOAc prior to the filtration step.

Coupling Reaction to Form Compound Z

The synthesis of the C24 diethylester (Compound Z) was performed in a similar fashion to Examples 5, 6 and 8 using Compound H. The C20 dial (Compound Y) was treated with Compound H at 100° C. in toluene/butylene oxide 2:1 (1 ml and 0.5 ml/mmol) for 1 day. While cooling to RT, no precipitation was observed. A clear, deep red solution was still present.

The mixture was then evaporated to dryness at JT=40-50° C. The residue was treated with MeOH (1.25 mmol/mmol) and cooled to 0° C. The suspension was filtered and the filter cake was washed twice with methanol. This step resulted in a red-brown product after drying on a rotary evaporator at JT=50° C.

The yield for this reaction was 19-22%. This yield could be improved with further reclamation of product from the mother liquor. The best quality was determined to be 92.4% a/a trans isomer (of Compound Z) at a detection wavelength of 421 nm (16.8 min). Additional compounds observed in the HPLC spectrum are believed to be cis isomers of Compound Z.

Saponification Reaction to Form Compound AA

The saponification reaction was performed in a fashion similar to those previously reported in this filing. The diethyl ester (Compound Z) was treated with 30% NaOH (3 ml/mmol) in EtOH (3 ml/mmol) at 90° C. for 3 days. The saponification reaction produced a yield of 83% (0.8 g scale)

after dilution with water (6 ml/mmol) and ethanol (3 ml/mmol), filtration at RT and washing with 50% EtOH in water (12 ml/mmol) and EtOH (12 ml/mmol). The HPLC quality was 95.3% Compound AA at 463 nm in addition to 0.5% cis-isomer.
Example 11
Synthesis of the C-26 Derivative of TSC (Disodium 2,4,8,13,17,19-Hexamethyl-eicosa-2E,4E,6E, 8E,10E,12E,14E,16E,18Enonaene-1,10-diotate)
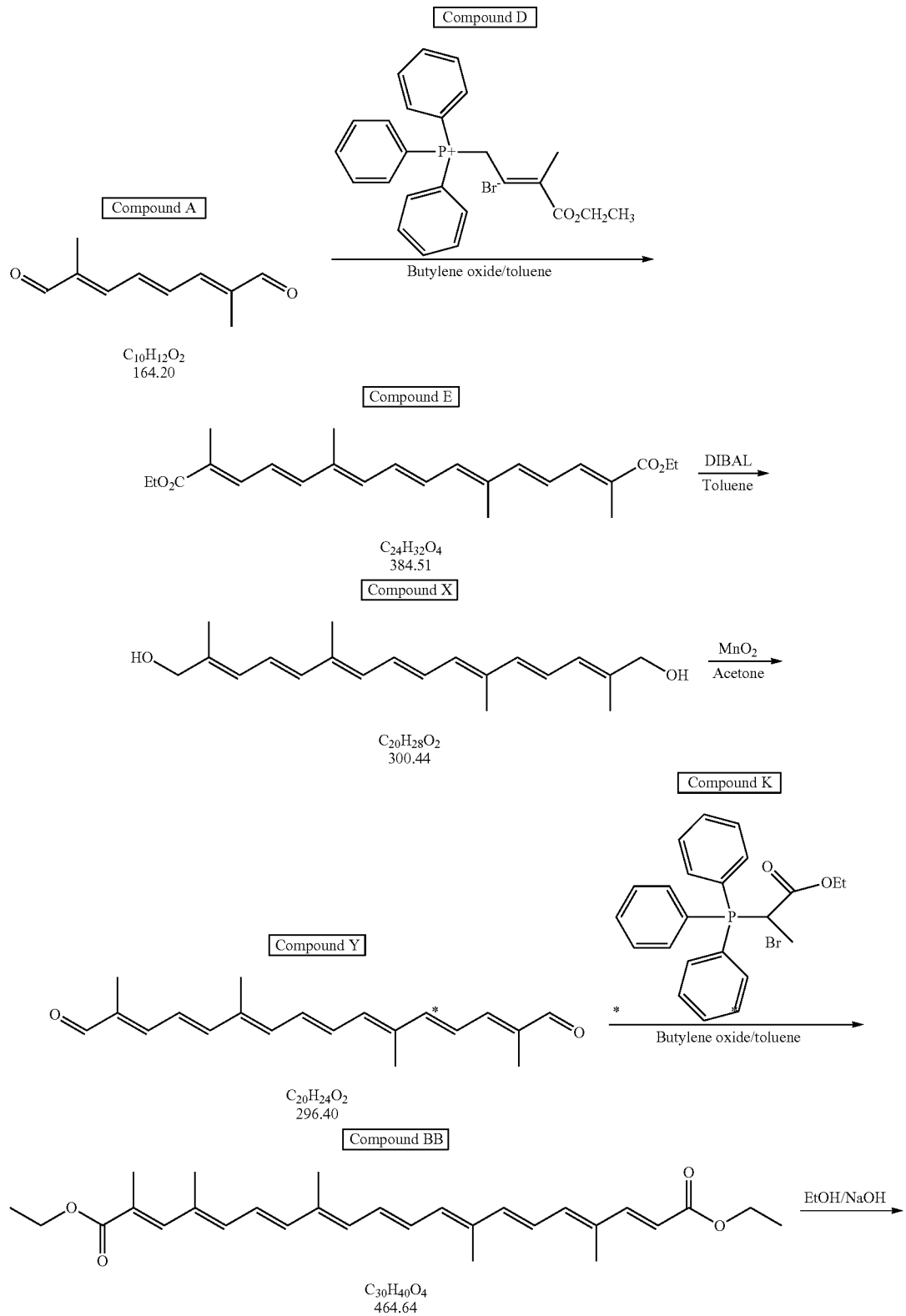

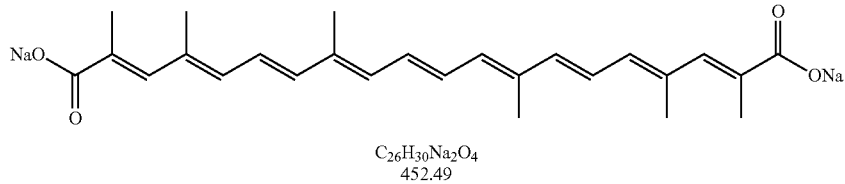

$C_{26}H_{30}Na_2O_4$
452.49

Reaction Sequence to Form Compound Y

The reaction sequence required to form Compound Y was previously described in Example 10. The same sequence was followed for this example.

Coupling Reaction to Form Compound BB

The synthesis of the C26 diethylester commenced from the production of Compound Y as described in Example 9. Compound Y was treated with Compound K at 100° C. in toluene/butylene oxide 2:1 (2 ml and 1 ml/mmol) for 1 day. While cooling to RT no precipitation was observed. A clear, deep red solution was still present. The mixture was cooled to 0° C. The resulting suspension was filtered. Afterwards the filter cake was washed three times with MeOH to give a dark purple solid after drying on a rotary evaporator at JT=45° C.

The yield at this step was between 17-26%. One of the major reasons was that some of the product remained in the mother liquor. The best quality product was determined to have 83.9% a/a trans isomer at a detection wavelength of 463 nm (by HPLC). Additional compounds that were observed are speculated to be cis isomers of Compound BB. This experiment was conducted on a 1.5 g scale.

Saponification Reaction to Form Compound CC

The saponification reaction was performed in a similar fashion to that described in Example 9. The diethyl ester (Compound BB) was treated with 30% NaOH (3 ml/mmol) in EtOH (3 ml/mmol) at 90° C. for 3 days. The saponification reaction gave a yield of 84% (0.8 g scale) after dilution with water (6 ml/mmol) and ethanol (3 ml/mmol), filtration at RT and washing with 50% EtOH in water (12 ml/mmol) and EtOH (12 ml/mmol). The $^1$H-NMR confirmed the desired product was obtained (Compound CC). The HPLC quality was 91.5% at a detection wavelength of 460 nm. In addition, 0.2% cis-isomer was observed.

Example 12

Formulation of TSC with Cyclodextrin-Mannitol
1. Make up a solution containing equal-molar concentrations of the cyclodextrin and the TSC. Solutions containing over 20 mg TSC/ml of solution can be made this way. First, add the cyclodextrin to an injectable water, then add the TSC to that solution.
2. Add d-mannitol, so that the final concentration is around 20 to 50 mg/ml of mannitol in solution.
3. This solution can be added to isotonic saline in order to dilute it and still maintain the proper osmolality. Either add the solution to saline or add saline to the solution.

Example 13

Formulation of TSC with Mannitol/Acetic Acid
1. Make up a 0.01 M acetic acid solution in distilled water.
2. Combine this solution with an injectable water in proper proportions so as to have a final acetic acid concentration of 0.0005 M. Note: Do not use much stronger acetic acid. For example, 0.0006 M is okay, but 0.001 M doesn't dissolve the TSC.
3. Add the 0.0005 M acetic acid solution, slowly, to TSC. Maximum solubility is around 6 to 6.5 mg TSC/ml solution.
4. Add d-mannitol to above solution at a concentration of 50 mg/ml in order to obtain the proper osmolality. The pH of this solution is around 8 to 8.5. It should be close to being an isotonic solution, and, as such, can be injected directly into the blood stream.

Example 14

Pulmonary Administration

TSC has been shown, in rats, to be absorbed into the blood stream following pulmonary administration. In this method, the rats were intubated and a small volume (0.1 mL usually) of the TSC solution was injected followed by two 3-mL puffs of air. It was found that 40 to 70% of the dosage given was rapidly present in the blood stream (time to reach the maximum plasma concentration was less then 5 minutes).

Additional studies have been done with pulmonary dosing in which the effect of the volume of liquid injected into the trachea as well as using TSC in its formulated drug product form were investigated. The formulated drug product contained 8% γ-cyclodextrin, 2.3% mannitol and 50 mM glycine and 20 mg/mL TSC, reconstituted in sterile water. Sterile saline (0.9%) was added as a diluent in these studies in order to achieve the desired dosages. The same dose (937 μg/kg) was administered to all rats.

It was found that the incorporation of the γ-cyclodextrin appears to enhance absorption of TSC into the systemic circulation—with the overall effect of increasing plasma clearance. Also, an increase in the injection volume results in greater TSC absorption and over a longer period of time. Thus, a larger volume injection of the same dose results in a greater bioavailability. It should also be noted that it has been found that hemorrhagic shock in rats can be successfully treated by administering TSC via the pulmonary route.

Example 15

Intramuscular Administration

TSC is not absorbed via an intramuscular route when simply dissolved in de-ionized water; however, the addition of a cyclodextrin (as in the formulated drug product) results in absorption into the blood stream. Small volumes (0.05 mL) were injected into each thigh muscle of rats with TSC formulated with 2-hydroxypropyl-β-cyclodextrin or γ-cyclodextrin and dissolved in water. Intramuscular administration of 3347 μg/kg body weight (with 14 mg 2-hydroxypropyl-β-cyclodextrin per kg body weight) resulted in a peak plasma TSC concentration of 4.8 μg/mL and a bioavailability of 0.27. Administration of γ-cyclodextrin with TSC also resulted in successful absorption into the systemic circulation. Hemorrhagic shock in rats was successfully treated by administering TSC via intramuscular injection.

Example 16

Transdermal Administration

TSC has been shown, in rats, to be absorbed into the blood stream following transdermal administration. For these studies, select areas around the abdomen and/or outer thigh was either cut and/or shaved to expose the stratum corneum. The formulated drug product (8% γ-cyclodextrin, 2.3% mannitol and 50 mM glycine and 20 mg/mL TSC) was applied to the exposed stratum corneum and 0.25 to 0.5% of the dosage given was present in the blood stream at a time of 15 to 30 minutes after being given.

Example 17

Oral Administration

PE-50 tubing was used to deliver formulated TSC into the stomachs of rats, and plasma concentrations were measured after that. Rats were fasted for 24 hours prior to each experiment. Water was given ad libitum and coprophagy was prevented by using cages with wire-mesh floors. One study involved rats that were allowed food ad libitum after TSC administration and another study involved rats in which food was withheld after TSC administration. The dose of TSC given in both groups was 55 mg/kg and it was found that 1 to 2% of the dosage was present in the blood stream at a time of 15 to 30 minutes after being given.

Example 18

Endotoxin Removal of Gamma-Cyclodextrin

Commercially available pharmaceutical grade gamma cyclodextrin obtained from the manufacturer has endotoxin levels that are incompatible with intravenous injection. The endotoxin levels must be reduced in order to use the gamma cyclodextrin in a TSC formulation intended for intravenous injection. A process utilizing multiple filtration passes of a cyclodextrin solution through an endotoxin removal filter (Millipore 0.22 micron Durapore filter) was developed that reduces endotoxin levels about 10 to 30 fold. The recovery of cyclodextrin is 90-100%. An example of the results obtained by using this process on an 8% gamma cyclodextrin solution is in the table below.

| Filtration Steps | Endotoxin levels (EU/mg of cyclodextrin) |
| --- | --- |
| prefiltered | 0.226 |
| After 1 filtration | 0.0246 |
| After 2 filtrations | 0.0125 |
| After 3 filtrations | 0.0125 |

Example 19

Lyophilization

Lyophilization process to produce a cake of less than 3% moisture is as follows:

| Step | Temp (degrees C.) | Pressure | Time (hours) |
| --- | --- | --- | --- |
| Loading | ambient | n/a | n/a |
| Freezing | −30 | n/a | 1 |
| Freezing | −30 | n/a | 6 |
| Evacuation | −30 | 225 um | n/a |
| Drying | −30 | 225 um | 2 |
| Drying | 30 | 225 um | 15 |
| Drying | 30 | 225 um | 4 |
| Drying | 30 | 50 um | 99 |

Diluent

A diluent of glycine buffer (e.g. 50 mM glycine buffer with 2-4% mannitol) with osmolality adjusted with mannitol can be used as a diluent.

Example 20

Radiation Sensitization

HCT116 human colon carcinoma tumors measuring between 0.25 and 0.35 cm$^3$ were grown on the hind legs of athymic male mice (6-7 weeks at purchase), which required 2-3 weeks growth before use. Because patients are not normally anesthetized during radiotherapy (anesthesia may decrease blood flow to the tumor and make it more hypoxic), the study was performed with non-anesthetized animals.

There were six study groups of five mice per group (for a total of 30 mice) designated Study Groups 1 through 6. All mice in the study were injected intravenously with either a TSC dose or a saline control for five successive days. As shown below, Study Groups 1, 2 and 3 received TSC doses A, B and C, which corresponds to 0.07, 0.14 and 0.28 mg/kg respectively for the study B, and 1.35, 0.54 and 0.18 mg/kg respectively for the study A.

| Designation | N (Athymic Male Mice) | Dose | Radiotherapy |
| --- | --- | --- | --- |
| Group 1 | Five (5) | TSC Dose A | Yes |
| Group 2 | Five (5) | TSC Dose B | Yes |
| Group 3 | Five (5) | TSC Dose C | Yes |
| Group 4 | Five (5) | Saline Control | Yes |
| Group 5 | Five (5) | TSC Dose B | No |
| Group 6 | Five (5) | Saline Control | No |

Figure 2:
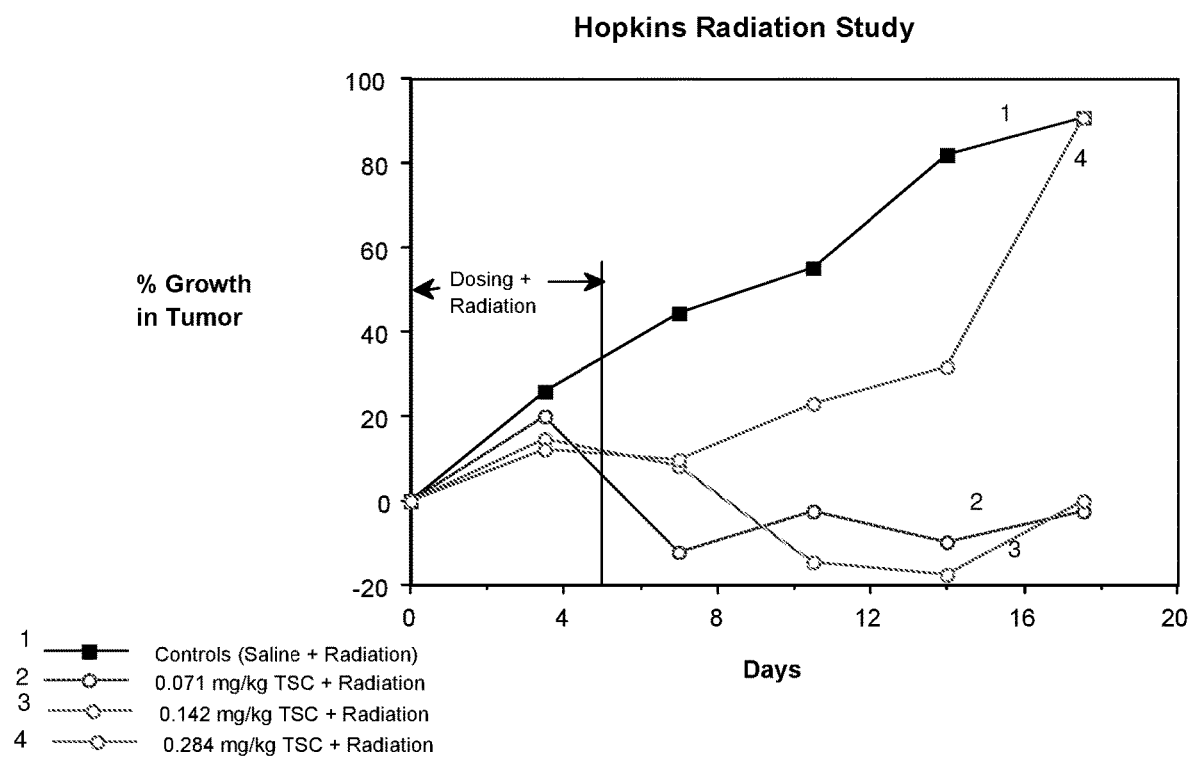
FIG. 2 is Study B Results of Radiation Study.

Group 4 was injected as a saline control. At 45 minutes post-injection on each of the five successive days, the tumors of Study Groups 1-4 received 2 Gy irradiation. Study Group 5 received TSC only and Study Group 6 received saline only, and neither Study Group 5 nor 6 received irradiation. Tumor volumes in all Study Groups were measured weekly for the earlier of 4 weeks or until the tumors reached 4 times the volume at the start of treatment. The results from these tests are shown in FIGS. 1 and 2.

Figure 3:
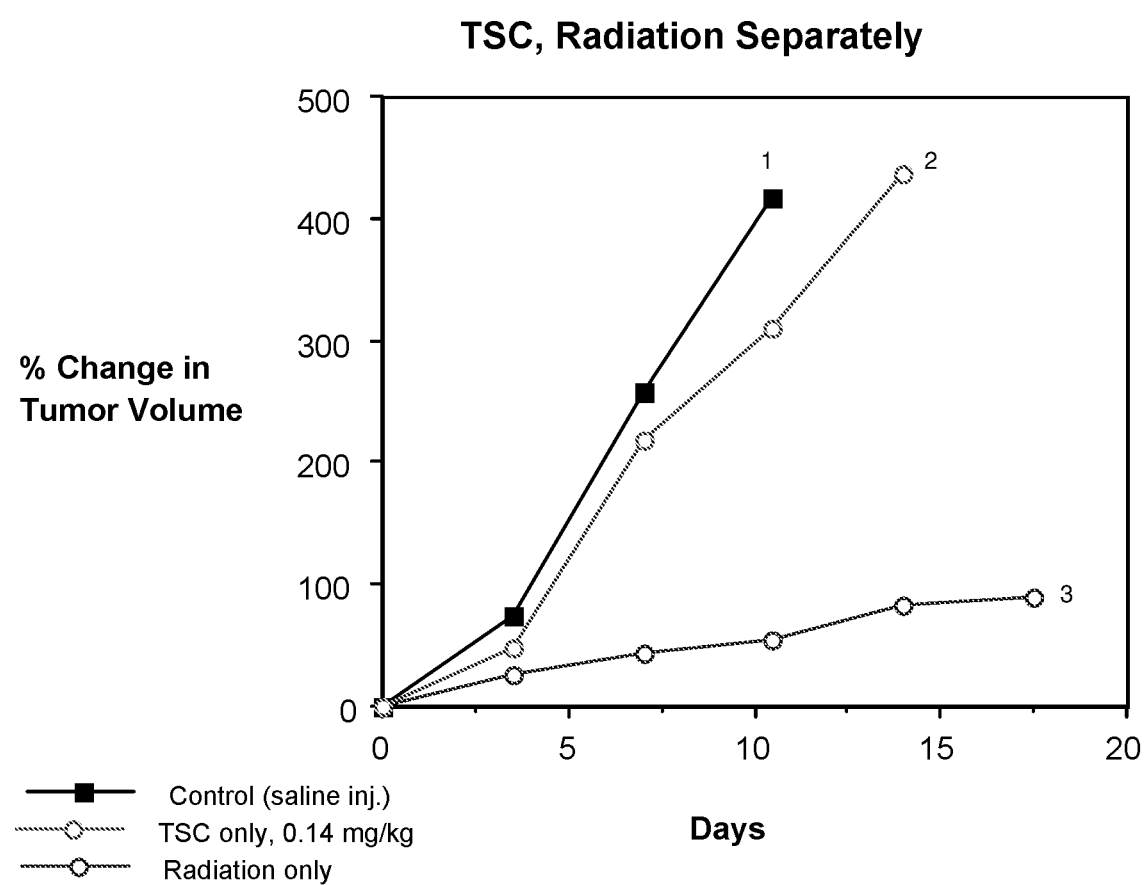
FIG. 3 is a graph of TSC, Radiation Separately.

The optimal dosage for the Study A was 0.18 mg/kg and for the Study B, the dosages of 0.07 and 0.14 mg/kg worked equally well. The use of TSC alone was also studied. Those results are shown in FIG. 3, along with the effect of radiation alone (which is also shown in FIG. 2). It can be seen that TSC alone does not appreciably affect tumor growth.

It will be readily apparent to those skilled in the art that numerous modifications and additions can be made to both the present compounds and compositions, and the related methods without departing from the invention disclosed.

What is claimed is:

1. A method of treating a condition in a mammal selected from tachycardia, fibromyalgia, smoke inhalation, elevated plasma lipid levels, oxygen deprivation in a fetus during labor, and insufficient oxygenation in premature babies, comprising administering to said mammal a pharmaceutical composition, wherein the pharmaceutical composition comprises i) a bipolar trans carotenoid salt having the formula YZ-TCRO-ZY where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and
ii) a cyclodextrin.

2. A pharmaceutical composition, wherein the pharmaceutical composition comprises:
i) a bipolar trans carotenoid salt having the formula:

YZ-TCRO-ZY where: Y=a cation which can be the same or different, Z=a polar group which can be the same or different and which is associated with the cation, and TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and the absorbency of the highest peak which occurs in the visible wave length range of the bipolar trans carotenoid salt divided by the absorbency of the peak which occurs in the UV wave length range is greater than 7.0, and
ii) a cyclodextrin.

3. A composition as in claim 2, wherein the bipolar trans carotenoid salt is a lithium, potassium or sodium salt.

4. A composition as in claim 3, wherein the bipolar trans carotenoid salt is trans sodium crocetinate (TSC) having the structure:

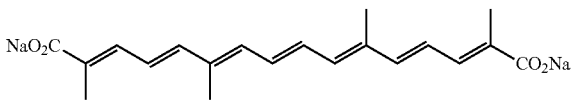

5. A composition as in claim 4, wherein the bipolar trans carotenoid salt is trans sodium crocetinate (TSC) having the structure:

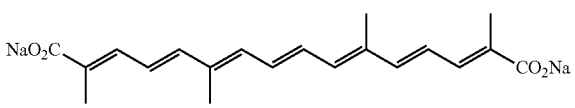

and the cyclodextrin is selected from the group consisting of alpha cyclodextrin, beta cyclodextrin, 2-hydroxypropyl-beta-cyclodextrin, 2-hydroxypropyl-gamma-cyclodextrin, and gamma cyclodextrin.

6. A composition as in claim 5, wherein the bipolar trans carotenoid salt is trans sodium crocetinate (TSC) having the structure:

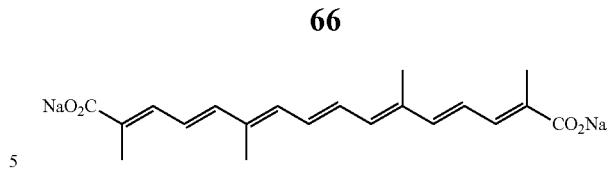

and the cyclodextrin is gamma cyclodextrin.

7. A composition as in claim 4, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 7.5.

8. A composition as in claim 4, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 8.

9. A composition as in claim 4, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is 7.5 to 8.5.

10. A composition as in claim 5, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 7.5.

11. A composition as in claim 5, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 8.

12. A composition as in claim 5, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is 7.5 to 8.5.

13. A composition as in claim 6, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 7.5.

14. A composition as in claim 6, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is greater than 8.

15. A composition as in claim 6, wherein the absorbency in aqueous solution of the highest peak which occurs in the visible wave length range of 380 to 470 nm of the trans sodium crocetinate divided by the absorbency of the peak which occurs in the UV wave length range of 220 to 300 nm is 7.5 to 8.5.

16. A composition as in claim 4, wherein the composition is lyophilized.

17. A composition as in claim 5, wherein the composition is lyophilized.

18. A composition as in claim 6, wherein the composition is lyophilized.

19. A composition as in claim 10, wherein the composition is lyophilized.

20. A composition as in claim 11, wherein the composition is lyophilized.

21. A composition as in claim 12, wherein the composition is lyophilized.

22. A composition as in claim 13, Therein the composition is lyophilized.

23. A composition as in claim 14, wherein the composition is lyophilized.

24. A composition as in claim 15, wherein the composition is lyophilized.

25. A composition as in claim 4, wherein the composition further comprises mannitol.

26. A composition as in claim 5, wherein the composition further comprises mannitol.

27. A composition as in claim 6, wherein the composition further comprises mannitol.

28. A method as in claim 1, wherein the bipolar trans carotenoid salt is trans sodium crocetinate (TSC) having the structure:

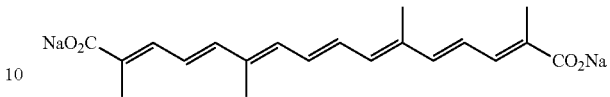

29. A method as in claim 28, wherein the absorbency of the highest peak which occurs in the visible wave length range of the trans sodium crocetinate divided by the absorbency of the peak which occurs in the UV wave length range is greater than 7.0.

* * * * *